(12) United States Patent
Yano

(10) Patent No.: US 8,088,777 B2
(45) Date of Patent: Jan. 3, 2012

(54) UREA DERIVATIVE

(75) Inventor: Toshisada Yano, Kobe (JP)

(73) Assignee: Shionogi & Co., Ltd., Osaka (JP)

( * ) Notice: Subject to any disclaimer, the term of this patent is extended or adjusted under 35 U.S.C. 154(b) by 261 days.

(21) Appl. No.: 12/310,490

(22) PCT Filed: Aug. 28, 2007

(86) PCT No.: PCT/JP2007/066607
§ 371 (c)(1),
(2), (4) Date: Feb. 26, 2009

(87) PCT Pub. No.: WO2008/026564
PCT Pub. Date: Mar. 6, 2008

(65) Prior Publication Data
US 2009/0203712 A1 Aug. 13, 2009

(30) Foreign Application Priority Data
Aug. 30, 2006 (JP) ................. 2006-233033

(51) Int. Cl.
*A61K 31/4965* (2006.01)
*C07D 413/12* (2006.01)
(52) U.S. Cl. ................. 514/254.02; 544/368
(58) Field of Classification Search ........................ None
See application file for complete search history.

(56) References Cited

U.S. PATENT DOCUMENTS

| 4,350,781 | A | 9/1982 | Rasshofer et al. |
| 5,232,898 | A | 8/1993 | Suchy et al. |
| 6,329,395 | B1 | 12/2001 | Dugar et al. |
| 2004/0044052 | A1 | 3/2004 | Thomas et al. |

FOREIGN PATENT DOCUMENTS

| EP | 1 249 233 | 10/2002 |
| EP | 1 760 073 | 3/2007 |
| EP | 1 988 077 | 11/2008 |
| EP | 2 014 285 | 1/2009 |
| EP | 2 017 261 | 1/2009 |
| JP | 2001-122865 | 5/2001 |
| JP | 2003-096056 | 4/2003 |
| WO | 90/15057 | 12/1990 |
| WO | 96/16542 | 6/1996 |
| WO | 02/22592 | 3/2002 |
| WO | 02/49648 | 6/2002 |
| WO | 03/009845 | 2/2003 |
| WO | 2005/103018 | 11/2005 |
| WO | 2008/026563 | 3/2008 |

OTHER PUBLICATIONS

International Search Report issued Nov. 14, 2007 in the International (PCT) Application of which the present application is the U.S. National Stage.
L. Grundemar et al., "Neuropeptide Y effector systems: perspectives for drug development", TIPS, vol. 15, pp. 153-159, May 1994.
C. Betancur et al., "Nonpeptide antagonists of neuropeptide receptors: tools for research and therapy", TIPS, vol. 18, pp. 372-386, Oct. 1997.
A. A. Balasubramaniam et al., "Neuropeptide Y Family of Hormones: Receptor Subtypes and Antagonists", Peptides, vol. 18, No. 3, pp. 445-457, 1997.
Y. Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, pp. 466-472, Jan. 1988.
A. Inui et al., "Evidence for Further Heterogeneity of the Receptors for Neuropeptide-Y and Peptide-YY in Tumor Cell Lines Derived from Neural Crest", Endocrinology, vol. 131, No. 5, pp. 2090-2096, 1992.
C. Fotsch et al., "Synthesis and Structure-Activity Relationships of Trisubstituted Phenyl Urea Derivatives as Neuropeptide Y5 Receptor Antagonists", J. Med. Chem., vol. 44, No. 14, pp. 2344-2356, 2001.

(Continued)

*Primary Examiner* — Kamal Saeed
(74) *Attorney, Agent, or Firm* — Wenderoth, Lind & Ponack, L.L.P.

(57) ABSTRACT

Disclosed is a novel compound having an NPY Y5 receptor antagonistic activity.
A compound represented by the formula:

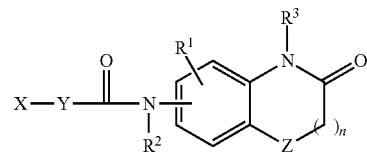

its pharmaceutically acceptable salt or solvate thereof, wherein
X is hydrogen or the like,
Y is a group of the formula:

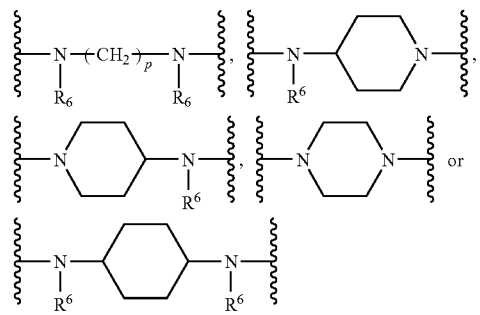

Z is —NR$^7$— or the like,
R$^1$ is hydrogen or the like,
R$^2$ and R$^3$ are each independently hydrogen or the like,
n is 0 or 1,
p is 0 to 6.

13 Claims, No Drawings

OTHER PUBLICATIONS

M. H. Block et al., "Discovery and Optimization of a Series of Carbazole Ureas as NPY5 Antagonists for the Treatment of Obesity", J. Med. Chem., vol. 45, No. 16, pp. 3509-3523, 2002.

J. Finn et al., "High-Throughput Synthesis Optimization of Sulfonamide NPY Y5 Antagonists", Bioorganic & Medicinal Chemistry Letters, vol. 12, No. 13, pp. 1771-1774, 2002.

S. J. Aquino et al., "Synthesis and Structure Activity Relationship of Guanidines as NPY Y5 Antagonists", Bioorganic & Medicinal Chemistry, vol. 12, No. 10, pp. 2691-2708, 2004.

Supplementary European Search Report dated Aug. 23, 2010 in Application No. EP 07 79 3051.

J. Branquet et al., "Synthese et activite physiologique de derives d'α-amino-acids, α-disubstitues (1, 2, 3)", Bulletin De La Societe Chimique De France, vol. 10, pp. 2942-2954, 1965.

UREA DERIVATIVE

This application is a U.S. national stage of International Application No. PCT/JP2007/066607 filed Aug. 28, 2007.

FIELD OF THE INVENTION

This invention relates to a novel compound having an NPY Y5, receptor antagonistic activity. The compound is useful as a pharmaceutical composition, especially as an anti-obesity drug.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulatory action on food intake, an anti-seizure activity, a learning-enhancing action, an anti-anxiety activity, an anti-stress activity, etc. in the central nervous system, and it may be pivotally involved in central nervous system diseases such as depression, Alzheimer's disease, Parkinson's disease. NPY is thought to be involved in cardiovascular diseases, since it induces a contraction of smooth muscles such as blood vessels or cardiac muscles in peripheral tissues. Furthermore, NPY is also known to be involved in metabolic diseases such as obesity, diabetes, hormone abnormalities (Non-patent Document 1). Therefore, an NPY receptor antagonist is expected as medicine for preventing or treating the above-mentioned various diseases associated with the NPY receptor.

Six subtypes of NPY receptors have now been identified: Y1, Y2, Y3, Y4, Y5, and Y6 (Non-patent Document 2). It has been suggested that the Y5 receptor is at least involved in the feeding behavior and its antagonist is expected as an anti-obesity drug (Non-patent Document 3).

Patent Documents 1 to 4 disclose urea derivatives having structures similar to those of compounds of the present invention and exhibiting an NPY Y5 receptor antagonistic activity, but do not disclose urea derivatives substituted with benzoxazolinone.

Patent Documents 5 to 7 disclose urea derivatives: Document 5, 6 and 7 disclose N-(3,4-dihydro-3-oxo-2H-1,4-benzoxazin-6-yl)-N'-[2-[ethyl(3-methylphenyl)amino]ethyl]-urea, N-[3-(diethylamino)propyl]-N'-(2,3-dihydro-2-oxo-1H-benzimidazol-5-yl)-urea and N,N''-1,6-hexanediylbis[N'-(2,3-dihydro-2-oxo-6-benzoxazolyl)]-urea, respectively. None of these documents, however, refer to an NPY Y5 receptor antagonistic activity.

[Non-patent Document 1] Trends in Pharmacological Sciences 1994; 15: 153
[Non-patent Document 2] Trends in Pharmacological Sciences 1997; 18: 372
[Non-patent Document 3] Peptides 1997; 18: 445
[Patent Document 1] WO01/037826
[Patent Document 2] JP2001-122865
[Patent Document 3] WO02/022592
[Patent Document 4] WO02/049648
[Patent Document 5] WO05/103018
[Patent Document 6] JP03/096056
[Patent Document 7] EP45892

DISCLOSURE OF INVENTION

Problems to be Solved by the Invention

The present invention provides novel compounds having a strong NPY Y5 receptor antagonistic activity.

Means for Solving the Problem

The present invention includes:
(1) A compound of the formula (I):

[Formula 1]

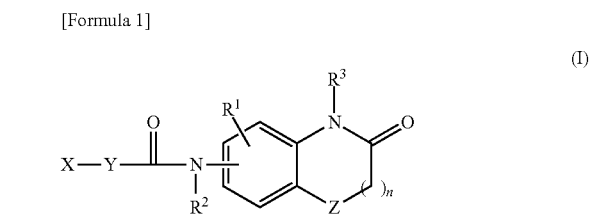

(I)

its pharmaceutically acceptable salt or solvate thereof, wherein

X is hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy, optionally substituted alkoxycarbonyl, optionally substituted aryloxy, optionally substituted aryloxycarbonyl, optionally substituted alkylthio, optionally substituted arylthio, —S(O)m-$R^4$, —C(=O)$R^4$, —C(=S)NR$^4$R$^5$ or —C(=O)NR$^4$, R$^5$, Y is a group of the formula:

[Formula 2]

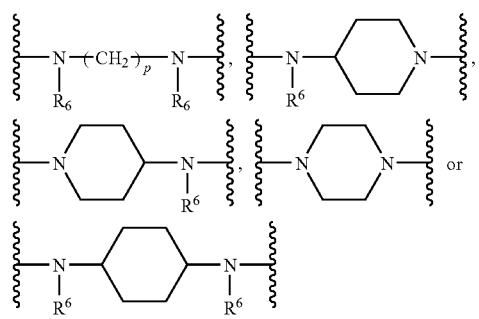

Z is —O— or —NR$^7$—, $R^1$ is hydrogen, carboxy, hydroxy, nitro, halogen, cyano, mercapto, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy, optionally substituted alkoxycarbonyl, optionally substituted aryloxy, optionally substituted aryloxycarbonyl, optionally substituted alkylthio, optionally substituted arylthio, optionally substituted carbamoyl, optionally substituted thiocarbamoyl, optionally substituted acyl or optionally substituted sulfamoyl, $R^4$ is hydrogen, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy or optionally substituted aryloxy, provided that when X is —S(O)$_m$—R$^4$, R$^4$ is not hydrogen, $R^2$, $R^3$, $R^5$, $R^6$ and $R^7$ are each independently hydrogen, hydroxy, optionally substituted alkyl or optionally substituted acyl, m is 1 or 2, n is 0 or 1, p is 0 to 6, provided that N-(3,4-dihydro-3-oxo-2H-1,4-benzoxazin-6-yl)-N'-[2-[ethyl(3-methylphenyl)amino]ethyl]-urea, N-[3-(diethylamino)propyl]-N'-(2,3-dihydro-2-oxo-1H-benzimidazol-5-yl)-urea and N,N"-1,6-hexanediylbis[N'-(2,3-dihydro-2-oxo-6-benzoxazolyl)]-urea are excluded.

(2) The compound of the above (1), its pharmaceutically acceptable salt or solvate thereof, wherein a group of the formula (I):

[Formula 3]

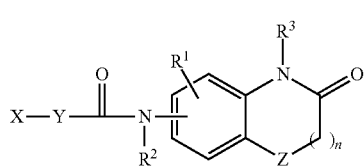

(I)

is a group of the formula (II):

[Formula 4]

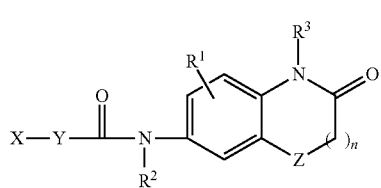

(II)

(3) The compound of the above (1) or (2), its pharmaceutically acceptable salt or solvate thereof, wherein Y is a group of the formula:

[Formula 5]

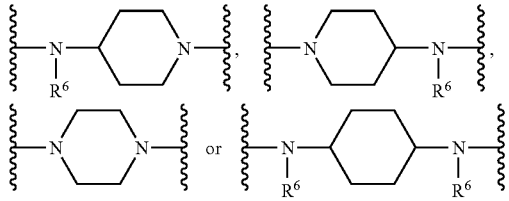

wherein $R^6$ has the same meaning as defined in the above (1).

(4) The compound of the above (3), its pharmaceutically acceptable salt or solvate thereof, wherein $R^6$ is hydrogen or optionally substituted alkyl.

(5) The compound of any one of the above (1) to (4), its pharmaceutically acceptable salt or solvate thereof, wherein Z is —O—.

(6) The compound of any one of the above (1) to (5), its pharmaceutically acceptable salt or solvate thereof, wherein n is 0.

(7) The compound of any one of the above (1) to (6), its pharmaceutically acceptable salt or solvate thereof, wherein X is —S(O)$_m$—R$^4$ (m is 2), —C(=O)R$^4$, —C(=S)NR$^4$R$^5$ or —C(=O)NR$^4$, R$^5$ (R$^4$ and R$^5$ have the same meaning as defined in the above (1)).

(8) The compound of the above (7), its pharmaceutically acceptable salt or solvate thereof, wherein $R^4$ is optionally substituted alkyl or optionally substituted cycloalkyl.

(9) The compound of the above (7), its pharmaceutically acceptable salt or solvate thereof, wherein $R^5$ is hydrogen or optionally substituted alkyl.

(10) The compound of any one of the above (1) to (9), its pharmaceutically acceptable salt or solvate thereof, wherein $R^1$ is hydrogen, halogen or optionally substituted alkyl.

(11) The compound of any one of the above (1) to (10), its pharmaceutically acceptable salt or solvate thereof, wherein $R^2$ is hydrogen.

(12) The compound of any one of the above (1) to (11), its pharmaceutically acceptable salt or solvate thereof, wherein $R^3$ is optionally substituted alkyl.

(13) The compound of the above (12), its pharmaceutically acceptable salt or solvate thereof, wherein $R^3$ is isopropyl.

(14) A pharmaceutical composition comprising the compound of any one of the above (1) to (13), its pharmaceutically acceptable salt or solvate thereof.

(15) The pharmaceutical composition according to the above (14), which has an NPY Y5 receptor antagonistic activity.

(16) The pharmaceutical composition comprising the compound of any one of the above (1) to (13), its pharmaceutically acceptable salt or solvate thereof, which is used as an anorectic agent or an anti-obesity drug.

(17) A method for preventing or treating disorders associated with NPY Y5, comprising administrating the compound of any one of the above (1) to (13), its pharmaceutically acceptable salt or solvate thereof.

[18] A use of the compound of any one of the above (1) to (13), its pharmaceutically acceptable salt or solvate thereof for the manufacture of a therapeutic agent for disorders associated with NPY Y5.

[19] A compound of the formula (V):

[Formula 6]

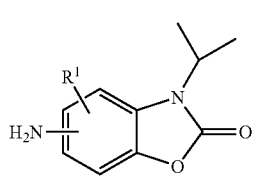

(V)

its pharmaceutically acceptable salt or solvate thereof, wherein $R^1$ has the same meaning as defined in the above (1).

Effect of the Invention

A compound of the present invention exhibits an NPY Y5 receptor antagonistic activity and is very useful as a medicine especially for preventing and/or treating disorders associated with NPY Y5, e.g. feeding disorder, obesity, hyperorexia, sexual disorder, impaired fertility, depression, epileptic seizure, hypertension, cerebral hemorrhage, congestive heart failure, sleep disorders, etc. and disorders for which obesity is a risk factor, e.g. diabetes, hypertension, hyperlipidemia, arteriosclerosis, acute coronary syndrome, etc.

BEST MODE FOR CARRYING OUT THE INVENTION

Terms used in the present description are explained below. Each term has the same meaning alone or together with other terms in this description.

"Halogen" includes fluorine, chlorine, bromine and iodine. Especially preferred is fluorine or chlorine.

"Alkyl" includes C1 to C10 straight or branched alkyl group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl and the like. Preferred is C1 to C6 or C1 to C4 alkyl. Examples include methyl, ethyl, n-propyl, isopropyl, n-butyl, isobutyl, sec-butyl, tert-butyl, n-pentyl, isopentyl, neopentyl, n-hexyl, isohexyl and the like.

"Alkyl" of $R^3$ is preferably C1 to C6, more preferably C1 to C4 and most preferably isopropyl.

"Alkyl" of $R^4$ is preferably C1 to C10, more preferably C1 to C7 and most preferably methyl, ethyl, n-propyl, isopropyl, n-butyl, s-butyl, t-butyl, 3-pentyl or cycloalkyl. As cycloalkyl, preferred is cyclopropyl, cyclobutyl, cyclopentyl or cyclohexyl.

"Alkyl" in other cases is preferably C1 to C10 and more preferably C1 to C6.

"Cycloalkyl" includes C3 to C15 saturated cyclic hydrocarbon group. Examples include cyclopropyl, cyclobutyl, cyclopentyl, cyclohexyl, cycloheptyl, cyclooctyl, bridged cyclic hydrocarbon group, spiro-hydrocarbon group and the like. Preferred is cyclopropyl, cyclobutyl, cyclopentyl, cyclohexyl or bridged cyclic hydrocarbon group.

"Bridged cyclic hydrocarbon group" includes a group which is derived by excluding one hydrogen atom from a C5 to C8 aliphatic cycle which consists of two rings that share two or more atoms. Examples include bicyclo[2.1.0]pentyl, bicyclo[2.2.1]heptyl, bicyclo[2.2.2]octyl, bicyclo[3.2.1]octyl, tricyclo[2.2.1.0]heptyl and the like.

"Spiro-hydrocarbon group" includes a group which is derived by excluding one hydrogen atom from a cycle which consists of two hydrocarbon rings that share one carbon atom. Examples include spiro[3.4]octyl and the like.

"Halogenated alkyl" includes alkyl substituted with one or more halogen atoms. The alkyl part and the halogen part of "halogenated alkyl" are the same as the above.

"Alkenyl" includes C2 to C8 straight or branched alkenyl group having one or more double bonds in the above "alkyl". Examples include vinyl, 1-propenyl, 2-propenyl, 1-butenyl, 2-butenyl, 3-butenyl, 1,3-butadienyl, 3-methyl-2-butenyl and the like.

"Cycloalkenyl" includes C3 to C7 cyclic unsaturated aliphatic hydrocarbon group. Examples include cyclopropenyl, cyclobutenyl, cyclopentenyl, cyclohexenyl, cycloheptenyl and the like. Preferred is cyclopropenyl, cyclobutenyl, cyclopentenyl or cyclohexenyl. Cycloalkenyl also includes those bridged cyclic hydrocarbon group and spiro-hydrocarbon group which have an unsaturated bond in the ring.

"Alkynyl" includes C2 to C8 straight or branched alkynyl group having one or more triple bonds in the above "alkyl". Examples include ethynyl, propynyl, butynyl and the like.

"Aryl" includes monocyclic aromatic hydrocarbon group (e.g., phenyl) and polycyclic aromatic hydrocarbon group (e.g., 1-naphtyl, 2-naphtyl, 1-anthryl, 2-anthryl, 9-anthryl, 1-phenanthryl, 2-phenanthryl, 3-phenanthryl, 4-phenanthryl or 9-phenanthryl). Preferred is phenyl or naphtyl (1-naphtyl or 2-naphtyl).

"Heteroaryl" means monocyclic aromatic heterocyclic group and fused aromatic heterocyclic group. The monocyclic aromatic heterocyclic group means a group derived from 5- to 8-membered aromatic ring which may contain 1 to 4 oxygen, sulfur and/or nitrogen atom(s) in the ring. The binding bond can be at any substitutable position. The fused aromatic heterocyclic group means a group derived from 5- to 8-membered aromatic ring which may contain 1 to 4 oxygen, sulfur and/or nitrogen atom(s) in the ring fused with one to four of 5- to 8-membered aromatic carbocycle(s) or other 5- to 8-membered aromatic heterocycle(s). The binding bond can be at any substitutable position.

"Heteroaryl" includes, for example, furyl (e.g., furan-2-yl or furan-3-yl), thienyl (e.g., thiophene-2-yl or thiophene-3-yl), pyrrolyl (e.g., pyrrole-1-yl, pyrrole-2-yl or 50 pyrrole-3-yl), imidazolyl (e.g., imidazole-1-yl, imidazole-2-yl or imidazole-4-yl), pyrazolyl (e.g., pyrazole-1-yl, pyrazole-3-yl or pyrazole-4-yl), triazolyl (e.g., 1,2,4-triazole-1-yl, 1,2,4-triazole-3-yl or 1,2,4-triazole-4-yl), tetrazolyl (e.g., tetrazole-1-yl, tetrazole-2-yl or tetrazole-5-yl), oxazolyl (e.g., oxazole-2-yl, oxazole-4-yl or oxazole-5-yl), isoxazolyl (e.g., isoxazole-3-yl, isoxazole-4-yl or isoxazole-5-yl), thiazolyl (e.g., thiazole-2-yl, thiazole-4-yl or thiazole-5-yl), thiadiazolyl, isothiazolyl (e.g., isothiazole-3-yl, isothiazole-4-yl or isothiazole-5-yl), pyridyl (e.g., pyridine-2-yl, pyridine-3-yl or pyridine-4-yl), pyridazinyl (e.g., pyridazine-3-yl or pyridazine-4-yl), pyrimidinyl (e.g., pyrimidine-2-yl, pyrimidine-4-yl or pyrimidine-5-yl), furazanyl (e.g., furazan-3-yl), pyrazinyl (e.g., pyrazine-2-yl), oxadiazolyl (e.g., 1,3,4-oxadiazole-2-yl), benzofuryl (e.g., benzo[b]furan-2-yl, benzo[b]furan-3-yl, benzo[b]furan-4-yl, benzo[b]furan-5-yl, benzo[b]furan-6-yl or benzo[b]furan-7-yl), benzothienyl (e.g., benzo[b]thiophene-2-yl, benzo[b]thiophene-3-yl, benzo[b]thiophene-4-yl, benzo[b]thiophene-5-yl, benzo[b]thiophene-6-yl or benzo[b]thiophene-7-yl), benzimidazolyl (e.g., benzimidazole-1-yl, benzimidazole-2-yl, benzimidazole-4-yl or benzimidazole-5-yl), dibenzofuryl, benzoxazolyl, benzothiazole, quinoxalyl (e.g., quinoxaline-2-yl, quinoxaltine-5-yl or quinoxaline-6-yl), cinnolinyl (e.g., cinnoline-3-yl, cinnoline-4-yl, cinnoline-5-yl, cinnoline-6-yl, cinnoline-7-yl or cinnoline-8-yl), quinazolyl (e.g., quinazoline-2-yl, quinazoline-4-yl, quinazoline-5-yl, quinazoline-6-yl, quinazoline-7-yl or quinazoline-8-yl), quinolyl (e.g., quinoline-2-yl, quinoline-3-yl, quinoline-4-yl, quinoline-5-yl, quinoline-6-yl, quinoline-7-yl or quinoline-8-yl), phthalazinyl (e.g., phthalazine-1-yl, phthalazine-5-yl or phthalazine-6-yl), isoquinolyl (e.g., isoquinoline-1-yl, isoquinoline-3-yl, isoquinoline-4-yl, isoquinoline-5-yl, isoquinoline-6-yl, isoquinoline-7-yl or isoquinoline-8-yl), puryl, pteridinyl (e.g., pteridine-2-yl, pteridine-4-yl, pteridine-6-yl or pteridine-7-yl), carbazolyl, phenanthridinyl, acridinyl (e.g., acridine-1-yl, acridine-2-yl, acridine-3-yl, acridine-4-yl or acridine-9-yl), indolyl (e.g., indole-1-yl, indole-2-yl, indole-3-yl, indole-4-yl, indole-5-yl, indole-6-yl or indole-7-yl), isoindolyl, phenazinyl (e.g., phenazine-1-yl or phenazine-2-yl), phenothiazinyl (e.g., phenothiazine-1-yl, phenothiazine-2-yl, phenothiazine-3-yl or phenothiazine-4-yl) or the like.

"Heterocycle" means a nonaromatic heterocycle group which may contain 1 to 4 oxygen, sulfur and/or nitrogen atom(s) in the ring. The binding bond can be at any substitutable position. Moreover, the nonaromatic heterocycle group can be bridged with a C1 to C4 alkyl chain or can be fused with cycloalkane (preferred is 5- to 6-membered ring) or benzene ring. Heterocycle can be saturated or unsaturated, as long as it is nonaromatic. Preferred is 5- to 8-membered ring. Exemplified is 1-pyrrolinyl, 2-pyrrolinyl, 3-pyrrolinyl, 1-pyrrolidinyl, 2-pyrrolidinyl, 3-pyrrolidinyl; 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl or the like.

The alkyl part of "alkoxy", "alkoxycarbonyl", "alkylsulfonyl", "alkylcarbonyl" and "alkylthio" means the above "alkyl".

The aryl part of "aryloxy", "aryloxycarbonyl", "arylsulfonyl", "arylcarbonyl" and "arylthio" means the above "aryl".

The heteroaryl part of "heteroarylcarbonyl", "heteroarylsulfonyl" and "heteroaryloxycarbonyl" means the above "heteroaryl".

The heterocycle part of "heterocycle carbonyl", "heterocycle sulfonyl" and "heterocycle oxycarbonyl" means the above "heterocycle".

The alkoxy part and the halogen part of "halogenated alkoxy" are the same as the above.

"Acyl" means formyl, optionally substituted alkylcarbonyl, optionally substituted alkenylcarbonyl, optionally substituted cycloalkylcarbonyl, optionally substituted cycloalkenylcarbonyl, optionally substituted arylcarbonyl, optionally substituted heteroarylcarbonyl or optionally substituted heterocyclecarbonyl.

"Aralkyl" means the above "alkyl" substituted with 1 to 3 of the above "aryl".

The aralkyl part of "aralkyl carbonyl" is the same as the above.

"Alkylene" includes a bivalent group comprising 1 to 6 of methylene. Exemplified is methylene, ethylene, trimethylene, tetramethylene, pentamethylene, hexamethylene or the like.

The alkylene part of "alkylene dioxy" is the same as the above "alkylene". Preferred is methylene dioxy or ethylene dioxy.

"Alkenylene" includes a bivalent group comprising 2 to 6 of methylene, containing at least one carbon-carbon double bond.

"Cycloalkylene" includes a bivalent group which is derived by excluding one hydrogen atom from the above "cycloalkyl".

"Cycloalkenylene" includes a group containing at least one double bond in the above cycloalkylene.

"Arylene" includes a bivalent group which is derived by excluding one hydrogen atom from the above "aryl".

"Heterocycle diyl" includes a bivalent group which is derived by excluding one hydrogen atom from the above "heterocycle". Preferred is piperidine diyl, piperazine diyl, pyridine diyl, pyrimidine diyl, pyrazine diyl, pyrrolidine diyl or pyrrole diyl. More preferred is piperidine diyl.

"Heteroarylene" refers to the above "heterocycle diyl" having aromatic character. Examples are pyrrole diyl, imidazole diyl, pyrazole diyl, pyridine diyl, pyridazine diyl, pyrimidine diyl, pyrazine diyl, triazole diyl, triazine diyl, isoxazole diyl, oxazole diyl, oxadiazole diyl, isothiazole diyl, thiazole diyl, thiadiazole diyl, furan diyl, thiophene diyl and the like.

"Optionally substituted alkyl", "optionally substituted alkenyl", "optionally substituted alkynyl", "optionally substituted cycloalkyl", "optionally substituted cycloalkenyl", "optionally substituted aryl", "optionally substituted heteroaryl", "optionally substituted heterocycle", "optionally substituted alkoxy", "optionally substituted alkoxycarbonyl", "optionally substituted aryloxy", "optionally substituted aryloxycarbonyl", "optionally substituted alkylthio", "optionally substituted arylthio", "optionally substituted acyl", "optionally substituted aralkylcarbonyl", "optionally substituted alkylsulfonyl", "optionally substituted arylsulfonyl", "optionally substituted alkylene", "optionally substituted alkylene dioxy", "optionally substituted alkenylene", "optionally substituted cycloalkylene", "optionally substituted cycloalkenylene", "optionally substituted arylene", "optionally substituted heterocycle diyl" and "optionally substituted heteroarylene" may be substituted with 1 to 4 substituent(s) selected from a group consisting of, for example, hydroxy, carboxy, halogen, halogenated alkyl (e.g.: $CF_3$, $CH_2CF_3$, $CH_2CCl_3$), alkyl (e.g.: methyl, ethyl, isopropyl, tert-butyl), alkenyl (e.g.: vinyl), alkynyl (e.g.: ethynyl), cycloalkyl (e.g.: cyclopropyl), cycloalkenyl (e.g.: cyclopropenyl), alkoxy (e.g.: methoxy, ethoxy, propoxy, butoxy), halogenated alkoxy (e.g.: $OCF_3$), alkenyloxy (e.g.: vinyloxy, allyloxy), alkoxycarbonyl (e.g.: methoxycarbonyl, ethoxycarbonyl, tert-butoxycarbonyl), nitro, nitroso, optionally substituted amino (e.g.: alkylamino (e.g.: methylamino, ethylamino, dimethylamino), acylamino (e.g.: acetylamino, benzoylamino), aralkylamino (e.g.: benzylamino, tritylamino), hydroxyamino, alkoxycarbonyl amino, alkylsulfonylamino, carbamoylamino, heterocyclecarbonylamino, arylsulfonylamino), azide, aryl (e.g.: phenyl), aralkyl (e.g.: benzyl), cyano, isocyano, isocyanate, thiocyanate, isothiocyanate, mercapto, alkylthio (e.g.: methylthio), alkylsulfonyl (e.g.: methanesulfonyl, ethanesulfonyl), optionally substituted carbamoyl (e.g.: alkylcarbamoyl (e.g.: methylcarbamoyl, ethylcarbamoyl, dimethylcarbamoyl), alkylsulfonylcarbamoyl), sulfamoyl, acyl (e.g.: formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azide, ureido, amidino, guanidino, phthalimide, oxo, heteroaryl, heterocycle, alkylene, alkylenedioxy ($—O—CH_2—O—$, $—O—CH_2—CH_2—O—$, $—O—CH_2—CH_2—CH_2—O—$, or the like), alkenylene, cycloalkylene, cycloalkenylene, arylene, heterocycle diyl, heteroarylene, heterocyclecarbonyl, aryloxy, aryloxycarbonyl, arylsulfonyl, arylthio and the like.

A substituent of "optionally substituted amino", "optionally substituted carbamoyl", "optionally substituted thiocarbamoyl" and "optionally substituted sulfamoyl" includes alkyl, alkenyl, aryl, heteroaryl, alkylcarbonyl, arylcarbonyl, heteroarylcarbonyl, heterocyclecarbonyl, alkoxycarbonyl, aryloxycarbonyl, heteroaryloxycarbonyl, heterocycleoxycarbonyl, sulfamoyl, alkylsulfonyl, carbamoyl, cycloalkylsulfonyl, arylsulfonyl, heteroarylsulfonyl, heterocyclesulfonyl, acyl, hydroxy, sulfinyl or the like.

The compounds of the present invention include any pharmaceutically acceptable salts thereof which can be produced. Examples of "the pharmaceutically acceptable salt" are salts with inorganic acid such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include any solvates thereof. Preferred is hydrate and any number of water molecules may be coordinated with the compound of the present invention.

When Compound (I) of the present invention has an asymmetric carbon atom, racemates, all of enantiomers and all of stereoisomers such as diastereomer, epimer and enantiomer thereof are within the scope of the present invention. When Compound (I) of the present invention having one or more double bonds forms an E isomer or Z isomer, both isomers are within the scope of the present invention. When Y has cycloalkylene as a part, both cis isomer and trans isomer are within the scope of the present invention. Especially preferred is a trans isomer.

For example, Compound (I) of the present invention can be prepared by the following methods. Each symbol has the same meaning as the above (1). In addition, the treatment of the conventional organic synthesis such as extraction, purification and the like can be used for the preparation of the compound of the present invention.

[Formula 7]

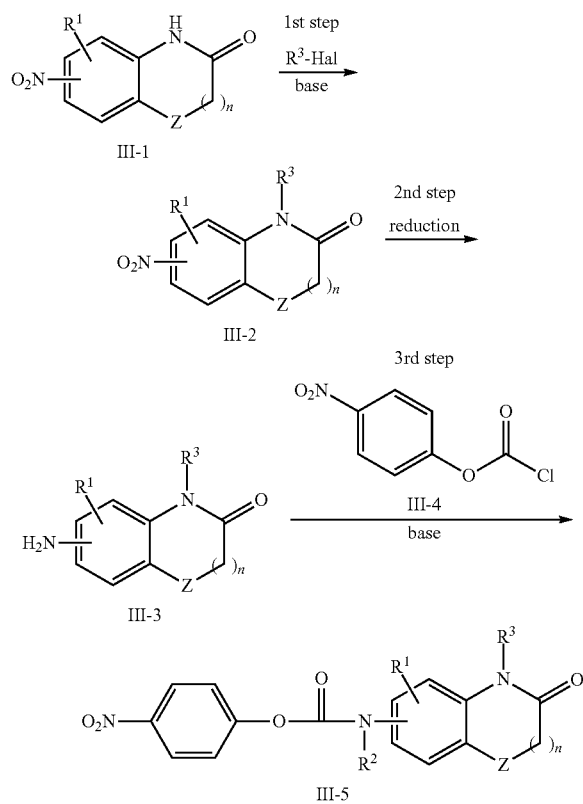

In the above scheme, Hal is halogen, and any other symbol has the same meaning as the above. As for Compound of the formula (III-1), known compounds or compounds derived from known compounds by conventional methods can be used.

1st Step

1st step is a process for preparing Compound of the formula (III-2) which comprises reacting Compound of the formula (III-1) with $R^3$-Hal in the presence of a base.

This reaction can be performed in a solvent of N-dimethyl formamide, dimethyl sulfoxide, aromatic hydrocarbons (for example, toluene, benzene, xylene or the like), saturated hydrocarbons (for example, cyclohexane, hexane or the like), halogenated hydrocarbons (for example, dichloromethane, chloroform, 1,2-dichloroethane or the like), ethers (for example, tetrahydrofuran, diethyl ether, dioxane, 1,2-dimethoxyethane or the like), esters (for example, methyl acetate, ethyl acetate or the like), ketones (for example, acetone, methyl ethylketone or the like), nitriles (for example, acetonitrile or the like), alcohols (for example, methanol, ethanol, t-butanol or the like), water, a mixed solvent thereof or the like. The base is, for example, metal hydrides (for example, sodium hydride or the like), metal hydroxides (for example, sodium hydroxide, potassium hydroxide, lithium hydroxide, barium hydroxide or the like), metal carbonates (for example, sodium carbonate, calcium carbonate, cesium carbonate or the like), metal alkoxides (for example, sodium methoxide, sodium ethoxide, potassium tert-butoxide or the like), sodium hydrogen carbonates, metallic sodiums, organic amines (for example, triethylamine, diisopropylethylamine, DBU, 2,6-lutidine, pyridine or the like) and pyridine. Preferably this reaction can be performed in a solvent of halogenated hydrocarbons (for example, dichloromethane, chloroform or the like), ethers (for example, tetrahydrofuran, diethyl ether, dioxane or the like) or N-dimethyl formamide, with metal hydrides (for example, sodium hydride or the like), metal alkoxides (for example, sodium methoxide, sodium ethoxide, potassium tert-butoxide or the like) or metal carbonates (for example, sodium carbonate, calcium carbonate, cesium carbonate or the like) as a base, in the presence of $R^3$-Hal within the range of $-30$ to $110°$ C. for 0.5 to 24 hours.

2nd Step

2nd step is a process for preparing Compound of the formula (III-3) which comprises reducing Compound of the formula (III-2).

This reaction can be performed by using a catalyst in an appropriate solvent under normal pressure or pressurization in atmosphere of hydrogen gas. As the solvent, the same solvent described in the above 1st step can be used. The catalyst is, for example, palladium/carbon, palladium hydroxide/carbon, palladium/alumina, palladium/barium carbonate, palladium/barium sulfate, palladium/calcium carbonate or the like. Preferably this reaction can be performed in a solvent of alcohols (for example, methanol, ethanol, t-butanol or the like), water, a mixed solvent thereof, or esters (for example, methyl acetate, ethyl acetate or the like), in the presence of palladium/carbon or the like, under normal pressure or pressurization in atmosphere of hydrogen gas, within the range of $-20$ to $50°$ C. for 0.5 to 24 hours.

3rd Step

3rd step is a process for preparing Compound of the formula (III-5) which comprises reacting Compound of the formula (III-3) with Compound of the formula (III-4). This reaction can be performed in an appropriate solvent in the presence of a base. As the solvent and base, the same solvent and base described in the above 1st step can be used. Preferably this reaction can be performed in a solvent of halogenated hydrocarbons (for example, dichloromethane, chloroform or the like) in the presence of an organic amine (for example, triethylamine, diisopropylethylamine, DBU, 2,6-lutidine, pyridine or the like) within the range of $-20$ to $50°$ C. for 0.5 to 24 hours.

[Formula 8]

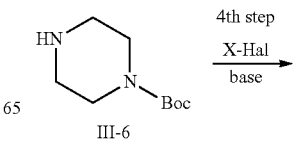

-continued

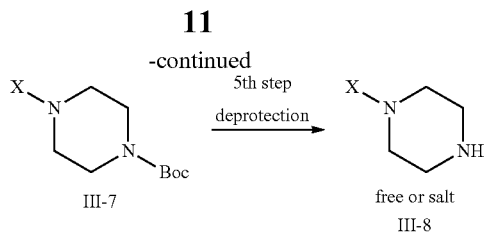

In the above scheme, Hal is halogen, Boc is t-butoxycarbonyl group, and any other symbol has the same meaning as the above. As for Compound of the formula (III-6), known compounds or compounds derived from known compounds by conventional methods can be used.

4th Step

4th step is a process for preparing Compound of the formula (III-7) which comprises reacting Compound of the formula (III-6) with X-Hal.

This reaction can be performed in an appropriate solvent in the presence of a base and X-Hal. As the solvent and base, the same solvent and base described in the above 1st step can be used. Preferably this reaction can be performed in a solvent of halogenated hydrocarbons (for example, dichloromethane, chloroform or the like) in the presence of an organic amine (for example, triethylamine, diisopropylethylamine, DBU, 2,6-lutidine, pyridine or the like) and X-Hal within the range of −50 to 50° C. for 0.5 to 24 hours.

5th Step

5th step is a process for preparing Compound of the formula (III-8) which comprises deprotecting the Boc-group of Compound of the formula (III-7).

This reaction can be performed in an appropriate solvent under an acidic condition. As the solvent, the same solvent described in the above 1st step can be used. Preferably this reaction can be performed in a solvent of ethers (for example, tetrahydrofuran, diethyl ether, dioxane, 1,2-dimethoxyethane or the like), esters (for example, methyl acetate, ethyl acetate or the like) or alcohols (for example, methanol, ethanol, t-butanol or the like) in the presence of hydrochloric acid or trifluoroacetic acid as acid catalyst within the range of −20 to 50° C. for 0.5 to 24 hours. The derived product may be in either salt or free-base form after neutralization.

[Formula 9]

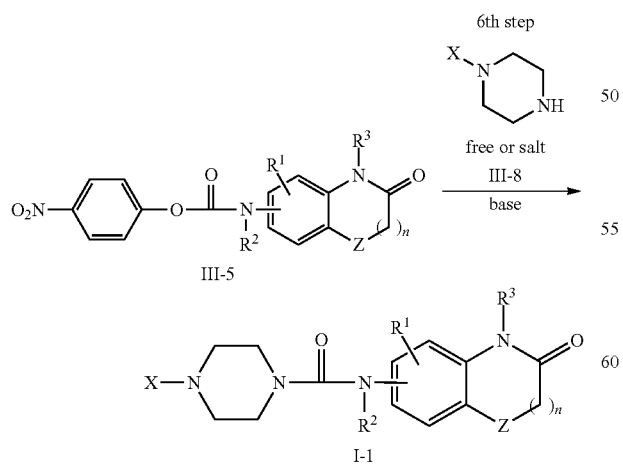

In the above scheme, each symbol has the same meaning as the above.

6th Step

6th step is a process for preparing Compound of the formula (I-1) which comprises reacting Compound of the formula (III-5) with Compound of the formula (III-8).

This reaction can be performed in an appropriate solvent in the presence of a base. As the solvent and base, the same solvent and base described in the above 1st step can be used. Preferably this reaction can be performed in a solvent of halogenated hydrocarbons (for example, dichloromethane, chloroform or the like) in the presence of an organic amine (for example, triethylamine, diisopropylethylamine, DBU, 2,6-lutidine, pyridine or the like) within the range of −20 to 50° C. for 0.5 to 24 hours.

[Formula 10]

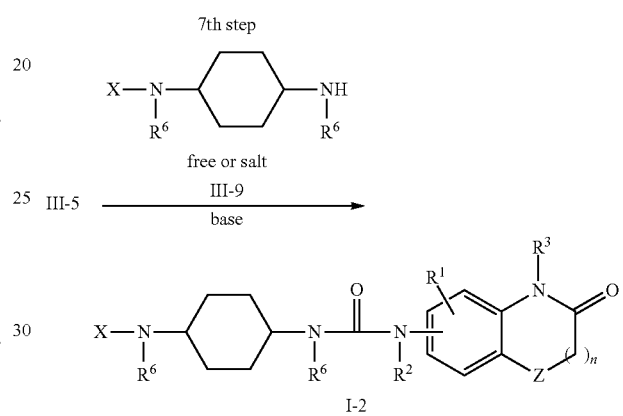

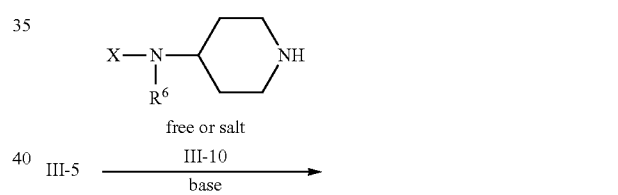

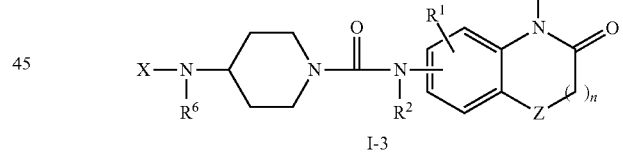

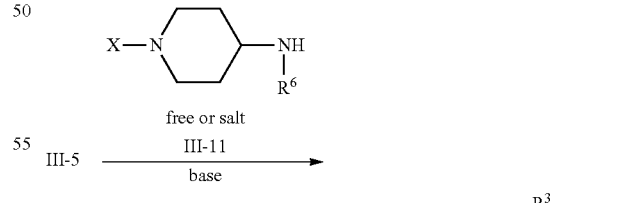

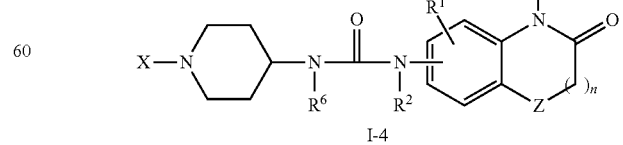

In the above scheme, each symbol has the same meaning as the above.

7th-9th Steps

7th-9th steps can be performed under the same conditions as the above 6th step. As for Compounds of the formulae (III-9), (III-10) and (III-11) used in these steps, known compounds or compounds derived from known compounds by conventional methods can be used.

used. Preferably this reaction can be performed in a solvent of aromatic hydrocarbons (for example, toluene, benzene, xylene or the like) in the presence of an organic amine (for example, triethylamine, diisopropylethylamine, DBU, 2,6-lutidine, pyridine or the like) and DPPA within the range of −20 to 110° C. for 0.5 to 24 hours.

[Formula 11]

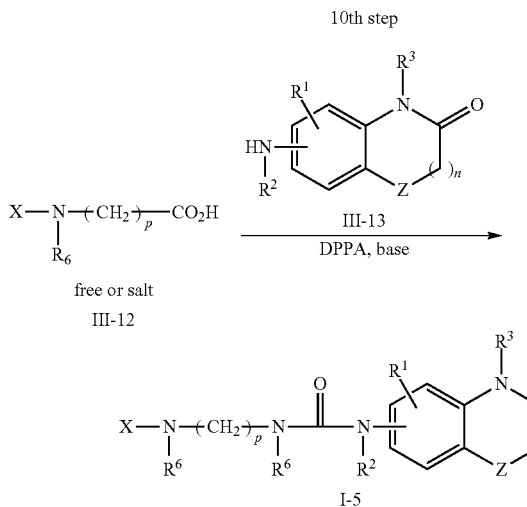

[Formula 12]

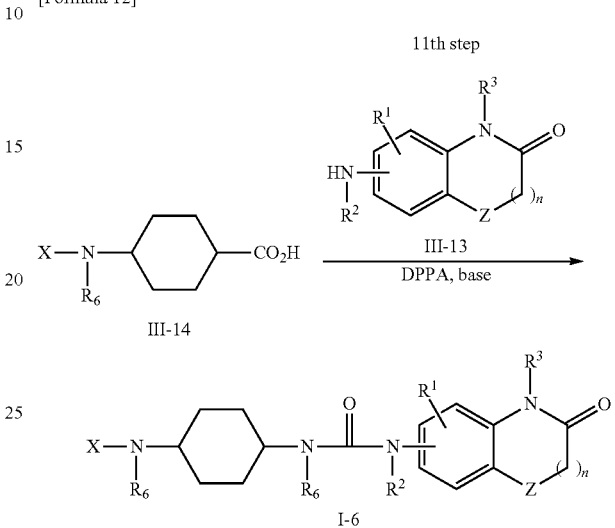

In the above scheme, each symbol has the same meaning as the above.

10th Step

10th step is a process for preparing Compound of the formula (I-5) which comprises reacting Compound of the formula (III-12) with Compound of the formula (III-13).

This reaction can be performed in an appropriate solvent in the presence of DPPA and a base. As the solvent and base, the same solvent and base described in the above 1st step can be In the above scheme, each symbol has the same meaning as the above.

11th Step

11th step can be performed under the same conditions as the above 10th step. As for Compound of the formula (III-14), known compounds or compounds derived from known compounds by conventional methods can be used.

[Formula 13]

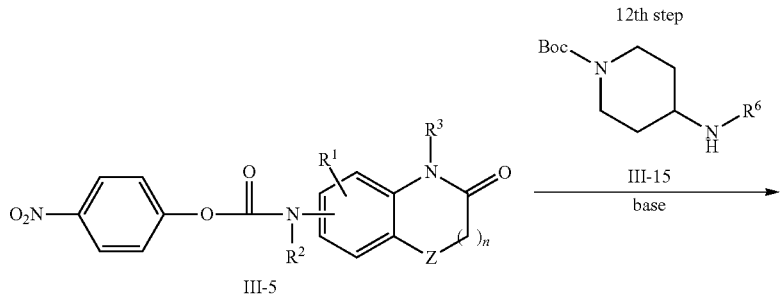

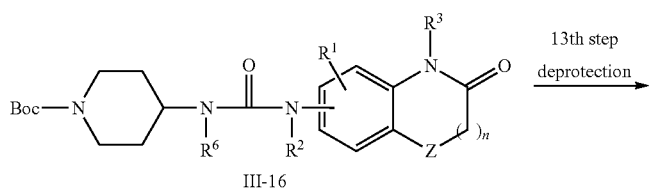

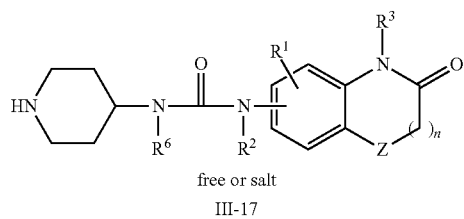

free or salt
III-17

-continued
14th step
X-Hal
base →

I-7

In the above scheme, Hal is halogen, Boc is t-butoxycarbonyl group, and any other symbol has the same meaning as the above. As for Compound of the formula (III-5), known compounds or compounds derived from known compounds by conventional methods can be used.

12th step

12th step is a process for preparing Compound of the formula (III-16) which comprises reacting Compound of the formula (III-5) with Compound (III-15).

This reaction can be performed in an appropriate solvent in the presence of a base. As the solvent and base, the same solvent and base described in the above 1st step can be used. Preferably this reaction can be performed in a solvent of halogenated hydrocarbons (for example, dichloromethane, chloroform or the like) in the presence of an organic amine (for example, triethylamine, diisopropylethylamine, DBU, 2,6-lutidine, pyridine or the like) within the range of −20 to 50° C. for 0.5 to 24 hours.

13th Step

13th step is a process for preparing Compound of the formula (III-17) which comprises deprotecting the Boc-group of Compound of the formula (III-16).

This reaction can be performed in an appropriate solvent under an acidic condition. As the solvent, the same solvent described in the above 1st step can be used. Preferably this reaction can be performed in a solvent of ethers (for example, tetrahydrofuran, diethyl ether, dioxane, 1,2-dimethoxyethane or the like), esters (for example, methyl acetate, ethyl acetate or the like) or alcohols (for example, methanol, ethanol, t-butanol or the like) in the presence of hydrochloric acid or trifluoroacetic acid as acid catalyst within the range of −20 to 50° C. for 0.5 to 24 hours. The derived product may be in either salt or free-base form after neutralization.

14th Step

14th step is a process of preparing Compound of the formula (I-7) which comprises reacting Compound of the formula (III-17) with X-Hal.

This reaction can be performed in an appropriate solvent in the presence of a base. As the solvent and base, the same solvent and base described in the above 1st step can be used. Preferably this reaction can be performed in a solvent of halogenated hydrocarbons (for example, dichloromethane, chloroform or the like) in the presence of an organic amine (for example, triethylamine, diisopropylethylamine, DBU, 2,6-lutidine, pyridine or the like) within the range of −20 to 50° C. for 0.5 to 24 hours.

As an intermediate of the present compound, especially useful is a compound of the formula (V):

[Formula 14]

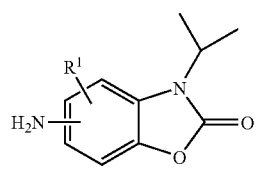

(V)

its pharmaceutically acceptable salt or solvate thereof,
wherein $R^1$ has the same meaning as the above (1).

Especially preferred is a compound of the formula (VI):

[Formula 15]

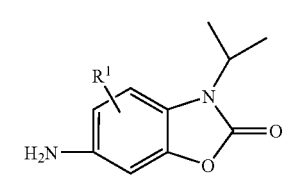

(VI)

its pharmaceutically acceptable salt or solvate thereof,
wherein $R^1$ has the same meaning as the above (1).

As $R^1$, especially preferred among the above (1) is hydrogen, carboxy, hydroxy, nitro, halogen, optionally substituted alkyl, optionally substituted amino or optionally substituted alkoxy.

All of the compounds of the present invention have an NPY Y5 receptor antagonistic activity. Especially preferred compounds include the following:

In the formula (I),

X is optionally substituted alkyl, optionally substituted cycloalkyl, optionally substituted aryl, optionally substituted heteroaryl, —S(O)$_m$—R$^4$, —C(=O)R$^4$, —C(=S)NR$^4$, R$^5$, —C(=O)NR$^4$, R$^5$ or the like. Especially preferred X is —S(O)$_m$—R$^4$, —C(=O)R$^4$ or —C(=S)NR$^4$R$^5$.

Y is a group of the formula:

[Formula 16]

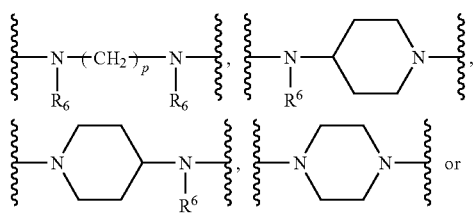

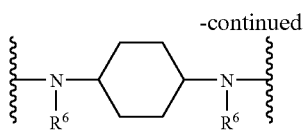

Especially preferred Y is a group of the formula:

[Formula 17]

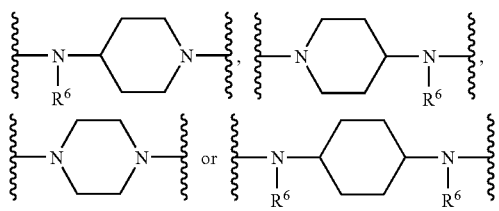

Z is —O—, —NR$^7$— or the like, and especially preferred Z is —O—.

R$^1$ is hydrogen, carboxy, hydroxy, nitro, halogen, cyano, optionally substituted alkyl, optionally substituted cycloalkyl, optionally substituted aryl, optionally substituted heteroaryl, optionally substituted heterocycle, optionally substituted amino, optionally substituted alkoxy, optionally substituted aryloxy or the like. Especially preferred R$^1$ is hydrogen, carboxy, hydroxy, nitro, halogen, optionally substituted alkyl, optionally substituted amino or optionally substituted alkoxy.

R$^4$ is hydrogen, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy, optionally substituted aryloxy or the like, provided that when X is —S(O)$_m$—R$^4$, R$^4$ is not hydrogen.
Especially preferred R$^4$ is optionally substituted alkyl or optionally substituted cycloalkyl.

R$^2$, R$^3$, R$^5$, R$^6$ and R$^7$ are each independently hydrogen, hydroxy, optionally substituted alkyl, optionally substituted acyl or the like. Especially preferred R$^2$, R$^3$, R$^5$, R$^6$ and R$^7$ are each independently hydrogen or optionally substituted alkyl.

m is 1 or 2, and especially preferred is 2.

n is 0 or 1, and especially preferred is 0.

p is 0 to 6, and especially preferred is 4.

The NPY Y5 receptor antagonist of the present invention is effective for all of the disorders associated with NPY Y5, and especially effective for preventing and/or treating obesity as well as for suppressing food intake. Also the NPY Y5 receptor antagonist of the present invention is effective for preventing and/or treating disorders for which obesity is a risk factor, such as diabetes, hypertension, hyperlipidemia, arteriosclerosis, acute coronary syndrome and the like. The NPY Y5 receptor antagonist of the present invention can be administered combinationally with other drugs for the above disorders and can be used as a combination formulation for the above disorders.

In addition, the NPY Y5 receptor antagonist of the present invention has a low affinity for NPY Y1 and Y2 receptors, and has a high selectivity for NPY Y5 receptor. NPY has a sustained vasoconstrictive effect on the periphery and this effect is expressed mainly via Y1 receptor. Since Y5 receptor is not involved in this effect at all, the NPY Y5 receptor antagonist has a low risk of inducing side effects due to the peripheral vasoconstriction, and is expected to be used as a safe medicine.

The NPY Y5 receptor antagonist shows an anti-obesity effect by suppressing food intake. Therefore, it is one of the features of the present antagonist not to induce side effects such as dyspepsia caused by an anti-obesity agent which inhibits digestion and absorption, or central nervous system side-effects such as an antidepressant effect due to a serotonin transporter inhibitor that shows an anti-obesity effect.

As an anti-obesity agent or anorectic agent, the compound of the present invention can be administered orally and parenterally. In the case of oral administration, it may be in any usual dosage form such as tablets, granules, powders, capsules, pills, solutions, syrups, buccal tablets and sublingual tablets. In the case of parenteral administration, any usual dosage form is acceptable, for example, injections (e.g., intravenous, intramuscular), suppositories, endermic agents and inhalations. The compound of the present invention is well absorbed orally and therefore, suitably administered in an oral dosage form.

A pharmaceutical composition may be manufactured by mixing an effective amount of the compound of the present invention with various pharmaceutical additives suitable for the dosage form, such as excipients, binders, moistening agents, disintegrants, lubricants and diluents. When the composition is of an injection, an active ingredient can be sterilized together with a suitable carrier to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrants include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose or the like may be used as base materials of suppositories. When the composition is prepared as solutions, emulsified injections or suspended injections, solubilizing agents, suspending agents, emulsifiers, stabilizers, preservatives, isotonic agents and the like which are usually used may be added. For oral preparation, sweetening agents, flavors and the like which are usually used may be added.

The dosage of a compound of the present invention as an anti-obesity agent or an anorectic agent should be determined in consideration of the patient's age and body weight, the type and degree of diseases, the administration route and the like. A usual oral dosage for an adult is 0.05 to 100 mg/kg/day and preferably 0.1 to 10 mg/kg/day. For parenteral administration, although the dosage highly depends on the administration route, a usual dosage is 0.005 to 10 mg/kg/day and preferably 0.01 to 1 mg/kg/day. The daily dose may be administered once a day or in several divided doses.

The present invention is further explained by the following Examples, which are not intended to limit the scope of the present invention.

Reference Example 1

[Formula 18]

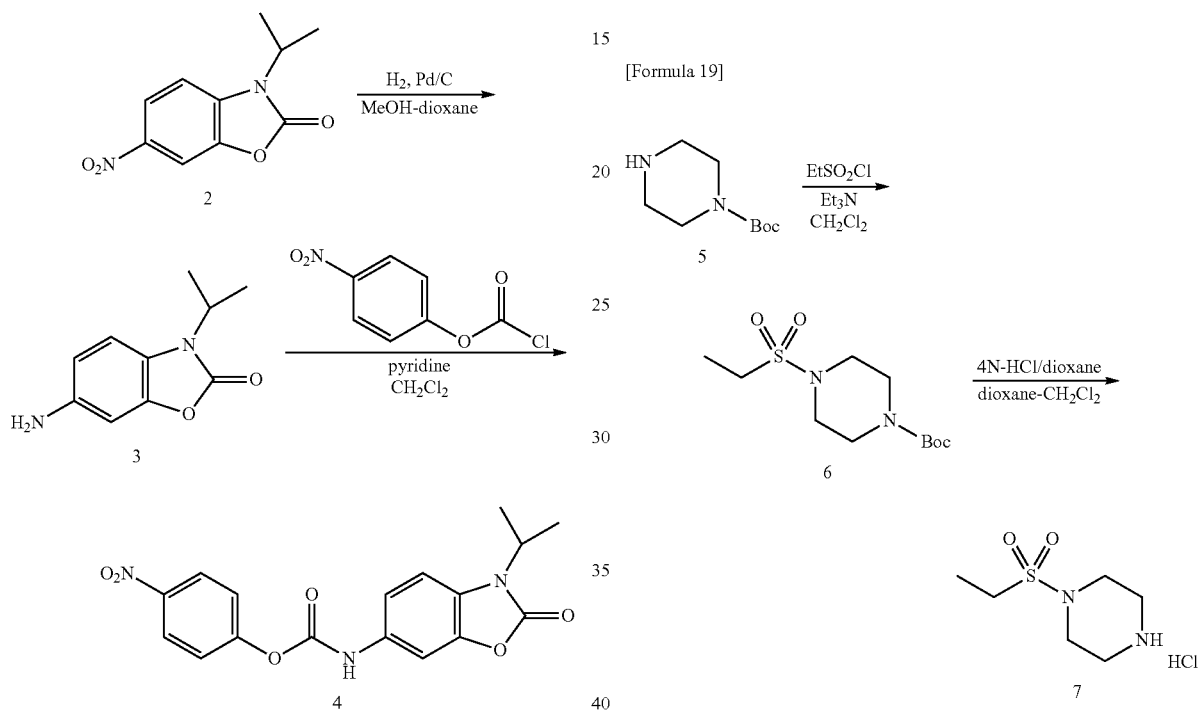

Commercial 6-Nitrobenzoxazole-2(3H)-one (Compound 1) (15 g, 83.28 mmol) was dissolved in DMF (200 mL), then to the reaction mixture, which was stirred at room temperature, were added potassium carbonate (23.02 g, 166 mmol) and 2-bromopropane (10.2 mL, 108 mmol). The whole mixture was stirred on heating at 90° C. for 4 hours, poured into water and extracted with ethyl acetate. The extract was washed with water and saturated saline successively, then dried with anhydrous sodium sulfate. Ethyl acetate was removed under reduced pressure to give a solid crude product. The solid crude product was washed with diisopropylether to give Compound 2 (16.2 g, 88%). The obtained nitro compound (Compound 2) (16 g, 72 mmol) was dissolved in the mixed solvent made of methanol (200 mL) and dioxane (200 mL), then to the reaction mixture was added 10% palladium-carbon (5.0 g) and the whole mixture was stirred under hydrogen atmosphere for 6 hours. The catalyst was filtered and the solvent was removed under reduced pressure to give amine derivative (Compound 3) (14.2 g, 99%). The obtained amine derivative (Compound 3) (4.2 g, 21.85 mmol) was dissolved in dichloromethane (60 mL), and to the reaction mixture, which was stirred at 0° C., were added pyridine (3.45 g, 43.70 mmol) and 4-nitrophenyl chloroformate (4.4 g, 21.85 mmol). The whole mixture was warmed up to room temperature and stirred for 6 hours. To the whole mixture was added diisopropylether (200 mL), then the resulting crystallized solid was filtered to give Compound 4 (9.2 g, 89%).

4 $^1$H-NMR (DMSO-$d_6$) δ: 1.45 (s, 3H), 1.47 (s, 3H), 4.34-4.55 (m, 1H), 7.29 (d, 1H, J=8.4 Hz), 7.41 (d, 1H, J=8.4 Hz), 8.03 (t, 1H, J=5.4 Hz), 8.48-8.64 (m, 1H), 8.91 (d, 1H, J=5.4 Hz).

Reference Example 2

[Formula 19]

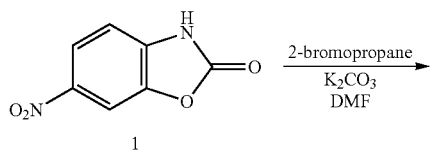

Commercial 1-Boc-piperazine (Compound 5) (3.0 g, 16.11 mmol) was dissolved in methylene chloride (30 mL), then to the reaction mixture, which was stirred at −40° C., were added triethylamine (5.61 mL, 40.28 mmol) and ethane sulfonyl chloride (1.83 mL, 19.33 mmol). The whole mixture was warmed up gradually and stirred for 14 hours. The whole mixture was poured into water and extracted with ethyl acetate. The organic layer of the extract was washed with dilute hydrochloric acid and saturated saline successively, then dried with sodium sulfate. The solvent was removed under reduced pressure and the residue was purified with silica-gel column chromatography to give ethane sulfonyl derivative (Compound 6) (3.82 g, 85%). Compound 6 (3.82 g, 13.72 mmol) was dissolved in the mixed solvent made of dioxane (5 mL) and methylene chloride (5 mL), then to the reaction mixture, which was stirred at room temperature, was added 4N hydrochloric acid (dioxane solvent) (8.58 mL, 34.31 mmol). The whole mixture was stirred at room temperature for 15 hours, then the resulting crystallized solid was filtered to give Compound 7 (2.76 g, 94%).

$^1$H-NMR (DMSO-$d_6$) δ: 1.22 (t, 3H, J=7.2 Hz), 3.06-3.22 (m, 6H), 3.414-3.3.52 (m, 4H), 9.59 (brs, 1H).

Example 1

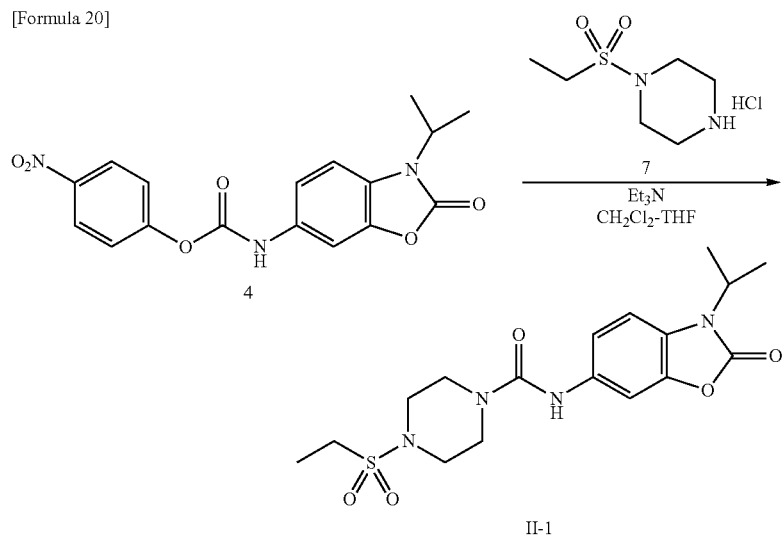

Compound 4 (450 mg, 1.26 mmol) and Compound 7 (280 mg, 1.30 mmol) were dissolved in the mixed solvent made of methylene chloride (7 mL) and THF (7 mL). To the reaction mixture, which was stirred at room temperature, was added triethylamine (0.44 mL, 3.15 mmol), and the whole mixture was stirred for 17 hours. The solvent of the whole mixture was removed under reduced pressure, then the residue was dissolved in ethyl acetate and washed with 2N sodium hydroxide solution and water successively. The reaction mixture was dried with sodium sulfate, then the solvent was removed. The resulting crude product was recrystallized with ethyl acetate and diisopropylether to give Compound II-1 (335 mg, 64%).

$^1$H-NMR (DMSO-$d_6$) δ: 1.23 (t, 3H, J=7.5 Hz), 1.43 (s, 3H), 1.46 (s, 3H), 3.09 (m, 2H), 3.15-3.26 (m, 4H), 3.45-3.60 (m, 4H), 4.34-4.52 (m, 1H), 7.16-7.25 (m, 2H), 7.53 (s, 1H), 8.70 (s, 1H).

The following examples were prepared by the same method.

Example 2

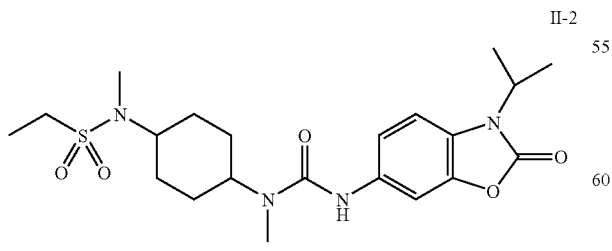

$^1$H-NMR (DMSO-$d_6$) δ: 1.14-1.22 (m, 2H), 1.36-2.00 (m, 12H), 2.64-3.15 (m, 7H), 3.20-4.19 (m, 6H), 4.31-4.52 (m, 1H), 7.15-7.28 (m, 2H), 7.53 (s, 1H), 8.26 (s, 1H).

Example 3

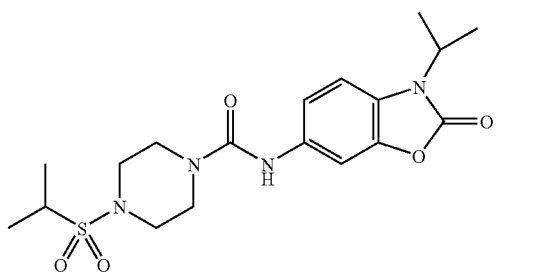

$^1$H-NMR (DMSO-$d_6$) δ: 1.23 (s, 3H), 1.25 (s, 3H), 1.43 (s, 3H), 1.46 (s, 3H), 3.18-3.43 (m, 5H), 3.45-3.54 (m, 4H), 4.36-4.51 (m, 1H), 7.16-7.34 (m, 2H), 7.55 (s, 1H), 8.68 (s, 1H).

Example 4

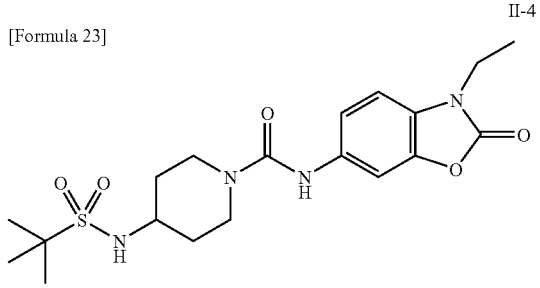

$^1$H-NMR (DMSO-$d_6$) δ: 1.20-1.58 (m, 13H), 1.79-1.92 (m, 2H), 2.86 (t, 2H, J=11.7 Hz), 3.21-3.38 (m, 2H), 3.78 (m,

2H), 3.93-4.09 (m, 2H), 6.89 (d, 1H, J=8.7 Hz), 7.12-7.26 (m, 2H), 7.53 (s, 1H), 8.57 (s, 1H).
(m, 2H), 3.88-4.19 (m, 2H), 4.30-4.54 (m, 1H), 7.07-7.35 (m, 3H), 7.54 (s, 1H), 8.58 (s, 1H).
Example 5
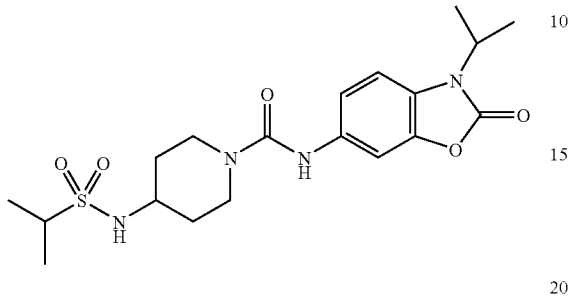
¹H-NMR (DMSO-d₆) δ: 1.22 (s, 3H), 1.24 (s, 3H), 1.31-1.40 (m, 2H), 1.43 (s, 3H), 1.45 (s, 3H), 1.76-1.95 (m, 2H), 2.79-3.08 (m, 2H), 3.11-3.22 (m, 1H), 3.82-4.18 (m, 2H), 4.35-4.56 (m, 1H), 7.04-7.40 (m, 3H), 7.54 (s, 1H), 8.59 (s, 1H).
Example 6
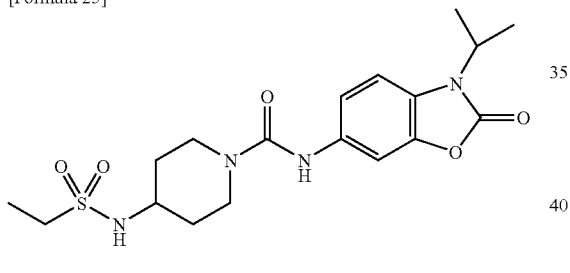
¹H-NMR (DMSO-d₆) δ: 1.21 (t, 3H, J=7.5 Hz), 1.27-1.41 (m, 2H), 1.43 (s, 3H), 1.46 (s, 3H), 1.75-1.90 (m, 2H), 2.90 (t, 2H, J=11.9 Hz), 3.03 (m, 2H), 3.24-3.38 (m, 1H), 3.94-4.09 (m, 2H), 4.32-4.55 (m, 1H), 7.10-7.33 (m, 3H), 7.54 (s, 1H), 8.59 (s, 1H).
Example 7
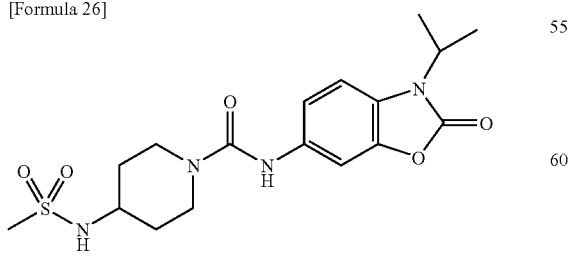
¹H-NMR (DMSO-d₆) δ: 1.16-1.40 (m, 2H), 1.43 (s, 3H), 1.45 (s, 3H), 1.74-1.96 (m, 2H), 2.80-3.03 (m, 4H), 3.22-3.46
Example 8
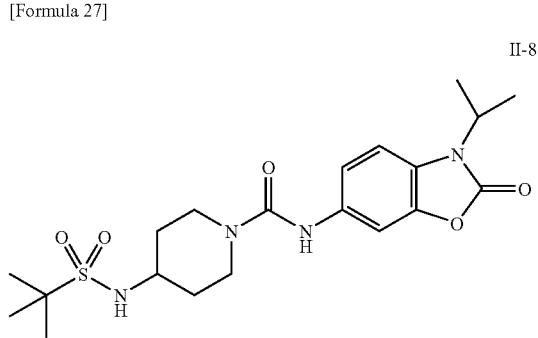
¹H-NMR (DMSO-d₆) δ: 1.28 (s, 9H), 1.32-1.41 (m, 2H), 1.43 (s, 3H), 1.45 (s, 3H), 1.79-1.94 (m, 2H), 2.86 (t, 2H, J=12.0 Hz), 3.21-3.38 (m, 1H), 3.92-4.14 (m, 2H), 4.36-4.50 (m, 1H), 6.89 (d, 1H, J=8.7 Hz), 7.13-7.32 (m, 2H), 7.53 (s, 1H), 8.57 (s, 1H).
Example 9
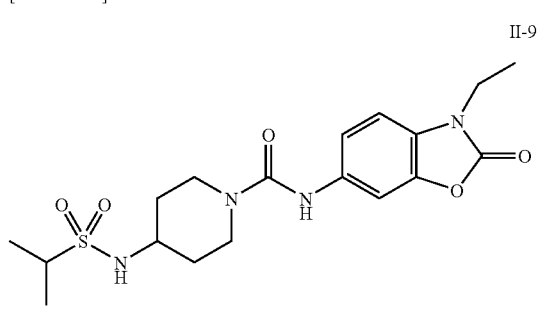
¹H-NMR (DMSO-d₆) δ: 1.22 (s, 3H), 1.24 (s, 3H), 1.26-1.50 (m, 3H), 1.74-1.90 (m, 2H), 2.80-2.97 (m, 2H), 3.08-3.24 (m, 2H), 3.26-3.36 (m, 1H), 3.74-3.88 (m, 3H), 3.92-4.10 (m, 2H), 7.05-7.28 (m, 3H), 7.54 (s, 1H), 8.59 (s, 1H).
Example 10
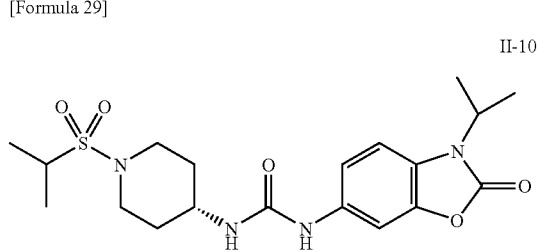
¹H-NMR (DMSO-d₆) δ: 1.21 (s, 3H), 1.23 (s, 3H), 1.28-1.39 (m, 2H), 1.43 (s, 3H), 1.45 (s, 3H), 1.79-1.92 (m, 2H), 3.04 (t, 2H, J=10.8 Hz), 3.24-3.34 (m, 1H), 3.46-3.74 (m, 3H), 4.33-4.52 (m, 1H), 6.23 (d, 1H, J=7.8 Hz), 7.01 (dd, 1H, J=8.4, 1.8 Hz), 7.26 (d, 1H, J=8.4 Hz), 7.58 (d, 1H, J=1.8 Hz), 8.43 (s, 1H).

Example 11

[Formula 30]

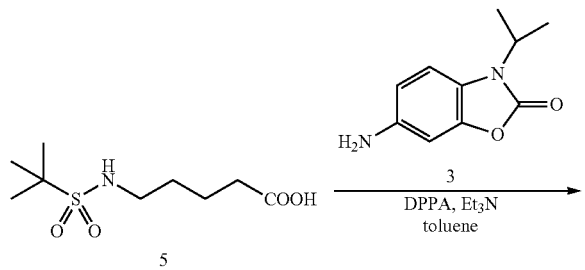

Carboxylic acid (Compound 5) (520 mg, 2.19 mmol) as a staring material and DPPA (0.47 mL, 2.19 mmol) were dissolved in toluene (8 mL), then to the reaction mixture, which was stirred at room temperature, was added triethylamine (0.31 mL, 2.19 mmol). The whole mixture was stirred at 90° C. for 3.5 hours, then cooled down to room temperature, and into the mixture was titrated the solution in which amine (Compound 3) (350 mg, 1.82 mmol) was dissolved in methylene chloride (8 mL). The reaction mixture was stirred at 65° C. for 2 hours, then poured into water and extracted with ethyl acetate. The organic layer of the extract was washed with water, dried with magnesium sulfate and purified with silica-gel column chromatography to give Compound II-11 (620 mg, 80%).

$^1$H-NMR (DMSO-$d_6$) δ: 1.26 (s, 9H), 1.40-1.70 (m, 10H), 2.92-3.18 (m, 4H), 4.33-4.52 (m, 1H), 6.12 (t, 1H, J=5.7 Hz), 6.87 (t, 1H, J=5.7 Hz), 7.00 (d, 1H, J=8.7 Hz), 7.24 (d, 1H, J=8.4 Hz), 7.58 (s, 1H), 8.48 (s, 1H).

The following examples were prepared by the same method.

Example 12

[Formula 31]

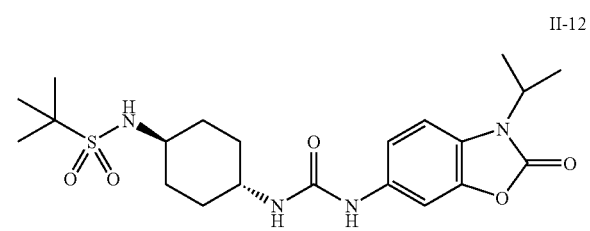

$^1$H-NMR (DMSO-$d_6$) δ: 1.05-1.25 (m, 2H), 1.26 (s, 9H), 1.27-1.41 (m, 2H), 1.42 (s, 3H), 1.44 (s, 3H), 1.79-1.99 (m, 4H), 2.98-3.16 (m, 1H), 3.24-3.41 (m, 1H), 4.36-4.48 (m, 1H), 6.00 (d, 1H, J=7.8 Hz), 6.76 (d, 1H, J=8.7 Hz), 6.97 (d, 1H, J=8.7 Hz), 7.23 (d, 1H, J=8.4 Hz), 7.56 (s, 1H), 8.40 (s, 1H).

Example 13

[Formula 32]

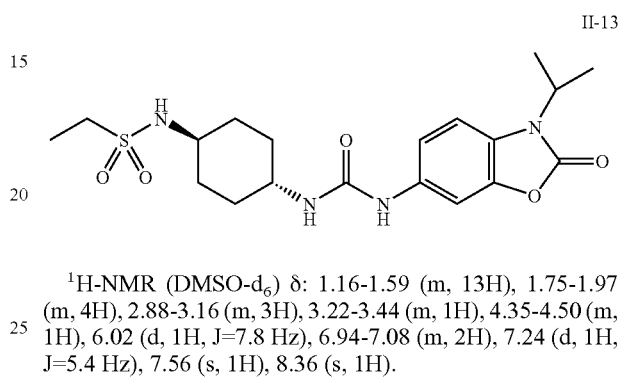

$^1$H-NMR (DMSO-$d_6$) δ: 1.16-1.59 (m, 13H), 1.75-1.97 (m, 4H), 2.88-3.16 (m, 3H), 3.22-3.44 (m, 1H), 4.35-4.50 (m, 1H), 6.02 (d, 1H, J=7.8 Hz), 6.94-7.08 (m, 2H), 7.24 (d, 1H, J=5.4 Hz), 7.56 (s, 1H), 8.36 (s, 1H).

Example 14

[Formula 33]

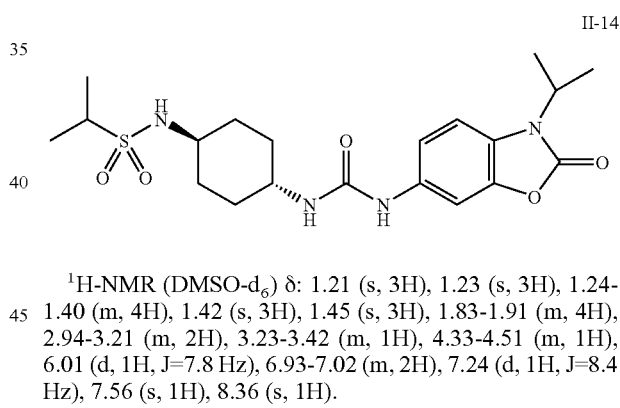

$^1$H-NMR (DMSO-$d_6$) δ: 1.21 (s, 3H), 1.23 (s, 3H), 1.24-1.40 (m, 4H), 1.42 (s, 3H), 1.45 (s, 3H), 1.83-1.91 (m, 4H), 2.94-3.21 (m, 2H), 3.23-3.42 (m, 1H), 4.33-4.51 (m, 1H), 6.01 (d, 1H, J=7.8 Hz), 6.93-7.02 (m, 2H), 7.24 (d, 1H, J=8.4 Hz), 7.56 (s, 1H), 8.36 (s, 1H).

Example 15

[Formula 34]

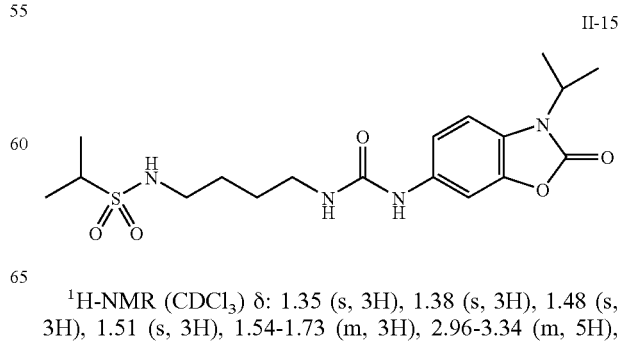

$^1$H-NMR (CDCl$_3$) δ: 1.35 (s, 3H), 1.38 (s, 3H), 1.48 (s, 3H), 1.51 (s, 3H), 1.54-1.73 (m, 3H), 2.96-3.34 (m, 5H), 4.40-4.58 (m, 1H), 5.00-5.16 (m, 1H), 6.95 (d, 1H, J=8.4 Hz), 7.08 (d, 1H, J=8.4 Hz), 7.36 (s, 1H).

Example 16

[Formula 35]

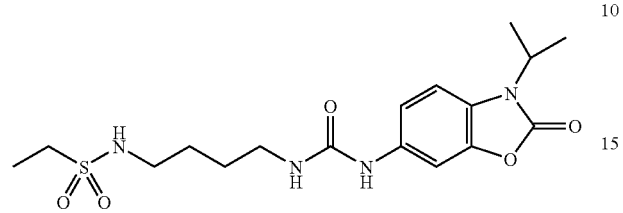

¹H-NMR (DMSO-d₆) δ: 1.18 (t, 3H, J=7.8 Hz), 1.40-1.65 (m, 10H), 2.80-3.16 (m, 6H), 4.35-4.52 (m, 1H), 6.12 (t, 1H, J=8.4 Hz), 6.80-7.11 (m, 2H), 7.25 (d, 1H, J=8.7 Hz), 7.58 (s, 1H), 8.48 (s, 1H).

Example 17

[Formula 36]

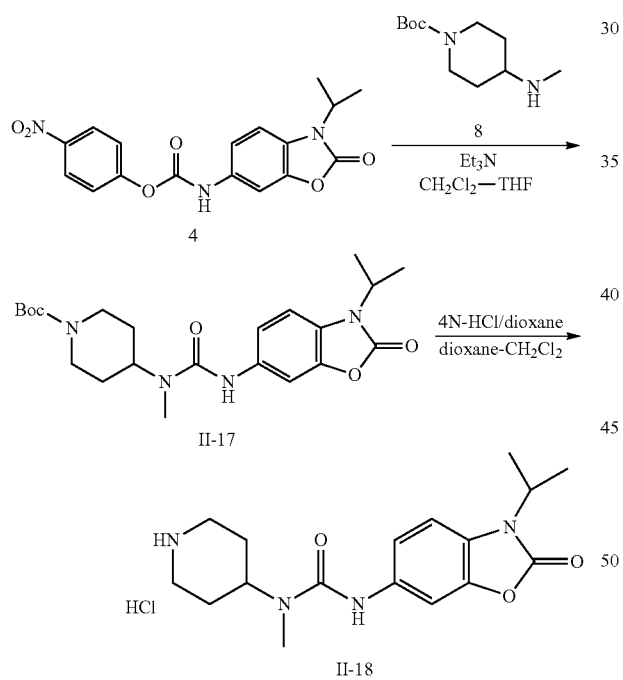

Carbamate (Compound 4) (12.88 g, 27.24 mmol) was dissolved in the mixed solvent made of methylene chloride (150 mL) and THF (150 mL). To the reaction mixture, which was stirred at 0° C., were added 1-Boc-4-methyl-amino piperidine (Compound 8) (6.13 g, 28.60 mmol) and triethylamine (9.5 mL, 68.10 mmol). The whole mixture was warmed up to room temperature and stirred for 15 hours. The solvent was removed under reduced pressure, then to the residue were added cold water and 1N sodium hydroxide solution. The resulting solid was filtered to give Compound II-17 (11.28 g, 96%). Compound II-17 (11.28 g, 26.10 mmol) was dissolved in the mixed solvent made of dioxane (50 mL) and methylene chloride (60 mL), then to the reaction mixture, which was stirred at room temperature, was added 4N dioxane hydrochloride solution (13 mL). The whole mixture was stirred at room temperature for 17 hours and the solvent was removed under reduced pressure to give Compound II-18 (9.74 g, quant.).

II-18: ¹H-NMR (DMSO-d₆) δ: 1.43 (s, 3H), 1.46 (s, 3H), 1.60-1.76 (m, 2H), 1.88-2.16 (m, 2H), 2.83 (s, 3H), 2.85-3.14 (m, 2H), 3.26-3.43 (m, 2H), 4.27-4.52 (m, 2H), 7.20-7.32 (m, 2H), 7.57 (s, 1H), 8.46 (s, 1H), 8.87 (brs, 1H).

Example 18

[Formula 37]

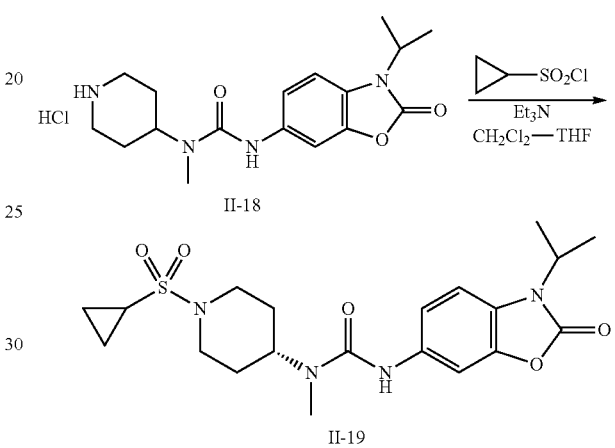

Amine II-18 (400 mg, 1.08 mmol) was dissolved in the mixed solvent made of methylene chloride (8 mL) and THF (8 mL). To the reaction mixture, which was stirred at 0° C., were added triethylamine (0.76 mL, 5.40 mmol) and cyclopropyl sulfonyl chloride (0.23 g, 1.62 mmol). The whole mixture was warmed up to room temperature and stirred for 22 hours. The solvent was removed under reduced presser and the residue was purified with silica-gel column chromatography. The derived product was recrystallized with isopropyl alcohol and methanol to give Compound II-19 (360 mg, 76%).

¹H-NMR (CDCl₃) δ: 0.94-1.08 (m, 2H), 1.14-1.26 (m, 2H), 1.51 (s, 3H), 1.54 (s, 3H), 1.74-1.88 (m, 4H), 2.22-2.34 (m, 1H), 2.80-3.03 (m, 5H), 3.94-4.00 (m, 2H), 4.36-4.60 (m, 2H), 6.43 (s, 1H), 6.94-7.10 (m, 2H), 7.45 (s, 1H).

The following examples were prepared by the same method.

Example 19

[Formula 38]

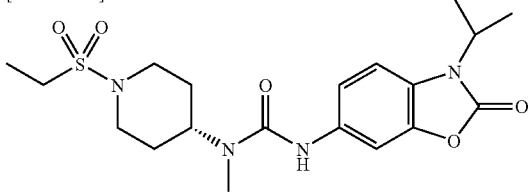

¹H-NMR (CDCl₃) δ: 1.37 (t, 3H, J=7.5 Hz), 1.51 (s, 3H), 1.54 (s, 3H), 1.65-1.85 (m, 4H), 2.80-3.04 (m, 7H), 3.86-3.96 (m, 2H), 4.34-4.60 (m, 2H), 6.42 (s, 1H), 6.92-7.10 (m, 2H), 7.45 (d, 1H, J=1.8 Hz).

Example 20

[Formula 39]

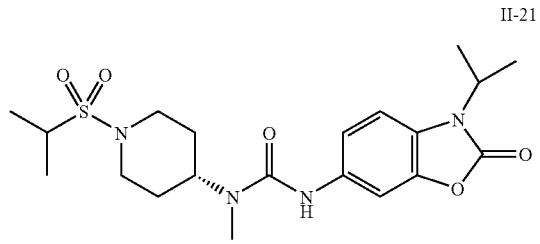

II-21

¹H-NMR (CDCl₃) δ: 1.33 (s, 3H), 1.35 (s, 3H), 1.51 (s, 3H), 1.54 (s, 3H), 1.57-1.85 (m, 4H), 2.83-3.08 (m, 3H), 3.10-3.25 (m, 2H), 3.90-4.00 (m, 2H), 4.36-4.62 (m, 3H), 6.37 (s, 1H), 6.95-7.12 (m, 2H), 7.45 (d, 1H, J=2.1 Hz).

Example 21

[Formula 40]

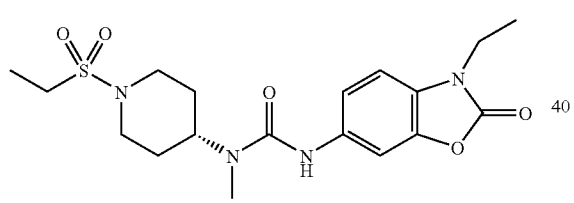

II-22

¹H-NMR (CDCl₃) δ: 1.32-1.46 (m, 5H), 1.50-1.98 (m, 5H), 2.70-3.08 (m, 7H), 3.71-4.00 (m, 4H), 4.37-4.53 (m, 1H), 6.40 (s, 1H), 6.87 (d, 1H, J=8.4 Hz), 7.04-7.14 (m, 1H), 7.46 (s, 1H).

Example 22

[Formula 41]

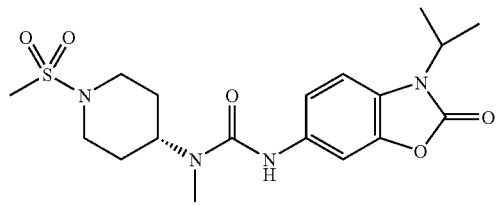

II-23

¹H-NMR (CDCl₃) δ: 1.51 (s, 3H), 1.54 (s, 3H), 1.75-1.88 (m, 3H), 2.63-2.86 (m, 5H), 2.92 (s, 3H), 3.83-3.98 (m, 2H), 4.36-4.62 (m, 3H), 6.41 (s, 1H), 6.96-7.11 (m, 2H), 7.45 (d, 1H, J=2.1 Hz).

Example 23

[Formula 42]

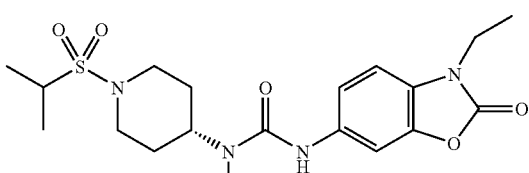

II-24

¹H-NMR (CDCl₃) δ: 1.30-1.44 (m, 8H), 1.62-1.85 (m, 4H), 2.91 (s, 3H), 2.93-3.03 (m, 2H), 3.05-3.28 (m, 2H), 3.77-4.02 (m, 4H), 4.35-4.56 (m, 1H), 6.51 (s, 1H), 6.87 (d, 1H, J=8.4 Hz), 7.10 (dd, 1H, J=8.4, 1.8 Hz), 7.46 (d, 1H, J=1.8 Hz).

Example 24

[Formula 43]

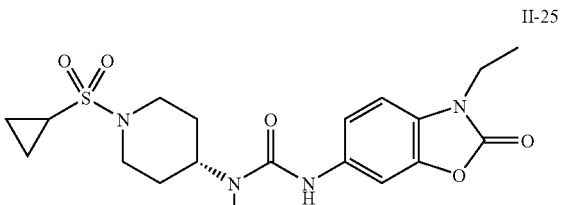

II-25

¹H-NMR (CDCl₃) δ: 0.95-1.08 (m, 2H), 1.12-1.26 (m, 2H), 1.32-1.46 (m, 4H), 1.73-1.89 (m, 3H), 2.22-2.35 (m, 1H), 2.83-3.08 (m, 5H), 3.78-4.02 (m, 4H), 4.34-4.52 (m, 1H), 6.43 (s, 1H), 6.87 (d, 1H, J=8.4 Hz), 7.08 (dd, 1H, J=8.4, 2.1 Hz), 7.46 (d, 1H, J=2.1 Hz).

Example 25

[Formula 44]

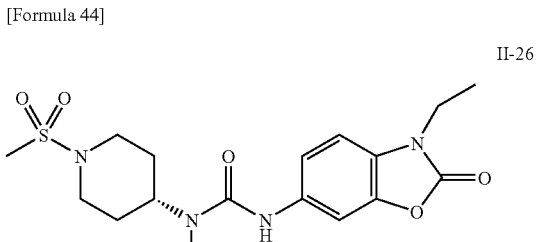

II-26

¹H-NMR (CDCl₃) δ: 1.36 (t, 3H, J=7.5 Hz), 1.66-1.98 (m, 6H), 2.87 (s, 3H), 2.91 (s, 3H), 3.70-4.05 (m, 4H), 4.32-4.57

(m, 1H), 6.49 (s, 1H), 6.88 (d, 1H, J=8.4 Hz), 7.09 (dd, 1H, J=8.4, 1.8 Hz), 7.46 (d, 1H, J=1.8 Hz).

Example 26

[Formula 45]

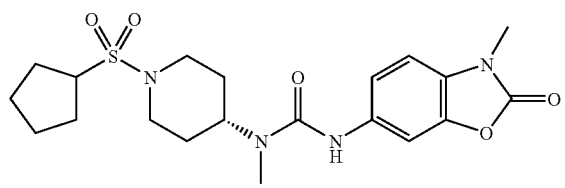

II-27

$^1$H-NMR (CDCl$_3$) δ: 1.44-1.92 (m, 8H), 1.96-2.10 (m, 4H), 2.78-3.03 (m, 5H), 3.30-3.60 (m, 4H), 3.89-4.04 (m, 2H), 4.35-4.56 (m, 1H), 6.45 (s, 1H), 6.85 (d, 1H, J=8.4 Hz), 7.09 (dd, 1H, J=8.4, 1.8 Hz), 7.49 (d, 1H, J=1.8 Hz).

Example 27

[Formula 46]

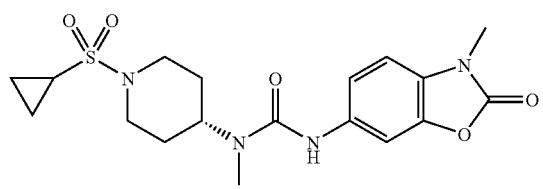

II-28

$^1$H-NMR (CDCl$_3$) δ: 0.93-1.07 (m, 2H), 1.10-1.23 (m, 2H), 1.53-1.69 (m, 2H), 1.73-1.90 (m, 3H), 2.20-2.36 (m, 1H), 2.78-3.01 (m, 4H), 3.39 (s, 3H), 3.84-3.94 (m, 2H), 4.35-4.52 (m, 1H), 6.41 (s, 1H), 6.86 (d, 1H, J=8.4 Hz), 7.08 (dd, 1H, J=8.4, 2.1 Hz), 7.49 (d, 1H, J=2.1 Hz).

Example 28

[Formula 47]

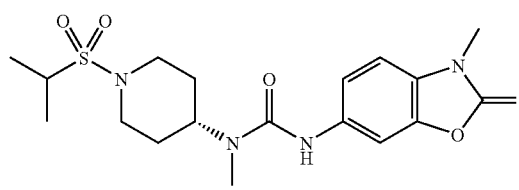

II-29

$^1$H-NMR (CDCl$_3$) δ: 1.33 (s, 3H), 1.35 (s, 3H), 1.54-1.85 (m, 4H), 2.80-3.08 (m, 4H), 3.10-3.26 (m, 2H), 3.38 (s, 3H), 3.82-4.01 (m, 2H), 4.37-4.55 (m, 1H), 6.35 (s, 1H), 6.85 (d, 1H, J=8.4 Hz), 7.07 (dd, 1H, J=8.4, 2.1 Hz), 7.48 (d, 1H, J=2.1 Hz).

Example 29

[Formula 48]

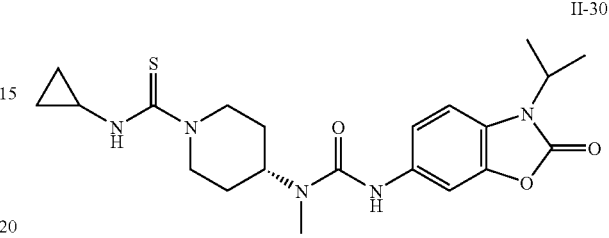

II-30

$^1$H-NMR (DMSO-d$_6$) δ: 0.44-0.57 (m, 2H), 0.60-0.74 (m, 2H), 1.43 (s, 3H), 1.46 (s, 3H), 1.48-1.71 (m, 4H), 2.78 (s, 3H), 2.83-3.05 (m, 3H), 4.22-4.58 (m, 2H), 4.64-4.83 (m, 2H), 7.18-7.34 (m, 2H), 7.50-7.65 (m, 2H), 8.33 (s, 1H).

Example 30

[Formula 49]

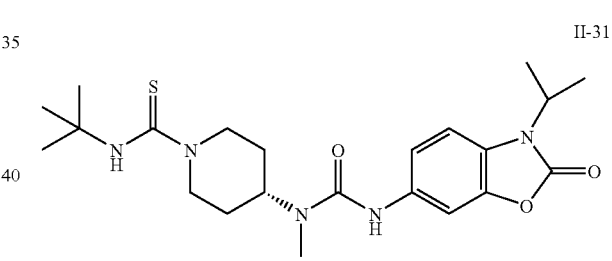

II-31

$^1$H-NMR (DMSO-d$_6$) δ: 1.44 (s, 3H), 1.46 (s, 3H), 1.48 (s, 9H), 1.52-1.70 (m, 4H), 2.66-3.03 (m, 5H), 4.20-4.38 (m, 1H), 4.39-4.56 (m, 1H), 4.58-4.83 (m, 2H), 6.72 (s, 1H), 7.16-7.34 (m, 2H), 7.55 (d, 1H, J=1.8 Hz), 8.33 (s, 1H).

Example 31

[Formula 50]

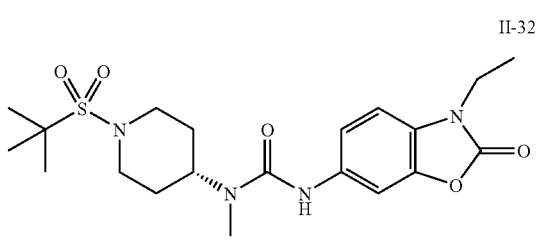

II-32

¹H-NMR (DMSO-d₆) δ: 1.18-1.45 (m, 12H), 1.53-1.74 (m, 4H), 2.82 (s, 3H), 2.98-3.16 (s, 2H), 3.60-3.94 (m, 4H), 4.10-4.36 (m, 1H), 7.04-7.36 (m, 2H), 7.54 (d, 1H, J=1.8 Hz), 8.31 (d, 1H, J=3.0 Hz).

Example 32

[Formula 51]

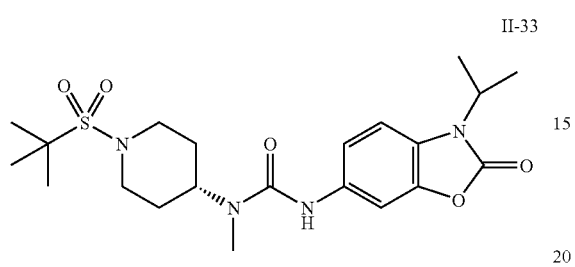

II-33

¹H-NMR (DMSO-d₆) δ: 1.29 (s, 9H), 1.43 (s, 3H), 1.46 (s, 3H), 1.55-1.75 (m, 4H), 2.82 (s, 3H), 2.96-3.18 (m, 2H), 3.62-3.88 (m, 2H), 4.06-4.35 (m, 1H), 4.37-4.54 (m, 1H), 7.10-7.38 (m, 2H), 7.54 (s, 1H), 8.32 (s, 1H).

The following examples were analyzed by liquid chromatography mass spectrometry (LC-MS) (Waters Corp.). Luna5 μC18(2)100A (50 mm×4.60 mmΦ) (Phenomenex, Inc.) was used as column. A linear gradient of acetonitrile concentration (10-100%/3 min) was generated at a flow rate of 3.0 mL/min to elute the following examples to be analyzed.

Example 33

[Formula 52]

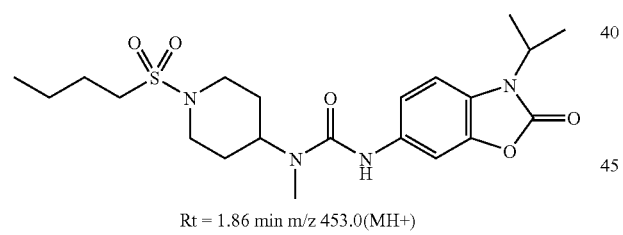

II-34

Rt = 1.86 min m/z 453.0(MH+)

Example 34

[Formula 53]

II-35

Rt = 1.25 min m/z 375.0(MH+)

Example 35

[Formula 54]

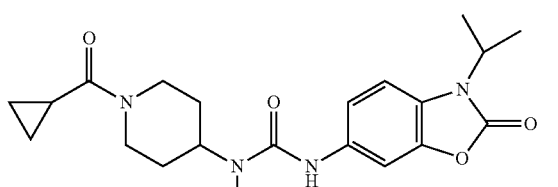

II-36

Rt = 1.45 min m/z 401.1(MH+)

Example 36

[Formula 55]

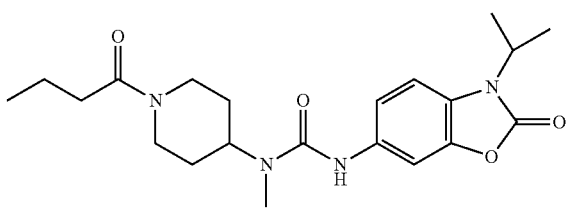

II-37

Rt = 1.52 min m/z 403.4(MH+)

Example 37

[Formula 56]

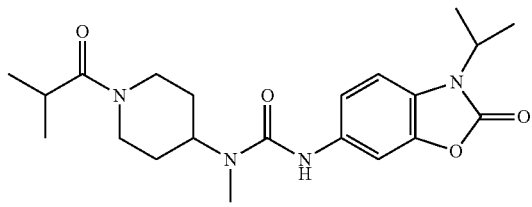

II-38

Rt = 1.53 min m/z 403.4(MH+)

Example 38
[Formula 57]
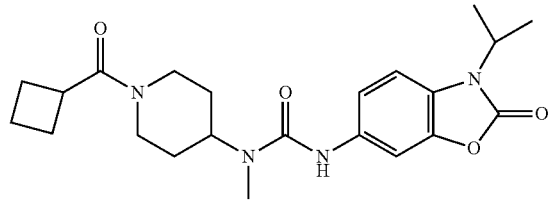
II-39
Rt = 1.58 min m/z 415.4(MH+)
Example 39
[Formula 58]
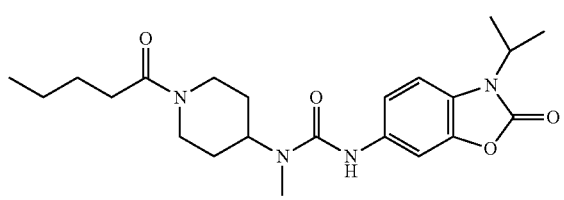
II-40
Rt = 1.69 min m/z 417.0(MH+)
Example 40
[Formula 59]
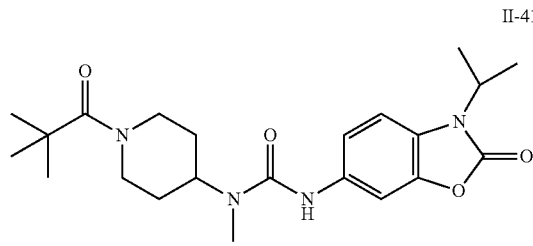
II-41
Rt = 1.69 min m/z 417.0(MH+)
Example 41
[Formula 60]
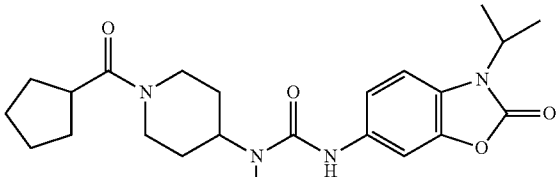
II-42
Rt = 1.73 min m/z 429.5(MH+)
Example 42
[Formula 61]
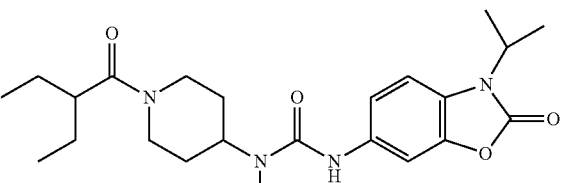
II-43
Rt = 1.77 min m/z 431.6(MH+)
As a compound of the present invention, compounds including the following can be prepared as well as the above Examples. The abbreviations used for X are as follows:
[Formula 62]
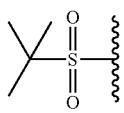
X-1
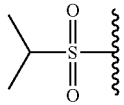
X-2
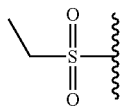
X-3
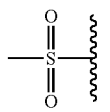
X-4
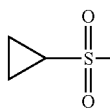
X-5

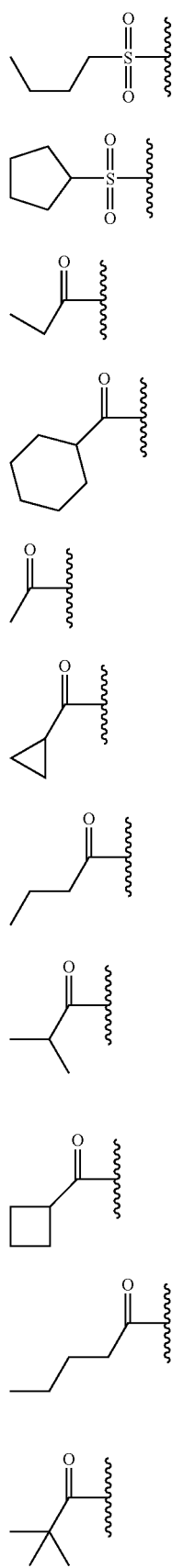
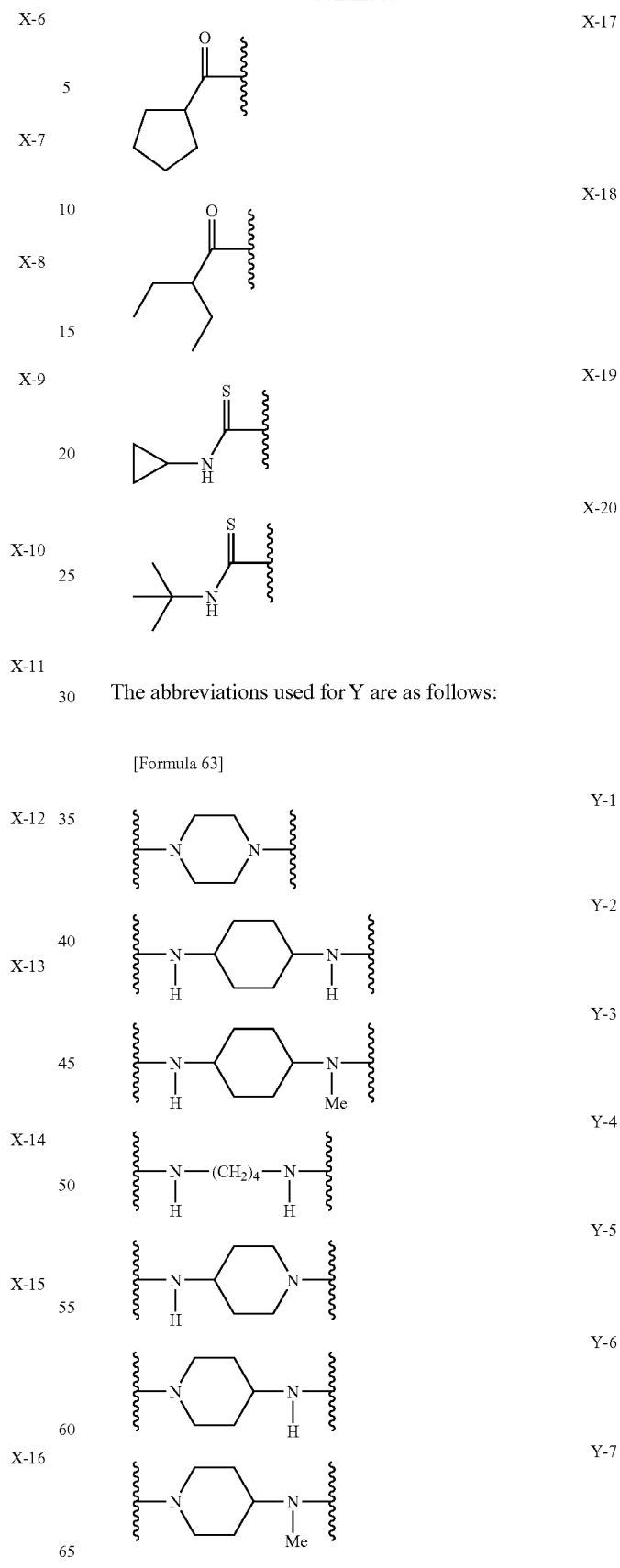
The abbreviations used for Y are as follows:
[Formula 63]

The abbreviations used for $R^1$ are as follows:

[Formula 64]

H    F
$R^1$-1   $R^1$-2

The abbreviations used for $R^2$ are as follows:

[Formula 65]

H    Me
$R^2$-1   $R^2$-2

The abbreviations used for Z are as follows:

[Formula 66]

O    NH    NMe
Z-1   Z-2   Z-3

The abbreviations used for $R^3$ are as follows:

[Formula 67]

Me   Et   i-Pr   n-Pr
$R^3$-1  $R^3$-2  $R^3$-3  $R^3$-4

Concretely described below is a compound defined by using the formula (IV).

[Formula 68]

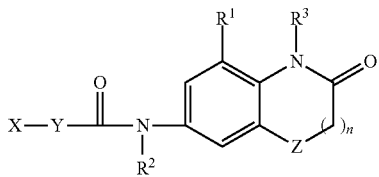

(IV)

$(X,Y,R^1,R^2,Z,R^3,n)=$(X-1,Y-3,$R^1$-1,$R^2$-1,Z-1,$R^3$-1,0), (X-1,Y-3,$R^1$-1,$R^2$-1,Z-1,$R^3$-1,1), (X-1,Y-3,$R^1$-1,$R^2$-1,Z-1,$R^3$-2,0), (X-1,Y-3,$R^1$-1,$R^2$-1,Z-1,$R^3$-2,1), (X-1,Y-3,$R^1$-1,$R^2$-1,Z-1,$R^3$-3,0), (X-1,Y-3,$R^1$-1,$R^2$-1,Z-1,$R^3$-3,1), (X-1,Y-3,$R^1$-1,$R^2$-1,Z-1,$R^3$-1,0), (X-1,Y-3,$R^1$-1,$R^2$-1,Z-1,$R^3$-1,1), (X-1,Y-3,$R^1$-1,$R^2$-1,Z-2,$R^3$-2,0), (X-1,Y-3,$R^1$-1,$R^2$-1,Z-2,$R^3$-2,1), (X-1,Y-3,$R^1$-1,$R^2$-1,Z-2,$R^3$-3,0), (X-1,Y-3,$R^1$-1,$R^2$-1,Z-2,$R^3$-3,1), (X-1,Y-3,$R^1$-1,$R^2$-1,Z-2,$R^3$-1,0), (X-1,Y-3,$R^1$-1,$R^2$-1,Z-2,$R^3$-1,1), (X-1,Y-3,$R^1$-1,$R^2$-1,Z-2,$R^3$-2,0), (X-1,Y-3,$R^1$-1,$R^2$-1,Z-2,$R^3$-2,1), (X-1,Y-3,$R^1$-1,$R^2$-1,Z-3,$R^3$-3,0), (X-1,Y-3,$R^1$-1,$R^2$-1,Z-3,$R^3$-3,1), (X-1,Y-3,$R^1$-1,$R^2$-1,Z-3,$R^3$-1,0), (X-1,Y-3,$R^1$-1,$R^2$-1,Z-3,$R^3$-1,1), (X-1,Y-3,$R^1$-1,$R^2$-1,Z-3,$R^3$-2,0), (X-1,Y-3,$R^1$-1,$R^2$-1,Z-3,$R^3$-2,1), (X-1,Y-3,$R^1$-1,$R^2$-1,Z-3,$R^3$-3,0), (X-1,Y-3,$R^1$-1,$R^2$-1,Z-3,$R^3$-3,1), (X-1,Y-3,$R^1$-2,$R^2$-1,Z-1,$R^3$-1,0), (X-1,Y-3,$R^1$-2,$R^2$-1,Z-1,$R^3$-1,1), (X-1,Y-3,$R^1$-2,$R^2$-1,Z-1,$R^3$-2,0), (X-1,Y-3,$R^1$-2,$R^2$-1,Z-1,$R^3$-2,1), (X-1,Y-3,$R^1$-2,$R^2$-1,Z-1,$R^3$-3,0), (X-1,Y-3,$R^1$-2,$R^2$-1,Z-1,$R^3$-3,1), (X-1,Y-3,$R^1$-2,$R^2$-1,Z-1,$R^3$-1,0), (X-1,Y-3,$R^1$-2,$R^2$-1,Z-1,$R^3$-1,1), (X-1,Y-3,$R^1$-2,$R^2$-1,Z-2,$R^3$-2,0), (X-1,Y-3,$R^1$-2,$R^2$-1,Z-2,$R^3$-2,1), (X-1,Y-3,$R^1$-2,$R^2$-1,Z-2,$R^3$-3,0), (X-1,Y-3,$R^1$-2,$R^2$-1,Z-2,$R^3$-3,1), (X-1,Y-3,$R^1$-2,$R^2$-1,Z-2,$R^3$-1,0), (X-1,Y-3,$R^1$-2,$R^2$-1,Z-2,$R^3$-1,1), (X-1,Y-3,$R^1$-2,$R^2$-1,Z-2,$R^3$-2,0), (X-1,Y-3,$R^1$-2,$R^2$-1,Z-2,$R^3$-2,1), (X-1,Y-3,$R^1$-2,$R^2$-1,Z-3,$R^3$-3,0), (X-1,Y-3,$R^1$-2,$R^2$-1,Z-3,$R^3$-3,1), (X-1,Y-3,$R^1$-2,$R^2$-1,Z-3,$R^3$-1,0), (X-1,Y-3,$R^1$-2,$R^2$-1,Z-3,$R^3$-1,1), (X-1,Y-3,$R^1$-2,$R^2$-1,Z-3,$R^3$-2,0), (X-1,Y-3,$R^1$-2,$R^2$-1,Z-3,$R^3$-2,1), (X-1,Y-3,$R^1$-2,$R^2$-1,Z-3,$R^3$-3,0), (X-1,Y-3,$R^1$-2,$R^2$-1,Z-3,$R^3$-3,1), (X-1,Y-5,$R^1$-1,$R^2$-1,Z-1,$R^3$-1,0), (X-1,Y-5,$R^1$-1,$R^2$-1,Z-1,$R^3$-1,1), (X-1,Y-5,$R^1$-1,$R^2$-1,Z-1,$R^3$-1,0), (X-1,Y-5,$R^1$-1,$R^2$-1,Z-1,$R^3$-1,1), (X-1,Y-5,$R^1$-1,$R^2$-1,Z-2,$R^3$-2,0), (X-1,Y-5,$R^1$-1,$R^2$-1,Z-2,$R^3$-2,1), (X-1,Y-5,$R^1$-1,$R^2$-1,Z-2,$R^3$-3,0), (X-1,Y-5,$R^1$-1,$R^2$-1,Z-2,$R^3$-3,1), (X-1,Y-5,$R^1$-1,$R^2$-1,Z-2,$R^3$-1,0), (X-1,Y-5,$R^1$-1,$R^2$-1,Z-2,$R^3$-1,1), (X-1,Y-5,$R^1$-1,$R^2$-1,Z-2,$R^3$-2,0), (X-1,Y-5,$R^1$-1,$R^2$-1,Z-2,$R^3$-2,1), (X-1,Y-5,$R^1$-1,$R^2$-1,Z-3,$R^3$-3,0), (X-1,Y-5,$R^1$-1,$R^2$-1,Z-3,$R^3$-3,1), (X-1,Y-5,$R^1$-1,$R^2$-1,Z-3,$R^3$-1,0), (X-1,Y-5,$R^1$-1,$R^2$-1,Z-3,$R^3$-1,1), (X-1,Y-5,$R^1$-1,$R^2$-1,Z-3,$R^3$-2,0), (X-1,Y-5,$R^1$-1,$R^2$-1,Z-3,$R^3$-2,1), (X-1,Y-5,$R^1$-1,$R^2$-1,Z-3,$R^3$-3,0), (X-1,Y-5,$R^1$-1,$R^2$-1,Z-3,$R^3$-3,1), (X-1,Y-5,$R^1$-1,$R^2$-2,Z-1,$R^3$-1,0), (X-1,Y-5,$R^1$-1,$R^2$-2,Z-1,$R^3$-1,1), (X-1,Y-5,$R^1$-1,$R^2$-2,Z-1,$R^3$-2,0), (X-1,Y-5,$R^1$-1,$R^2$-2,Z-1,$R^3$-2,1), (X-1,Y-5,$R^1$-1,$R^2$-2,Z-1,$R^3$-3,0), (X-1,Y-5,$R^1$-1,$R^2$-2,Z-1,$R^3$-3,1), (X-1,Y-5,$R^1$-1,$R^2$-2,Z-1,$R^3$-1,0), (X-1,Y-5,$R^1$-1,$R^2$-2,Z-1,$R^3$-1,1), (X-1,Y-5,$R^1$-1,$R^2$-2,Z-2,$R^3$-2,0), (X-1,Y-5,$R^1$-1,$R^2$-2,Z-2,$R^3$-2,1), (X-1,Y-5,$R^1$-1,$R^2$-2,Z-2,$R^3$-3,0), (X-1,Y-5,$R^1$-1,$R^2$-2,Z-2,$R^3$-3,1), (X-1,Y-5,$R^1$-1,$R^2$-2,Z-2,$R^3$-1,0), (X-1,Y-5,$R^1$-1,$R^2$-2,Z-2,$R^3$-1,1), (X-1,Y-5,$R^1$-1,$R^2$-2,Z-2,$R^3$-2,0), (X-1,Y-5,$R^1$-1,$R^2$-2,Z-2,$R^3$-2,1), (X-1,Y-5,$R^1$-1,$R^2$-2,Z-3,$R^3$-3,0), (X-1,Y-5,$R^1$-1,$R^2$-2,Z-3,$R^3$-3,1), (X-1,Y-5,$R^1$-1,$R^2$-2,Z-3,$R^3$-1,0), (X-1,Y-5,$R^1$-1,$R^2$-2,Z-3,$R^3$-1,1), (X-1,Y-5,$R^1$-1,$R^2$-2,Z-3,$R^3$-2,0), (X-1,Y-5,$R^1$-1,$R^2$-2,Z-3,$R^3$-2,1), (X-1,Y-5,$R^1$-1,$R^2$-2,Z-3,$R^3$-3,0), (X-1,Y-5,$R^1$-1,$R^2$-2,Z-3,$R^3$-3,1), (X-1,Y-6,$R^1$-1,$R^2$-1,Z-1,$R^3$-1,0), (X-1,Y-6,$R^1$-1,$R^2$-1,Z-1,$R^3$-1,1), (X-1,Y-6,$R^1$-1,$R^2$-1,Z-1,$R^3$-2,0), (X-1,Y-6,$R^1$-1,$R^2$-1,Z-1,$R^3$-2,1), (X-1,Y-6,$R^1$-1,$R^2$-1,Z-1,$R^3$-3,0), (X-1,Y-6,$R^1$-1,$R^2$-1,Z-1,$R^3$-3,1), (X-1,Y-6,$R^1$-1,$R^2$-1,Z-1,$R^3$-1,0), (X-1,Y-6,$R^1$-1,$R^2$-1,Z-1,$R^3$-1,1), (X-1,Y-6,$R^1$-1,$R^2$-1,Z-2,$R^3$-2,0), (X-1,Y-6,$R^1$-1,$R^2$-1,Z-2,$R^3$-2,1), (X-1,Y-6,$R^1$-1,$R^2$-1,Z-2,$R^3$-3,0), (X-1,Y-6,$R^1$-1,$R^2$-1,Z-2,$R^3$-3,1), (X-1,Y-6,$R^1$-1,$R^2$-1,Z-2,$R^3$-1,0), (X-1,Y-6,$R^1$-1,$R^2$-1,Z-2,$R^3$-1,1), (X-1,Y-6,$R^1$-1,$R^2$-1,Z-2,$R^3$-2,0), (X-1,Y-6,$R^1$-1,$R^2$-1,Z-2,$R^3$-2,1), (X-1,Y-6,$R^1$-1,$R^2$-1,Z-3,$R^3$-3,0), (X-1,Y-6,$R^1$-1,$R^2$-1,Z-3,$R^3$-3,1), (X-1,Y-6,$R^1$-1,$R^2$-1,Z-3,$R^3$-1,0), (X-1,Y-6,$R^1$-1,$R^2$-1,Z-3,$R^3$-1,1), (X-1,Y-6,$R^1$-1,$R^2$-1,Z-3,$R^3$-2,0), (X-1,Y-6,$R^1$-1,$R^2$-1,Z-3,$R^3$-2,1), (X-1,Y-6,$R^1$-1,$R^2$-1,Z-3,$R^3$-3,0), (X-1,Y-6,$R^1$-1,$R^2$-1,Z-3,$R^3$-3,1), (X-1,Y-6,$R^1$-1,$R^2$-2,Z-1,$R^3$-1,0), (X-1,Y-7,$R^1$-1,$R^2$-1,Z-1,$R^3$-1,0), (X-1,Y-7,$R^1$-1,$R^2$-1,Z-1,$R^3$-1,1), (X-1,Y-7,$R^1$-1,$R^2$-1,Z-1,$R^3$-1,0), (X-1,Y-7,$R^1$-1,$R^2$-1,Z-1,$R^3$-1,1), (X-1,Y-7,$R^1$-1,$R^2$-1,Z-2,$R^3$-2,0), (X-1,Y-7,$R^1$-1,$R^2$-1,Z-2,$R^3$-2,1), (X-1,Y-7,$R^1$-1,$R^2$-1,Z-2,$R^3$-3,0), (X-1,Y-7,$R^1$-1,$R^2$-1,Z-2,$R^3$-3,1), (X-1,Y-7,$R^1$-1,$R^2$-1,Z-2,$R^3$-1,0), (X-1,Y-7,$R^1$-1,$R^2$-1,Z-2,$R^3$-1,1), (X-1,Y-7,$R^1$-1,$R^2$-1,Z-2,$R^3$-2,0), (X-1,Y-7,$R^1$-1,$R^2$-1,Z-2,$R^3$-2,1), (X-1,Y-7,$R^1$-1,$R^2$-1,Z-3,$R^3$-3,0), (X-1,Y-7,$R^1$-1,$R^2$-1,Z-3,$R^3$-3,1), (X-1,Y-7,$R^1$-1,$R^2$-1,Z-3,$R^3$-1,0), (X-1,Y-7,$R^1$-1,$R^2$-1,Z-3,$R^3$-1,1), (X-1,Y-7,$R^1$-1,$R^2$-1,Z-3,$R^3$-2,0), (X-1,Y-7,$R^1$-1,$R^2$-1,Z-3,$R^3$-2,1), (X-1,Y-7,$R^1$-1,$R^2$-1,Z-3,$R^3$-3,0), (X-1,Y-7,$R^1$-1,$R^2$-1,Z-3,$R^3$-3,1), (X-1,Y-7,$R^1$-2,$R^2$-1,Z-1,$R^3$-1,0), (X-1,Y-7,$R^1$-2,$R^2$-1,Z-1,$R^3$-1,1), (X-1,Y-7,$R^1$-2,$R^2$-1,Z-1,$R^3$-2,0), (X-1,Y-7,$R^1$-2,$R^2$-1,Z-1,$R^3$-2,1), (X-1,Y-7,$R^1$-2,$R^2$-1,Z-1,$R^3$-3,0), (X-1,Y-7,$R^1$-2,$R^2$-1,Z-1,$R^3$-3,1), (X-1,Y-7,$R^1$-2,$R^2$-1,Z-1,$R^3$-1,0), (X-1,Y-7,$R^1$-2,$R^2$-1,Z-1,$R^3$-1,1), (X-1,Y-7,$R^1$-2,$R^2$-1,Z-2,$R^3$-2,0), (X-1,Y-7,$R^1$-2,$R^2$-1,Z-2,$R^3$-2,1), (X-1,Y-7,$R^1$-2,$R^2$-1,Z-2,$R^3$-3,0), (X-1,Y-7,$R^1$-2,$R^2$-1,Z-2,$R^3$-3,1), (X-1,Y-7,$R^1$-2,$R^2$-1,Z-2,$R^3$-1,0), (X-1,Y-7,$R^1$-2,$R^2$-1,Z-2,$R^3$-1,1), (X-1,Y-7,$R^1$-2,$R^2$-

1,Z-2,R³-2,0), (X-1,Y-7,R¹-2,R²-1,Z-2,R³-2,1), (X-1,Y-7, R¹-2,R²-1,Z-3,R³-3,0), (X-1,Y-7,R¹-2,R²-1,Z-3,R³-3,1), (X-1,Y-7,R¹-2,R²-1,Z-3,R³-1,0), (X-1,Y-7,R¹-2,R²-1,Z-3, R³-1,1), (X-1,Y-7,R¹-2,R²-1,Z-3,R³-2,0), (X-1,Y-7,R¹-2,R²-1,Z-3,R³-2,1), (X-1,Y-7,R¹-2,R²-1,Z-3,R³-3,0), (X-1,Y-7, R¹-2,R²-1,Z-3,R³-3,1)

(X-2,Y-3,R¹-1,R²-1,Z-1,R³-1,0),(X-2,Y-3,R¹-1,R²-1,Z-1, R³-1,1), (X-2,Y-3,R¹-1,R²-1,Z-1,R³-2,0), (X-2,Y-3,R¹-R²-1,Z-1,R³-2,1), (X-2,Y-3,R¹-1,R²-1,Z-1,R³-3,0), (X-2,Y-3, R¹-1,R²-1,Z-1,R³-3,1), (X-2,Y-3,R¹-1,R²-1,Z-1,R³-1,0), (X-2,Y-3,R¹-1,R²-1,Z-1,R³-1,1), (X-2,Y-3,R¹-1,R²-1,Z-2, R³-2,0), (X-2,Y-3,R¹-1,R²-1,Z-2,R³-2,1), (X-2,Y-3,R¹-1,R²-1,Z-2,R³-3,0), (X-2,Y-3,R¹-1,R²-1,Z-2,R³-3,1), (X-2,Y-3, R¹-1,R²-1,Z-2,R³-1,0), (X-2,Y-3,R¹-1,R²-1,Z-2,R³-1,1), (X-2,Y-3,R¹-1,R²-1,Z-2,R³-2,0), (X-2,Y-3,R¹-1,R²-1,Z-2, R³-2,1), (X-2,Y-3,R¹-1,R²-1,Z-3,R³-3,0), (X-2,Y-3,R¹-1,R²-1,Z-3,R³-3,1), (X-2,Y-3,R¹-1,R²-1,Z-3,R³-1,0), (X-2,Y-3, R¹-1,R²-1,Z-3,R³-1,1), (X-2,Y-3,R¹-1,R²-1,Z-3,R³-2,0), (X-2,Y-3,R¹-1,R²-1,Z-3,R³-2,1), (X-2,Y-3,R¹-1,R²-1,Z-3, R³-3,0), (X-2,Y-3,R¹-1,R²-1,Z-3,R³-3,1), (X-2,Y-5,R¹-1,R²-1,Z-1,R³-1,0), (X-2,Y-5,R¹-1,R²-1,Z-1,R³-1,1), (X-2,Y-5, R¹-1,R²-1,Z-1,R³-1,0), (X-2,Y-5,R¹-1,R²-1,Z-1,R³-1,1), (X-2,Y-5,R¹-1,R²-1,Z-2,R³-2,0), (X-2,Y-5,R¹-1,R²-1,Z-2, R³-2,1), (X-2,Y-5,R¹-1,R²-1,Z-2,R³-3,0), (X-2,Y-5,R¹-1,R²-1,Z-2,R³-3,1), (X-2,Y-5,R¹-1,R²-1,Z-2,R³-1,0), (X-2,Y-5, R¹-1,R²-1,Z-2,R³-1,1), (X-2,Y-5,R¹-1,R²-1,Z-2,R³-2,0), (X-2,Y-5,R¹-1,R²-1,Z-2,R³-2,1), (X-2,Y-5,R¹-1,R²-1,Z-3, R³-3,0), (X-2,Y-5,R¹-1,R²-1,Z-3,R³-3,1), (X-2,Y-5,R¹-1,R²-1,Z-3,R³-1,0), (X-2,Y-5,R¹-1,R²-1,Z-3,R³-1,1), (X-2,Y-5, R¹-1,R²-1,Z-3,R³-2,0), (X-2,Y-5,R¹-1,R²-1,Z-3,R³-2,1), (X-2,Y-5,R¹-1,R²-1,Z-3,R³-3,0), (X-2,Y-5,R¹-1,R²-1,Z-3, R³-3,1), (X-2,Y-6,R¹-1,R²-1,Z-1,R³-1,0), (X-2,Y-6,R¹-1,R²-1,Z-1,R³-1,1), (X-2,Y-6,R¹-1,R²-1,Z-1,R³-2,0), (X-2,Y-6, R¹-1,R²-1,Z-1,R³-2,1), (X-2,Y-6,R¹-1,R²-1,Z-1,R³-1,0), (X-2,Y-6,R¹-1,R²-1,Z-1,R³-1,1), (X-2,Y-6,R¹-1,R²-1,Z-2, R³-2,0), (X-2,Y-6,R¹-1,R²-1,Z-2,R³-2,1), (X-2,Y-6,R¹-1,R²-1,Z-2,R³-3,0), (X-2,Y-6,R¹-1,R²-1,Z-2,R³-3,1), (X-2,Y-6, R¹-1,R²-1,Z-2,R³-1,0), (X-2,Y-6,R¹-1,R²-1,Z-2,R³-1,1), (X-2,Y-6,R¹-1,R²-1,Z-2,R³-2,0), (X-2,Y-6,R¹-1,R²-1,Z-2, R³-2,1), (X-2,Y-6,R¹-1,R²-1,Z-3,R³-3,0), (X-2,Y-6,R¹-1,R²-1,Z-3,R³-3,1), (X-2,Y-6,R¹-1,R²-1,Z-3,R³-1,0), (X-2,Y-6, R¹-1,R²-1,Z-3,R³-1,1), (X-2,Y-6,R¹-1,R²-1,Z-3,R³-2,0), (X-2,Y-6,R¹-1,R²-1,Z-3,R³-2,1), (X-2,Y-6,R¹-1,R²-1,Z-3, R³-3,0), (X-2,Y-6,R¹-1,R²-1,Z-3,R³-3,1), (X-2,Y-6,R¹-2,2,R²-1,R³-1,0), (X-2,Y-6,R¹-2,R²-1,Z-1,R³-1,0), (X-2,Y-6, R¹-2,R²-1,Z-1,R³-1,1), (X-2,Y-6,R¹-2,R²-1,Z-1,R³-2,0), (X-2,Y-6,R¹-2,R²-1,Z-1,R³-2,1), (X-2,Y-6,R¹-2,R²-1,Z-1, R³-3,0), (X-2,Y-6,R¹-2,R²-1,Z-1,R³-3,1), (X-2,Y-6,R¹-2,R²-1,Z-1,R³-1,0), (X-2,Y-6,R¹-2,R²-1,Z-1,R³-1,1), (X-2,Y-6, R¹-2,R²-1,Z-2,R³-2,0), (X-2,Y-6,R¹-2,R²-1,Z-2,R³-2,1), (X-2,Y-6,R¹-2,R²-1,Z-2,R³-3,0), (X-2,Y-6,R¹-2,R²-1,Z-2, R³-3,1), (X-2,Y-6,R¹-2,R²-1,Z-2,R³-1,0), (X-2,Y-6,R¹-2,R²-1,Z-2,R³-1,1), (X-2,Y-6,R¹-2,R²-1,Z-2,R³-2,0), (X-2,Y-6, R¹-2,R²-1,Z-2,R³-2,1), (X-2,Y-6,R¹-2,R²-1,Z-3,R³-3,0), (X-2,Y-6,R¹-2,R²-1,Z-3,R³-3,1), (X-2,Y-6,R¹-2,R²-1,Z-3, R³-1,0), (X-2,Y-6,R¹-2,R²-1,Z-3,R³-1,1), (X-2,Y-6,R¹-2,R²-1,Z-3,R³-2,0), (X-2,Y-6,R¹-2,R²-1,Z-3,R³-2,1), (X-2,Y-6, R¹-2,R²-1,Z-3,R³-3,0), (X-2,Y-6,R¹-2,R²-1,Z-3,R³-3,1), (X-2,Y-7,R¹-1,R²-1,Z-1,R³-1,0), (X-2,Y-7,R¹-1,R²-1,Z-1, R³-1,1), (X-2,Y-7,R¹-1,R²-1,Z-1,R³-1,0), (X-2,Y-7,R¹-1,R²-1,Z-1,R³-1,1), (X-2,Y-7,R¹-1,R²-1,Z-2,R³-2,0), (X-2,Y-7, R¹-1,R²-1,Z-2,R³-2,1), (X-2,Y-7,R¹-1,R²-1,Z-2,R³-3,0), (X-2,Y-7,R¹-1,R²-1,Z-2,R³-3,1), (X-2,Y-7,R¹-1,R²-1,Z-2, R³-1,0), (X-2,Y-7,R¹-1,R²-1,Z-2,R³-1,1), (X-2,Y-7,R¹-1,R²-1,Z-2,R³-2,0), (X-2,Y-7,R¹-1,R²-1,Z-2,R³-2,1), (X-2,Y-7, R¹-1,R²-1,Z-3,R³-3,0), (X-2,Y-7,R¹-1,R²-1,Z-3,R³-3,1), (X-2,Y-7,R¹-1,R²-1,Z-3,R³-1,0), (X-2,Y-7,R¹-1,R²-1,Z-3,

R³-1,1), (X-2,Y-7,R¹-1,R²-1,Z-3,R³-2,0), (X-2,Y-7,R¹-1,R²-1,Z-3,R³-2,1), (X-2,Y-7,R¹-1,R²-1,Z-3,R³-3,0), (X-2,Y-7, R¹-1,R²-1,Z-3,R³-3,1), (X-2,Y-7,R¹-2,R²-1,Z-1,R³-1,0), (X-2,Y-7,R¹-2,R²-1,Z-1,R³-1,1), (X-2,Y-7,R¹-2,R²-1,Z-1, R³-2,0), (X-2,Y-7,R¹-2,R²-1,Z-1,R³-2,1), (X-2,Y-7,R¹-2,R²-1,Z-1,R³-3,0), (X-2,Y-7,R¹-2,R²-1,Z-1,R³-3,1), (X-2,Y-7, R¹-2,R²-1,Z-1,R³-1,0), (X-2,Y-7,R¹-2,R²-1,Z-1,R³-1,1), (X-2,Y-7,R¹-2,R²-1,Z-2,R³-2,0), (X-2,Y-7,R¹-2,R²-1,Z-2, R³-2,1), (X-2,Y-7,R¹-2,R²-1,Z-2,R³-3,0), (X-2,Y-7,R¹-2,R²-1,Z-2,R³-3,1), (X-2,Y-7,R¹-2,R²-1,Z-2,R³-1,0), (X-2,Y-7, R¹-2,R²-1,Z-2,R³-1,1), (X-2,Y-7,R¹-2,R²-1,Z-2,R³-2,0), (X-2,Y-7,R¹-2,R²-1,Z-2,R³-2,1), (X-2,Y-7,R¹-2,R²-1,Z-3, R³-3,0), (X-2,Y-7,R¹-2,R²-1,Z-3,R³-3,1), (X-2,Y-7,R¹-2,R²-1,Z-3,R³-1,0), (X-2,Y-7,R¹-2,R²-1,Z-3,R³-1,1), (X-2,Y-7, R¹-2,R²-1,Z-3,R³-2,0), (X-2,Y-7,R¹-2,R²-1,Z-3,R³-2,1), (X-2,Y-7,R¹-2,R²-1,Z-3,R³-3,0), (X-2,Y-7,R¹-2,R²-1,Z-3, R³-3,1)

(X-3,Y-3,R¹-1,R²-1,Z-1,R³-1,0), (X-3,Y-3,R¹-1,R²-1,Z-1, R³-1,1), (X-3,Y-3,R¹-1,R²-1,Z-1,R³-2,0), (X-3,Y-3,R¹-1,R²-1,Z-1,R³-2,1), (X-3,Y-3,R¹-1,R²-1,Z-1,R³-3,0), (X-3,Y-3, R¹-1,R²-1,Z-1,R³-3,1), (X-3,Y-3,R¹-1,R²-1,Z-1,R³-1,0), (X-3,Y-3,R¹-1,R²-1,Z-1,R³-1,1), (X-3,Y-3,R¹-1,R²-1,Z-2, R³-2,0), (X-3,Y-3,R¹-1,R²-1,Z-2,R³-2,1), (X-3,Y-3,R¹-1,R²-1,Z-2,R³-3,0), (X-3,Y-3,R¹-1,R²-1,Z-2,R³-3,1), (X-3,Y-3, R¹-1,R²-1,Z-2,R³-1,0), (X-3,Y-3,R¹-1,R²-1,Z-2,R³-1,1), (X-3,Y-3,R¹-1,R²-1,Z-2,R³-2,0), (X-3,Y-3,R¹-1,R²-1,Z-2, R³-2,1), (X-3,Y-3,R¹-1,R²-1,Z-3,R³-3,0), (X-3,Y-3,R¹-1,R²-1,Z-3,R³-3,1), (X-3,Y-3,R¹-1,R²-1,Z-3,R³-1,0), (X-3,Y-3, R¹-1,R²-1,Z-3,R³-1,1), (X-3,Y-3,R¹-1,R²-1,Z-3,R³-2,0), (X-3,Y-3,R¹-1,R²-1,Z-3,R³-2,1), (X-3,Y-3,R¹-1,R²-1,Z-3, R³-3,0), (X-3,Y-3,R¹-1,R²-1,Z-3,R³-3,1), (X-3,Y-5,R¹-1,R²-1,Z-1,R³-1,0), (X-3,Y-5,R¹-1,R²-1,Z-1,R³-1,1), (X-3,Y-5, R¹-1,R²-1,Z-1,R³-2,0), (X-3,Y-5,R¹-1,R²-1,Z-1,R³-2,1), (X-3,Y-5,R¹-1,R²-1,Z-1,R³-3,0), (X-3,Y-5,R¹-1,R²-1,Z-1, R³-3,1), (X-3,Y-5,R¹-1,R²-1,Z-1,R³-1,0), (X-3,Y-5,R¹-1,R²-1,Z-1,R³-1,1), (X-3,Y-5,R¹-1,R²-1,Z-2,R³-2,0), (X-3,Y-5, R¹-1,R²-1,Z-2,R³-2,1), (X-3,Y-5,R¹-1,R²-1,Z-2,R³-3,0), (X-3,Y-5,R¹-1,R²-1,Z-2,R³-3,1), (X-3,Y-5,R¹-1,R²-1,Z-2, R³-1,0), (X-3,Y-5,R¹-1,R²-1,Z-2,R³-1,1), (X-3,Y-5,R¹-1,R²-1,Z-2,R³-2,0), (X-3,Y-5,R¹-1,R²-1,Z-2,R³-2,1), (X-3,Y-5, R¹-1,R²-1,Z-3,R³-3,0), (X-3,Y-5,R¹-1,R²-1,Z-3,R³-3,1), (X-3,Y-5,R¹-1,R²-1,Z-3,R³-1,0), (X-3,Y-5,R¹-1,R²-1,Z-3, R³-1,1), (X-3,Y-5,R¹-1,R²-1,Z-3,R³-2,0), (X-3,Y-5,R¹-1,R²-1,Z-3,R³-2,1), (X-3,Y-5,R¹-1,R²-1,Z-3,R³-3,0), (X-3,Y-5, R¹-1,R²-1,Z-3,R³-3,1), (X-3,Y-6,R¹-1,R²-1,Z-1,R³-1,0), (X-3,Y-6,R¹-1,R²-1,Z-1,R³-1,1), (X-3,Y-6,R¹-1,R²-1,Z-1, R³-2,0), (X-3,Y-6,R¹-1,R²-1,Z-1,R³-2,1), (X-3,Y-6,R¹-1,R²-1,Z-1,R³-3,0), (X-3,Y-6,R¹-1,R²-1,Z-1,R³-3,1), (X-3,Y-6, R¹-1,R²-1,Z-1,R³-1,0), (X-3,Y-6,R¹-1,R²-1,Z-1,R³-1,1), (X-3,Y-6,R¹-1,R²-1,Z-2,R³-2,0), (X-3,Y-6,R¹-1,R²-1,Z-2, R³-2,1), (X-3,Y-6,R)-1,R²-1,Z-2,R³-3,0), (X-3,Y-6,R¹-1,R²-1,Z-2,R³-3,1), (X-3,Y-6,R¹-1,R²-1,Z-2,R³-1,0), (X-3,Y-6, R¹-1,R²-1,Z-2,R³-1,1), (X-3,Y-6,R¹-1,R²-1,Z-2,R³-2,0), (X-3,Y-6,R¹-1,R²-1,Z-2,R³-2,1), (X-3,Y-6,R¹-1,R²-1,Z-3, R³-3,0), (X-3,Y-6,R¹-1,R²-1,Z-3,R³-3,1), (X-3,Y-6,R¹-1,R²-1,Z-3,R³-1,0), (X-3,Y-6,R¹-1,R²-1,Z-3,R³-1,1), (X-3,Y-6, R¹-1,R²-1,Z-3,R³-2,0), (X-3,Y-6,R¹-1,R²-1,Z-3,R³-2,1), (X-3,Y-6,R¹-1,R²-1,Z-3,R³-3,0), (X-3,Y-6,R¹-1,R²-1,Z-3, R³-3,1), (X-3,Y-7,R¹-1,R²-1,Z-1,R³-1,0), (X-3,Y-7,R¹-1,R²-1,Z-1,R³-1,1), (X-3,Y-7,R¹-1,R²-1,Z-1,R³-2,0), (X-3,Y-7, R¹-1,R²-1,Z-1,R³-2,1), (X-3,Y-7,R¹-1,R²-1,Z-1,R³-3,0), (X-3,Y-7,R¹-1,R²-1,Z-1,R³-3,1), (X-3,Y-7,R¹-1,R²-1,Z-1, R³-1,0), (X-3,Y-7,R¹-1,R²-1,Z-1,R³-1,1), (X-3,Y-7,R¹-1,R²-1,Z-2,R³-2,0), (X-3,Y-7,R¹-1,R²-1,Z-2,R³-2,1), (X-3,Y-7, R¹-1,R²-1,Z-2,R³-3,0), (X-3,Y-7,R¹-1,R²-1,Z-2,R³-3,1), (X-3,Y-7,R¹-1,R²-1,Z-2,R³-1,0), (X-3,Y-7,R¹-1,R²-1,Z-2, R³-1,1), (X-3,Y-7,R¹-1,R²-1,Z-2,R³-2,0), (X-3,Y-7,R¹-

1,Z-2,R³-2,1), (X-3,Y-7,R¹-1,R²-1,Z-3,R³-3,0), (X-3,Y-7,R¹-1,R²-1,Z-3,R³-3,1), (X-3,Y-7,R¹-1,R²-1,Z-3,R³-1,0), (X-3,Y-7,R¹-1,R²-1,Z-3,R³-1,1), (X-3,Y-7,R¹-1,R²-1,Z-3,R³-2,0), (X-3,Y-7,R¹-1,R²-1,Z-3,R³-2,1), (X-3,Y-7,R¹-1,R²-1,Z-3,R³-3,0), (X-3,Y-7,R¹-1,R²-1,Z-3,R³-3,1), (X-3,Y-7,R¹-2,R²-1,Z-1,R³-1,0), (X-3,Y-7,R¹-2,R²-1,Z-1,R³-1,1), (X-3,Y-7,R¹-2,R²-1,Z-1,R³-2,0), (X-3,Y-7,R¹-2,R²-1,Z-1,R³-2,1), (X-3,Y-7,R¹-2,R²-1,Z-1,R³-3,0), (X-3,Y-7,R¹-2,R²-1,Z-1,R³-3,1), (X-3,Y-7,R¹-2,R²-1,Z-1,R³-1,0), (X-3,Y-7,R¹-2,R²-1,Z-1,R³-1,1), (X-3,Y-7,R¹-2,R²-1,Z-2,R³-2,0), (X-3,Y-7,R¹-2,R²-1,Z-2,R³-2,1), (X-3,Y-7,R¹-2,R²-1,Z-2,R³-3,0), (X-3,Y-7,R¹-2,R²-1,Z-2,R³-3,1), (X-3,Y-7,R¹-2,R²-1,Z-2,R³-1,0), (X-3,Y-7,R¹-2,R²-1,Z-2,R³-1,1), (X-3,Y-7,R¹-2,R²-1,Z-2,R³-2,0), (X-3,Y-7,R¹-2,R²-1,Z-2,R³-2,1), (X-3,Y-7,R¹-2,R²-1,Z-3,R³-3,0), (X-3,Y-7,R¹-2,R²-1,Z-3,R³-3,1), (X-3,Y-7,R¹-2,R²-1,Z-3,R³-1,0), (X-3,Y-7,R¹-2,R²-1,Z-3,R³-1,1), (X-3,Y-7,R¹-2,R²-1,Z-3,R³-2,0), (X-3,Y-7,R¹-2,R²-1,Z-3,R³-2,1), (X-3,Y-7,R¹-2,R²-1,Z-3,R³-3,0), (X-3,Y-7,R¹-2,R²-1,Z-3,R³-3,1)

(X-8,Y-3,R¹-1,R²-1,Z-1,R³-1,0), (X-8,Y-3,R¹-1,R²-1,Z-1,R³-1,1), (X-8,Y-3,R¹-1,R²-1,Z-1,R³-2,0), (X-8,Y-3,R¹-1,R²-1,Z-1,R³-2,1), (X-8,Y-3,R¹-1,R²-1,Z-1,R³-3,0), (X-8,Y-3,R¹-1,R²-1,Z-1,R³-3,1), (X-8,Y-3,R¹-1,R²-1,Z-1,R³-1,0), (X-8,Y-3,R¹-1,R²-1,Z-1,R³-1,1), (X-8,Y-3,R¹-1,R²-1,Z-2,R³-2,0), (X-8,Y-3,R¹-1,R²-1,Z-2,R³-2,1), (X-8,Y-3,R¹-1,R²-1,Z-2,R³-3,0), (X-8,Y-3,R¹-1,R²-1,Z-2,R³-3,1), (X-8,Y-3,R¹-1,R²-1,Z-2,R³-1,0), (X-8,Y-3,R¹-1,R²-1,Z-2,R³-1,1), (X-8,Y-3,R¹-1,R²-1,Z-2,R³-2,0), (X-8,Y-3,R¹-1,R²-1,Z-2,R³-2,1), (X-8,Y-3,R¹-1,R²-1,Z-3,R³-3,0), (X-8,Y-3,R¹-1,R²-1,Z-3,R³-3,1), (X-8,Y-3,R¹-1,R²-1,Z-3,R³-1,0), (X-8,Y-3,R¹-1,R²-1,Z-3,R³-1,1), (X-8,Y-3,R¹-1,R²-1,Z-3,R³-2,0), (X-8,Y-3,R¹-1,R²-1,Z-3,R³-2,1), (X-8,Y-3,R¹-1,R²-1,Z-3,R³-3,0), (X-8,Y-3,R¹-1,R²-1,Z-3,R³-3,1), (X-8,Y-3,R¹-2,R²-1,Z-1,R³-1,0), (X-8,Y-3,R¹-2,R²-1,Z-1,R³-1,1), (X-8,Y-3,R¹-2,R²-1,Z-1,R³-2,0), (X-8,Y-3,R¹-2,R²-1,Z-1,R³-2,1), (X-8,Y-3,R¹-2,R²-1,Z-1,R³-3,0), (X-8,Y-3,R¹-2,R²-1,Z-1,R³-3,1), (X-8,Y-3,R¹-2,R²-1,Z-1,R³-1,0), (X-8,Y-3,R¹-2,R²-1,Z-1,R³-1,1), (X-8,Y-3,R¹-2,R²-1,Z-2,R³-2,0), (X-8,Y-3,R¹-2,R²-1,Z-2,R³-2,1), (X-8,Y-3,R¹-2,R²-1,Z-2,R³-3,0), (X-8,Y-3,R¹-2,R²-1,Z-2,R³-3,1), (X-8,Y-3,R¹-2,R²-1,Z-2,R³-1,0), (X-8,Y-3,R¹-2,R²-1,Z-2,R³-1,1), (X-8,Y-3,R¹-2,R²-1,Z-2,R³-2,0), (X-8,Y-3,R¹-2,R²-1,Z-2,R³-2,1), (X-8,Y-3,R¹-2,R²-1,Z-3,R³-3,0), (X-8,Y-3,R¹-2,R²-1,Z-3,R³-3,1), (X-8,Y-3,R¹-2,R²-1,Z-3,R³-1,0), (X-8,Y-3,R¹-2,R²-1,Z-3,R³-1,1), (X-8,Y-3,R¹-2,R²-1,Z-3,R³-2,0), (X-8,Y-3,R¹-2,R²-1,Z-3,R³-2,1), (X-8,Y-3,R¹-2,R²-1,Z-3,R³-3,0), (X-8,Y-3,R¹-2,R²-1,Z-3,R³-3,1), (X-8,Y-5,R¹-1,R²-1,Z-1,R³-1,0), (X-8,Y-5,R¹-1,R²-1,Z-1,R³-1,1), (X-8,Y-5,R¹-1,R²-1,Z-1,R³-2,0), (X-8,Y-5,R¹-1,R²-1,Z-1,R³-2,1), (X-8,Y-5,R¹-1,R²-1,Z-1,R³-3,0), (X-8,Y-5,R¹-1,R²-1,Z-1,R³-3,1), (X-8,Y-5,R¹-1,R²-1,Z-1,R³-1,0), (X-8,Y-5,R¹-1,R²-1,Z-1,R³-1,1), (X-8,Y-5,R¹-1,R²-1,Z-2,R³-2,0), (X-8,Y-5,R¹-1,R²-1,Z-2,R³-2,1), (X-8,Y-5,R¹-1,R²-1,Z-2,R³-3,0), (X-8,Y-5,R¹-1,R²-1,Z-2,R³-3,1), (X-8,Y-5,R¹-1,R²-1,Z-2,R³-1,0), (X-8,Y-5,R¹-1,R²-1,Z-2,R³-1,1), (X-8,Y-5,R¹-1,R²-1,Z-2,R³-2,0), (X-8,Y-5,R¹-1,R²-1,Z-2,R³-2,1), (X-8,Y-5,R¹-1,R²-1,Z-3,R³-3,0), (X-8,Y-5,R¹-1,R²-1,Z-3,R³-3,1), (X-8,Y-5,R¹-1,R²-1,Z-3,R³-1,0), (X-8,Y-5,R¹-1,R²-1,Z-3,R³-1,1), (X-8,Y-5,R¹-1,R²-1,Z-3,R³-2,0), (X-8,Y-5,R¹-1,R²-1,Z-3,R³-2,1), (X-8,Y-5,R¹-1,R²-1,Z-3,R³-3,0), (X-8,Y-5,R¹-1,R²-1,Z-3,R³-3,1), (X-8,Y-5,R¹-2,R²-1,Z-1,R³-1,0), (X-8,Y-5,R¹-2,R²-1,Z-1,R³-1,1), (X-8,Y-5,R¹-2,R²-1,Z-1,R³-2,0), (X-8,Y-5,R¹-2,R²-1,Z-1,R³-2,1), (X-8,Y-5,R¹-2,R²-1,Z-1,R³-3,0), (X-8,Y-5,R¹-2,R²-1,Z-1,R³-3,1), (X-8,Y-5,R¹-2,R²-1,Z-2,R³-1,0), (X-8,Y-5,R¹-2,R²-1,Z-2,R³-1,1), (X-8,Y-5,R¹-2,R²-1,Z-2,R³-2,0), (X-8,Y-5,R¹-2,R²-1,Z-2,R³-2,1), (X-8,Y-5,R¹-2,R²-1,Z-2,R³-3,0), (X-8,Y-5,R¹-2,R²-1,Z-2,R³-3,1), (X-8,Y-5,R¹-2,R²-1,Z-2,R³-1,0), (X-8,Y-5,R¹-2,R²-1,Z-2,R³-1,1), (X-8,Y-5,R¹-2,R²-1,Z-2,R³-2,0), (X-8,Y-5,R¹-2,R²-1,Z-2,R³-2,1), (X-8,Y-5,R¹-2,R²-1,Z-3,R³-3,0), (X-8,Y-5,R¹-2,R²-1,Z-3,R³-3,1), (X-8,Y-5,R¹-2,R²-1,Z-3,R³-1,0), (X-8,Y-5,R¹-2,R²-1,Z-3,R³-1,1), (X-8,Y-5,R¹-2,R²-1,Z-3,R³-2,0), (X-8,Y-5,R¹-2,R²-1,Z-3,R³-2,1), (X-8,Y-5,R¹-2,R²-1,Z-3,R³-3,0), (X-8,Y-5,R¹-2,R²-1,Z-3,R³-3,1), (X-8,Y-6,R¹-1,R²-1,Z-1,R³-1,0), (X-8,Y-6,R¹-1,R²-1,Z-1,R³-1,1), (X-8,Y-6,R¹-1,R²-1,Z-1,R³-2,0), (X-8,Y-6,R¹-1,R²-1,Z-1,R³-2,1), (X-8,Y-6,R¹-1,R²-1,Z-1,R³-3,0), (X-8,Y-6,R¹-1,R²-1,Z-1,R³-3,1), (X-8,Y-6,R¹-1,R²-1,Z-1,R³-1,0), (X-8,Y-6,R¹-1,R²-1,Z-1,R³-1,1), (X-8,Y-6,R¹-1,R²-1,Z-2,R³-2,0), (X-8,Y-6,R¹-1,R²-1,Z-2,R³-2,1), (X-8,Y-6,R¹-1,R²-1,Z-2,R³-3,0), (X-8,Y-6,R¹-1,R²-1,Z-2,R³-3,1), (X-8,Y-6,R¹-1,R²-1,Z-2,R³-1,0), (X-8,Y-6,R¹-1,R²-1,Z-2,R³-1,1), (X-8,Y-6,R¹-1,R²-1,Z-2,R³-2,0), (X-8,Y-6,R¹-1,R²-1,Z-2,R³-2,1), (X-8,Y-6,R¹-1,R²-1,Z-3,R³-3,0), (X-8,Y-6,R¹-1,R²-1,Z-3,R³-3,1), (X-8,Y-6,R¹-1,R²-1,Z-3,R³-1,0), (X-8,Y-6,R¹-1,R²-1,Z-3,R³-1,1), (X-8,Y-6,R¹-1,R²-1,Z-3,R³-2,0), (X-8,Y-6,R¹-1,R²-1,Z-3,R³-2,1), (X-8,Y-6,R¹-1,R²-1,Z-3,R³-3,0), (X-8,Y-6,R¹-1,R²-1,Z-3,R³-3,1), (X-8,Y-6,R¹-2,R²-1,Z-1,R³-1,0), (X-8,Y-6,R¹-2,R²-1,Z-1,R³-1,1), (X-8,Y-6,R¹-2,R²-1,Z-1,R³-2,0), (X-8,Y-6,R¹-2,R²-1,Z-1,R³-2,1), (X-8,Y-6,R¹-2,R²-1,Z-1,R³-3,0), (X-8,Y-6,R¹-2,R²-1,Z-1,R³-3,1), (X-8,Y-6,R¹-2,R²-1,Z-1,R³-1,0), (X-8,Y-6,R¹-2,R²-1,Z-1,R³-1,1), (X-8,Y-6,R¹-2,R²-1,Z-2,R³-2,0), (X-8,Y-6,R¹-2,R²-1,Z-2,R³-2,1), (X-8,Y-6,R¹-2,R²-1,Z-2,R³-3,0), (X-8,Y-6,R¹-2,R²-1,Z-2,R³-3,1), (X-8,Y-6,R¹-2,R²-1,Z-2,R³-1,0), (X-8,Y-6,R¹-2,R²-1,Z-2,R³-1,1), (X-8,Y-6,R¹-2,R²-1,Z-2,R³-2,0), (X-8,Y-6,R¹-2,R²-1,Z-2,R³-2,1), (X-8,Y-6,R¹-2,R²-1,Z-3,R³-3,0), (X-8,Y-6,R¹-2,R²-1,Z-3,R³-3,1), (X-8,Y-6,R¹-2,R²-1,Z-3,R³-1,0), (X-8,Y-6,R¹-2,R²-1,Z-3,R³-1,1), (X-8,Y-6,R¹-2,R²-1,Z-3,R³-2,0), (X-8,Y-6,R¹-2,R²-1,Z-3,R³-2,1), (X-8,Y-6,R¹-2,R²-1,Z-3,R³-3,0), (X-8,Y-6,R¹-2,R²-1,Z-3,R³-3,1), (X-8,Y-7,R¹-1,R²-1,Z-1,R³-1,0), (X-8,Y-7,R¹-1,R²-1,Z-1,R³-1,1), (X-8,Y-7,R¹-1,R²-1,Z-1,R³-2,0), (X-8,Y-7,R¹-1,R²-1,Z-1,R³-2,1), (X-8,Y-7,R¹-1,R²-1,Z-1,R³-1,0), (X-8,Y-7,R¹-1,R²-1,Z-1,R³-1,1), (X-8,Y-7,R¹-1,R²-1,Z-2,R³-2,0), (X-8,Y-7,R¹-1,R²-1,Z-2,R³-2,1), (X-8,Y-7,R¹-1,R²-1,Z-2,R³-3,0), (X-8,Y-7,R¹-1,R²-1,Z-2,R³-3,1), (X-8,Y-7,R¹-1,R²-1,Z-2,R³-1,0), (X-8,Y-7,R¹-1,R²-1,Z-2,R³-1,1), (X-8,Y-7,R¹-1,R²-1,Z-2,R³-2,0), (X-8,Y-7,R¹-1,R²-1,Z-2,R³-2,1), (X-8,Y-7,R¹-1,R²-1,Z-3,R³-3,0), (X-8,Y-7,R¹-1,R²-1,Z-3,R³-3,1), (X-8,Y-7,R¹-1,R²-1,Z-3,R³-1,0), (X-8,Y-7,R¹-1,R²-1,Z-3,R³-1,1), (X-8,Y-7,R¹-1,R²-1,Z-3,R³-2,0), (X-8,Y-7,R¹-1,R²-1,Z-3,R³-2,1), (X-8,Y-7,R¹-1,R²-1,Z-3,R³-3,0), (X-8,Y-7,R¹-1,R²-1,Z-3,R³-3,1), (X-8,Y-7,R¹-2,R²-1,Z-1,R³-1,0), (X-8,Y-7,R¹-2,R²-1,Z-1,R³-1,1), (X-8,Y-7,R¹-2,R²-1,Z-1,R³-2,0), (X-8,Y-7,R¹-2,R²-1,Z-1,R³-2,1), (X-8,Y-7,R¹-2,R²-1,Z-1,R³-3,0), (X-8,Y-7,R¹-2,R²-1,Z-1,R³-3,1), (X-8,Y-7,R¹-2,R²-1,Z-1,R³-1,0), (X-8,Y-7,R¹-2,R²-1,Z-1,R³-1,1), (X-8,Y-7,R¹-2,R²-1,Z-2,R³-2,0), (X-8,Y-7,R¹-2,R²-1,Z-2,R³-3,0), (X-8,Y-7,R¹-2,R²-1,Z-2,R³-1,0), (X-8,Y-7,R¹-2,R²-1,Z-2,R³-2,0), (X-8,Y-7,R¹-2,R²-1,Z-3,R³-3,0), (X-8,Y-7,R¹-2,R²-1,Z-3,R³-1,0), (X-8,Y-7,R¹-2,R²-1,Z-3,R³-2,0), (X-8,Y-7,R¹-2,R²-1,Z-3,R³-3,0)

(X-10,Y-3,R¹-1,R²-1,Z-1,R³-1,0), (X-10,Y-3,R¹-1,R²-1,Z-1,R³-1,1), (X-10,Y-3,R¹-1,R²-1,Z-1,R³-2,0), (X-10,Y-3,R¹-1,R²-1,Z-1,R³-2,1), (X-10,Y-3,R¹-1,R²-1,Z-1,R³-3,0), (X-10,Y-3,R¹-1,R²-1,Z-1,R³-3,1), (X-10,Y-3,R¹-1,R²-1,Z-1,R³-1,0), (X-10,Y-3,R¹-1,R²-1,Z-1,R³-1,1), (X-10,Y-3,R¹-1,R²-1,Z-2,R³-2,0), (X-10,Y-3,R¹-1,R²-1,Z-2,R³-2,1), (X-10,Y-3,R¹-1,R²-1,Z-2,R³-3,0), (X-10,Y-3,R¹-1,R²-1,Z-2,R³-3,1), (X-10,Y-3,R¹-1,R²-1,Z-2,R³-1,0), (X-10,Y-3,R¹-1,R²-1,Z-2,R³-1,1), (X-10,Y-3,R¹-1,R²-1,Z-2,R³-2,0), (X-10,Y-3,R¹-1,R²-1,Z-2,R³-2,1), (X-10,Y-3,R¹-1,R²-1,Z-3,R³-3,0), (X-10,Y-3,R¹-1,R²-1,Z-3,R³-3,1), (X-10,Y-3,R¹-1,R²-1,Z-3, $R^3$-1,0), (X-10,Y-3,$R^1$-1,$R^2$-1,Z-3,$R^3$-1,1), (X-10,Y-3,$R^1$-1,$R^2$-1,Z-3,$R^3$-2,0), (X-10,Y-3,$R^1$-1,$R^2$-1,Z-3,$R^3$-2,1), (X-10,Y-3,$R^1$-1,$R^2$-1,Z-3,$R^3$-3,0), (X-10,Y-3,$R^1$-1,$R^2$-1,Z-3,$R^3$-3,1), (X-10,Y-3,$R^1$-2,$R^2$-1,Z-1,$R^3$-1,0), (X-10,Y-3,$R^1$-2,$R^2$-1,Z-1,$R^3$-1,1), (X-10,Y-3,$R^1$-2,$R^2$-1,Z-1,$R^3$-2,0), (X-10,Y-3,$R^1$-2,$R^2$-1,Z-1,$R^3$-2,1), (X-10,Y-3,$R^1$-2,$R^2$-1,Z-1,$R^3$-3,0), (X-10,Y-3,$R^1$-2,$R^2$-1,Z-1,$R^3$-3,1), (X-10,Y-3,$R^1$-2,$R^2$-1,Z-1,$R^3$-1,0), (X-10,Y-3,$R^1$-2,$R^2$-1,Z-1,$R^3$-1,1), (X-10,Y-3,$R^1$-2,$R^2$-1,Z-2,$R^3$-2,0), (X-10,Y-3,$R^1$-2,$R^2$-1,Z-2,$R^3$-2,1), (X-10,Y-3,$R^1$-2,$R^2$-1,Z-2,$R^3$-3,0), (X-10,Y-3,$R^1$-2,$R^2$-1,Z-2,$R^3$-3,1), (X-10,Y-3,$R^1$-2,$R^2$-1,Z-2,$R^3$-1,0), (X-10,Y-3,$R^1$-2,$R^2$-1,Z-2,$R^3$-1,1), (X-10,Y-3,$R^1$-2,$R^2$-1,Z-2,$R^3$-2,0), (X-10,Y-3,$R^1$-2,$R^2$-1,Z-2,$R^3$-2,1), (X-10,Y-3,$R^1$-2,$R^2$-1,Z-3,$R^3$-3,0), (X-10,Y-3,$R^1$-2,$R^2$-1,Z-3,$R^3$-3,1), (X-10,Y-3,$R^1$-2,$R^2$-1,Z-3,$R^3$-1,0), (X-10,Y-3,$R^1$-2,$R^2$-1,Z-3,$R^3$-1,1), (X-10,Y-3,$R^1$-2,$R^2$-1,Z-3,$R^3$-2,0), (X-10,Y-3,$R^1$-2,$R^2$-1,Z-3,$R^3$-2,1), (X-10,Y-3,$R^1$-2,$R^2$-1,Z-3,$R^3$-3,0), (X-10,Y-3,$R^1$-2,$R^2$-1,Z-3,$R^3$-3,1), (X-10,Y-5,$R^1$-1,$R^2$-1,Z-1,$R^3$-1,0), (X-10,Y-5,$R^1$-1,$R^2$-1,Z-1,$R^3$-1,1), (X-10,Y-5,$R^1$-1,$R^2$-1,Z-1,$R^3$-2,0), (X-10,Y-5,$R^1$-1,$R^2$-1,Z-1,$R^3$-2,1), (X-10,Y-5,$R^1$-1,$R^2$-1,Z-1,$R^3$-3,0), (X-10,Y-5,$R^1$-1,$R^2$-1,Z-1,$R^3$-3,1), (X-10,Y-5,$R^1$-1,$R^2$-1,Z-1,$R^3$-1,0), (X-10,Y-5,$R^1$-1,$R^2$-1,Z-1,$R^3$-1,1), (X-10,Y-5,$R^1$-1,$R^2$-1,Z-2,$R^3$-2,0), (X-10,Y-5,$R^1$-1,$R^2$-1,Z-2,$R^3$-2,1), (X-10,Y-5,$R^1$-1,$R^2$-1,Z-2,$R^3$-3,0), (X-10,Y-5,$R^1$-1,$R^2$-1,Z-2,$R^3$-3,1), (X-10,Y-5,$R^1$-1,$R^2$-1,Z-2,$R^3$-1,0), (X-10,Y-5,$R^1$-1,$R^2$-1,Z-2,$R^3$-1,1), (X-10,Y-5,$R^1$-1,$R^2$-1,Z-2,$R^3$-2,0), (X-10,Y-5,$R^1$-1,$R^2$-1,Z-2,$R^3$-2,1), (X-10,Y-5,$R^1$-1,$R^2$-1,Z-3,$R^3$-3,0), (X-10,Y-5,$R^1$-1,$R^2$-1,Z-3,$R^3$-3,1), (X-10,Y-5,$R^1$-1,$R^2$-1,Z-3,$R^3$-1,0), (X-10,Y-5,$R^1$-1,$R^2$-1,Z-3,$R^3$-1,1), (X-10,Y-5,$R^1$-1,$R^2$-1,Z-3,$R^3$-2,0), (X-10,Y-5,$R^1$-1,$R^2$-1,Z-3,$R^3$-2,1), (X-10,Y-5,$R^1$-1,$R^2$-1,Z-3,$R^3$-3,0), (X-10,Y-5,$R^1$-1,$R^2$-1,Z-3,$R^3$-3,1), (X-10,Y-5,$R^1$-2,$R^2$-1,Z-1,$R^3$-1,0), (X-10,Y-5,$R^1$-2,$R^2$-1,Z-1,$R^3$-1,1), (X-10,Y-5,$R^1$-2,$R^2$-1,Z-1,$R^3$-2,0), (X-10,Y-5,$R^1$-2,$R^2$-1,Z-1,$R^3$-2,1), (X-10,Y-5,$R^1$-2,$R^2$-1,Z-1,$R^3$-3,0), (X-10,Y-5,$R^1$-2,$R^2$-1,Z-1,$R^3$-3,1), (X-10,Y-5,$R^1$-2,$R^2$-1,Z-1,$R^3$-1,0), (X-10,Y-5,$R^1$-2,$R^2$-1,Z-1,$R^3$-1,1), (X-10,Y-5,$R^1$-2,$R^2$-1,Z-2,$R^3$-2,0), (X-10,Y-5,$R^1$-2,$R^2$-1,Z-2,$R^3$-2,1), (X-10,Y-5,$R^1$-2,$R^2$-1,Z-2,$R^3$-3,0), (X-10,Y-5,$R^1$-2,$R^2$-1,Z-2,$R^3$-3,1), (X-10,Y-5,$R^1$-2,$R^2$-1,Z-2,$R^3$-1,0), (X-10,Y-5,$R^1$-2,$R^2$-1,Z-2,$R^3$-1,1), (X-10,Y-5,$R^1$-2,$R^2$-1,Z-2,$R^3$-2,0), (X-10,Y-5,$R^1$-2,$R^2$-1,Z-2,$R^3$-2,1), (X-10,Y-5,$R^1$-2,$R^2$-1,Z-3,$R^3$-3,0), (X-10,Y-5,$R^1$-2,$R^2$-1,Z-3,$R^3$-3,1), (X-10,Y-5,$R^1$-2,$R^2$-1,Z-3,$R^3$-1,0), (X-10,Y-5,$R^1$-2,$R^2$-1,Z-3,$R^3$-1,1), (X-10,Y-5,$R^1$-2,$R^2$-1,Z-3,$R^3$-2,0), (X-10,Y-5,$R^1$-2,$R^2$-1,Z-3,$R^3$-2,1), (X-10,Y-5,$R^1$-2,$R^2$-1,Z-3,$R^3$-3,0), (X-10,Y-5,$R^1$-2,$R^2$-1,Z-3,$R^3$-3,1), (X-10,Y-6,$R^1$-1,$R^2$-1,Z-1,$R^3$-1,0), (X-10,Y-6,$R^1$-1,$R^2$-1,Z-1,$R^3$-1,1), (X-10,Y-6,$R^1$-1,$R^2$-1,Z-1,$R^3$-2,0), (X-10,Y-6,$R^1$-1,$R^2$-1,Z-1,$R^3$-2,1), (X-10,Y-6,$R^1$-1,$R^2$-1,Z-1,$R^3$-3,0), (X-10,Y-6,$R^1$-1,$R^2$-1,Z-1,$R^3$-3,1), (X-10,Y-6,$R^1$-1,$R^2$-1,Z-1,$R^3$-1,0), (X-10,Y-6,$R^1$-1,$R^2$-1,Z-1,$R^3$-1,1), (X-10,Y-6,$R^1$-1,$R^2$-1,Z-2,$R^3$-2,0), (X-10,Y-6,$R^1$-1,$R^2$-1,Z-2,$R^3$-2,1), (X-10,Y-6,$R^1$-1,$R^2$-1,Z-2,$R^3$-3,0), (X-10,Y-6,$R^1$-1,$R^2$-1,Z-2,$R^3$-3,1), (X-10,Y-6,$R^1$-1,$R^2$-1,Z-2,$R^3$-1,0), (X-10,Y-6,$R^1$-1,$R^2$-1,Z-2,$R^3$-1,1), (X-10,Y-6,$R^1$-1,$R^2$-1,Z-2,$R^3$-2,0), (X-10,Y-6,$R^1$-1,$R^2$-1,Z-2,$R^3$-2,1), (X-10,Y-6,$R^1$-1,$R^2$-1,Z-3,$R^3$-3,0), (X-10,Y-6,$R^1$-1,$R^2$-1,Z-3,$R^3$-3,1), (X-10,Y-6,$R^1$-1,$R^2$-1,Z-3,$R^3$-1,0), (X-10,Y-6,$R^1$-1,$R^2$-1,Z-3,$R^3$-1,1), (X-10,Y-6,$R^1$-1,$R^2$-1,Z-3,$R^3$-2,0), (X-10,Y-6,$R^1$-1,$R^2$-1,Z-3,$R^3$-2,1), (X-10,Y-6,$R^1$-1,$R^2$-1,Z-3,$R^3$-3,0), (X-10,Y-6,$R^1$-1,$R^2$-1,Z-3,$R^3$-3,1), (X-10,Y-6,$R^1$-2,$R^2$-1,Z-1,$R^3$-1,0), (X-10,Y-6,$R^1$-2,$R^2$-1,Z-1,$R^3$-1,1), (X-10,Y-6,$R^1$-2,$R^2$-1,Z-1,$R^3$-2,0), (X-10,Y-6,$R^1$-2,$R^2$-1,Z-1,$R^3$-2,1), (X-10,Y-6,$R^1$-2,$R^2$-1,Z-1,$R^3$-3,0), (X-10,Y-6,$R^1$-2,$R^2$-1,Z-1,$R^3$-3,1), (X-10,Y-6,$R^1$-2,$R^2$-1,Z-1,$R^3$-1,0), (X-10,Y-6,$R^1$-2,$R^2$-1,Z-1,$R^3$-1,1), (X-10,Y-6,$R^1$-2,$R^2$-1,Z-2,$R^3$-2,0), (X-10,Y-6,$R^1$-2,$R^2$-1,Z-2,$R^3$-2,1), (X-10,Y-6,$R^1$-2,$R^2$-1,Z-2,$R^3$-3,0), (X-10,Y-6,$R^1$-2,$R^2$-1,Z-2,$R^3$-3,1), (X-10,Y-6,$R^1$-2,$R^2$-1,Z-2,$R^3$-1,0), (X-10,Y-6,$R^1$-2,$R^2$-1,Z-2,$R^3$-1,1), (X-10,Y-6,$R^1$-2,$R^2$-1,Z-2,$R^3$-2,0), (X-10,Y-6,$R^1$-2,$R^2$-1,Z-2,$R^3$-2,1), (X-10,Y-6,$R^1$-2,$R^2$-1,Z-3,$R^3$-3,0), (X-10,Y-6,$R^1$-2,$R^2$-1,Z-3,$R^3$-3,1), (X-10,Y-6,$R^1$-2,$R^2$-1,Z-3,$R^3$-1,0), (X-10,Y-6,$R^1$-2,$R^2$-1,Z-3,$R^3$-1,1), (X-10,Y-6,$R^1$-2,$R^2$-1,Z-3,$R^3$-2,0), (X-10,Y-6,$R^1$-2,$R^2$-1,Z-3,$R^3$-2,1), (X-10,Y-6,$R^1$-2,$R^2$-1,Z-3,$R^3$-3,0), (X-10,Y-6,$R^1$-2,$R^2$-1,Z-3,$R^3$-3,1), (X-10,Y-7,$R^1$-1,$R^2$-1,Z-1,$R^3$-1,0), (X-10,Y-7,$R^1$-1,$R^2$-1,Z-1,$R^3$-1,1), (X-10,Y-7,$R^1$-1,$R^2$-1,Z-1,$R^3$-2,0), (X-10,Y-7,$R^1$-1,$R^2$-1,Z-1,$R^3$-2,1), (X-10,Y-7,$R^1$-1,$R^2$-1,Z-2,$R^3$-2,0), (X-10,Y-7,$R^1$-1,$R^2$-1,Z-2,$R^3$-2,1), (X-10,Y-7,$R^1$-1,$R^2$-1,Z-2,$R^3$-3,0), (X-10,Y-7,$R^1$-1,$R^2$-1,Z-2,$R^3$-3,1), (X-10,Y-7,$R^1$-1,$R^2$-1,Z-2,$R^3$-1,0), (X-10,Y-7,$R^1$-1,$R^2$-1,Z-2,$R^3$-1,1), (X-10,Y-7,$R^1$-1,$R^2$-1,Z-2,$R^3$-2,0), (X-10,Y-7,$R^1$-1,$R^2$-1,Z-2,$R^3$-2,1), (X-10,Y-7,$R^1$-1,$R^2$-1,Z-3,$R^3$-3,0), (X-10,Y-7,$R^1$-1,$R^2$-1,Z-3,$R^3$-3,1), (X-10,Y-7,$R^1$-1,$R^2$-1,Z-3,$R^3$-1,0), (X-10,Y-7,$R^1$-1,$R^2$-1,Z-3,$R^3$-1,1), (X-10,Y-7,$R^1$-1,$R^2$-1,Z-3,$R^3$-2,0), (X-10,Y-7,$R^1$-1,$R^2$-1,Z-3,$R^3$-2,1), (X-10,Y-7,$R^1$-1,$R^2$-1,Z-3,$R^3$-3,0), (X-10,Y-7,$R^1$-1,$R^2$-1,Z-3,$R^3$-3,1), (X-10,Y-7,$R^1$-2,$R^2$-1,Z-1,$R^3$-1,0), (X-10,Y-7,$R^1$-2,$R^2$-1,Z-1,$R^3$-1,1), (X-10,Y-7,$R^1$-2,$R^2$-1,Z-1,$R^3$-2,0), (X-10,Y-7,$R^1$-2,$R^2$-1,Z-1,$R^3$-2,1), (X-10,Y-7,$R^1$-2,$R^2$-1,Z-1,$R^3$-3,0), (X-10,Y-7,$R^1$-2,$R^2$-1,Z-1,$R^3$-3,1), (X-10,Y-7,$R^1$-2,$R^2$-1,Z-1,$R^3$-1,0), (X-10,Y-7,$R^1$-2,$R^2$-1,Z-1,$R^3$-1,1), (X-10,Y-7,$R^1$-2,$R^2$-1,Z-2,$R^3$-2,0), (X-10,Y-7,$R^1$-2,$R^2$-1,Z-2,$R^3$-2,1), (X-10,Y-7,$R^1$-2,$R^2$-1,Z-2,$R^3$-3,0), (X-10,Y-7,$R^1$-2,$R^2$-1,Z-2,$R^3$-3,1), (X-10,Y-7,$R^1$-2,$R^2$-1,Z-2,$R^3$-1,0), (X-10,Y-7,$R^1$-2,$R^2$-1,Z-2,$R^3$-1,1), (X-10,Y-7,$R^1$-2,$R^2$-1,Z-2,$R^3$-2,0), (X-10,Y-7,$R^1$-2,$R^2$-1,Z-2,$R^3$-2,1), (X-10,Y-7,$R^1$-2,$R^2$-1,Z-3,$R^3$-3,0), (X-10,Y-7,$R^1$-2,$R^2$-1,Z-3,$R^3$-3,1), (X-10,Y-7,$R^1$-2,$R^2$-1,Z-3,$R^3$-1,0), (X-10,Y-7,$R^1$-2,$R^2$-1,Z-3,$R^3$-1,1), (X-10,Y-7,$R^1$-2,$R^2$-1,Z-3,$R^3$-2,0), (X-10,Y-7,$R^1$-2,$R^2$-1,Z-3,$R^3$-2,1), (X-10,Y-7,$R^1$-2,$R^2$-1,Z-3,$R^3$-3,0), (X-10,Y-7,$R^1$-2,$R^2$-1,Z-3,$R^3$-3,1)

(X-11,Y-3,$R^1$-1,$R^2$-1,Z-1,$R^3$-1,0), (X-11,Y-3,$R^1$-1,$R^2$-1,Z-1,$R^3$-1,1), (X-11,Y-3,$R^1$-1,$R^2$-1,Z-1,$R^3$-2,0), (X-11,Y-3,$R^1$-1,$R^2$-1,Z-1,$R^3$-2,1), (X-11,Y-3,$R^1$-1,$R^2$-1,Z-1,$R^3$-3,0), (X-11,Y-3,$R^1$-1,$R^2$-1,Z-1,$R^3$-3,1), (X-11,Y-3,$R^1$-1,$R^2$-1,Z-1,$R^3$-1,0), (X-11,Y-3,$R^1$-1,$R^2$-1,Z-1,$R^3$-1,1), (X-11,Y-3,$R^1$-1,$R^2$-1,Z-2,$R^3$-2,0), (X-11,Y-3,$R^1$-1,$R^2$-1,Z-2,$R^3$-2,1), (X-11,Y-3,$R^1$-1,$R^2$-1,Z-2,$R^3$-3,0), (X-11,Y-3,$R^1$-1,$R^2$-1,Z-2,$R^3$-3,1), (X-11,Y-3,$R^1$-1,$R^2$-1,Z-2,$R^3$-1,0), (X-11,Y-3,$R^1$-1,$R^2$-1,Z-2,$R^3$-1,1), (X-11,Y-3,$R^1$-1,$R^2$-1,Z-2,$R^3$-2,0), (X-11,Y-3,$R^1$-1,$R^2$-1,Z-2,$R^3$-2,1), (X-11,Y-3,$R^1$-1,$R^2$-1,Z-3,$R^3$-3,0), (X-11,Y-3,$R^1$-1,$R^2$-1,Z-3,$R^3$-3,1), (X-11,Y-3,$R^1$-1,$R^2$-1,Z-3,$R^3$-1,0), (X-11,Y-3,$R^1$-1,$R^2$-1,Z-3,$R^3$-1,1), (X-11,Y-3,$R^1$-1,$R^2$-1,Z-3,$R^3$-2,0), (X-11,Y-3,$R^1$-1,$R^2$-1,Z-3,$R^3$-2,1), (X-11,Y-3,$R^1$-1,$R^2$-1,Z-3,$R^3$-3,0), (X-11,Y-3,$R^1$-1,$R^2$-1,Z-3,$R^3$-3,1), (X-11,Y-3,$R^1$-2,$R^2$-1,Z-1,$R^3$-1,0), (X-11,Y-3,$R^1$-2,$R^2$-1,Z-1,$R^3$-1,1), (X-11,Y-3,$R^1$-2,$R^2$-1,Z-1,$R^3$-2,0), (X-11,Y-3,$R^1$-2,$R^2$-1,Z-1,$R^3$-2,1), (X-11,Y-3,$R^1$-2,$R^2$-1,Z-1,$R^3$-3,0), (X-11,Y-3,$R^1$-2,$R^2$-1,Z-1,$R^3$-3,1), (X-11,Y-3,$R^1$-2,$R^2$-1,Z-1,$R^3$-1,0), (X-11,Y-3,$R^1$-2,$R^2$-1,Z-1,$R^3$-1,1), (X-11,Y-3,$R^1$-2,$R^2$-1,Z-2,$R^3$-2,0), (X-11,Y-3,$R^1$-2,$R^2$-1,Z-2,$R^3$-2,1), (X-11,Y-3,$R^1$-2,$R^2$-1,Z-2,$R^3$-3,0), (X-11,Y-3,$R^1$-2,$R^2$-1,Z-2,$R^3$-3,1), (X-11,Y-3,$R^1$-2,$R^2$-1,Z-2,$R^3$-1,0), (X-11,Y-3,$R^1$-2,$R^2$-1,Z-2,$R^3$-1,1), (X-11,Y-3,$R^1$-2,$R^2$-1,Z-2,$R^3$-2,0), (X-11,Y-3,$R^1$-2,$R^2$-1,Z-2,$R^3$-2,1), (X-11,Y-3,$R^1$-2,$R^2$-1,Z-3,$R^3$-3,0), (X-11,Y-3,$R^1$-2,$R^2$-1,Z-3,$R^3$-3,1), (X-11,Y-3,$R^1$-2,$R^2$-1,Z-3,$R^3$-1,0), (X-11,Y-3,$R^1$-2,$R^2$-1,Z-3,$R^3$-1,1), (X-11,Y-3,$R^1$-2,$R^2$-1,Z-3,$R^3$-2,0), (X-11,Y-3,$R^1$-2,$R^2$-1,Z-3,$R^3$-2,1), (X-11,Y-3,$R^1$-2,$R^2$-1,Z-3,$R^3$-3,0), (X-11,Y-3,$R^1$-2,$R^2$-1,Z-3,$R^3$-3,1), (X-11,Y-5,$R^1$-1,$R^2$-1,Z-1,$R^3$-1,0), (X-11,Y-5,$R^1$-1,$R^2$-1,Z-1,$R^3$-1,1), (X-11,Y-5,$R^1$-1,$R^2$-1,Z-1,$R^3$-2,0), (X-11,Y-5,$R^1$-1,$R^2$-1,Z-1,$R^3$-2,1), (X-11,Y-5,$R^1$-1,$R^2$-1,Z-1,$R^3$-3,0), (X-11,Y-5,$R^1$-1,$R^2$-1,Z-1,$R^3$-3,1), (X-11,Y-5,$R^1$-1,$R^2$-1,Z-1,$R^3$-1,0), (X-11,Y-5,$R^1$-1,$R^2$-1,Z-1,$R^3$-1,1), (X-11,Y-5,$R^1$-1,$R^2$-1,Z-2,$R^3$-2,0), (X-11,Y-5,$R^1$-1,$R^2$-1,Z-2,$R^3$-2,1), (X-11,Y-5,$R^1$-1,$R^2$-1,Z-2,$R^3$-3,0), (X-11,Y-5,$R^1$-1,$R^2$-1,Z-2,$R^3$-3,

1), (X-11,Y-5,R$^1$-1,R$^2$-1,Z-2,R$^3$-1,0), (X-11,Y-5,R$^1$-1,R$^2$-1, Z-2,R$^3$-1,1), (X-11,Y-5,R$^1$-1,R$^2$-1,Z-2,R$^3$-2,0), (X-11,Y-5, R$^1$-1,R$^2$-1,Z-2,R$^3$-2,1), (X-11,Y-5,R$^1$-1,R$^2$-1,Z-3,R$^3$-3,0), (X-11,Y-5,R$^1$-1,R$^2$-1,Z-3,R$^3$-3,1), (X-11,Y-5,R$^1$-1,R$^2$-1,Z-3, R$^3$-1,0), (X-11,Y-5,R$^1$-1,R$^2$-1,Z-3,R$^3$-1,1), (X-11,Y-5,R$^1$-1, R$^2$-1,Z-3,R$^3$-2,0), (X-11,Y-5,R$^1$-1,R$^2$-1,Z-3,R$^3$-2,1), (X-11, Y-5,R$^1$-1,R$^2$-1,Z-3,R$^3$-3,0), (X-11,Y-5,R$^1$-1,R$^2$-1,Z-3,R$^3$-3, 1), (X-11,Y-5,R$^1$-2,R$^2$-1,Z-1,R$^3$-1,0), (X-11,Y-5,R$^1$-2,R$^2$-1, Z-1,R$^3$-1,1), (X-11,Y-5,R$^1$-2,R$^2$-1,Z-1,R$^3$-2,0), (X-11,Y-5, R$^1$-2,R$^2$-1,Z-1,R$^3$-2,1), (X-11,Y-5,R$^1$-2,R$^2$-1,Z-1,R$^3$-3,0), (X-11,Y-5,R$^1$-2,R$^2$-1,Z-1,R$^3$-3,1), (X-11,Y-5,R$^1$-2,R$^2$-1,Z-1, R$^3$-1,0), (X-11,Y-5,R$^1$-2,R$^2$-1,Z-1,R$^3$-1,1), (X-11,Y-5,R$^1$-2, R$^2$-1,Z-2,R$^3$-2,0), (X-11,Y-5,R$^1$-2,R$^2$-1,Z-2,R$^3$-2,1), (X-11, Y-5,R$^1$-2,R$^2$-1,Z-2,R$^3$-3,0), (X-11,Y-5,R$^1$-2,R$^2$-1,Z-2,R$^3$-3, 1), (X-11,Y-5,R$^1$-2,R$^2$-1,Z-2,R$^3$-1,0), (X-11,Y-5,R$^1$-2,R$^2$-1, Z-2,R$^3$-1,1), (X-11,Y-5,R$^1$-2,R$^2$-1,Z-2,R$^3$-2,0), (X-11,Y-5, R$^1$-2,R$^2$-1,Z-2,R$^3$-2,1), (X-11,Y-5,R$^1$-2,R$^2$-1,Z-3,R$^3$-3,0), (X-11,Y-5,R$^1$-2,R$^2$-1,Z-3,R$^3$-3,1), (X-11,Y-5,R$^1$-2,R$^2$-1,Z-3, R$^3$-1,0), (X-11,Y-5,R$^1$-2,R$^2$-1,Z-3,R$^3$-1,1), (X-11,Y-5,R$^1$-2, R$^2$-1,Z-3,R$^3$-2,0), (X-11,Y-5,R$^1$-2,R$^2$-1,Z-3,R$^3$-2,1), (X-11, Y-5,R$^1$-2,R$^2$-1,Z-3,R$^3$-3,0), (X-11,Y-5,R$^1$-2,R$^2$-1,Z-3,R$^3$-3, 1), (X-11,Y-6,R$^1$-1,R$^2$-1,Z-1,R$^3$-1,0), (X-11,Y-6,R$^1$-1,R$^2$-1, Z-1,R$^3$-1,1), (X-11,Y-6,R$^1$-1,R$^2$-1,Z-1,R$^3$-2,0), (X-11,Y-6, R$^1$-1,R$^2$-1,Z-1,R$^3$-2,1), (X-11,Y-6,R$^1$-1,R$^2$-1,Z-1,R$^3$-3,0), (X-11,Y-6,R$^1$-1,R$^2$-1,Z-1,R$^3$-3,1), (X-11,Y-6,R$^1$-1,R$^2$-1,Z-1, R$^3$-1,0), (X-11,Y-6,R$^1$-1,R$^2$-1,Z-1,R$^3$-1,1), (X-11,Y-6,R$^1$-1, R$^2$-1,Z-2,R$^3$-2,0), (X-11,Y-6,R$^1$-1,R$^2$-1,Z-2,R$^3$-2,1), (X-11, Y-6,R$^1$-1,R$^2$-1,Z-2,R$^3$-3,0), (X-11,Y-6,R$^1$-1,R$^2$-1,Z-2,R$^3$-3, 1), (X-11,Y-6,R$^1$-1,R$^2$-1,Z-2,R$^3$-1,0), (X-11,Y-6,R$^1$-1,R$^2$-1, Z-2,R$^3$-1,1), (X-11,Y-6,R$^1$-1,R$^2$-1,Z-2,R$^3$-2,0), (X-11,Y-6, R$^1$-1,R$^2$-1,Z-2,R$^3$-2,1), (X-11,Y-6,R$^1$-1,R$^2$-1,Z-3,R$^3$-3,0), (X-11,Y-6,R$^1$-1,R$^2$-1,Z-3,R$^3$-3,1), (X-11,Y-6,R$^1$-1,R$^2$-1,Z-3, R$^3$-1,0), (X-11,Y-6,R$^1$-1,R$^2$-1,Z-3,R$^3$-1,1), (X-11,Y-6,R$^1$-1, R$^2$-1,Z-3,R$^3$-2,0), (X-11,Y-6,R$^1$-1,R$^2$-1,Z-3,R$^3$-2,1), (X-11, Y-6,R$^1$-1,R$^2$-1,Z-3,R$^3$-3,0), (X-11,Y-6,R$^1$-1,R$^2$-1,Z-3,R$^3$-3, 1), (X-11,Y-6,R$^1$-2,R$^2$-1,Z-1,R$^3$-1,0), (X-11,Y-6,R$^1$-2,R$^2$-1, Z-1,R$^3$-1,1), (X-11,Y-6,R$^1$-2,R$^2$-1,Z-1,R$^3$-2,0), (X-11,Y-6, R$^1$-2,R$^2$-1,Z-1,R$^3$-2,1), (X-11,Y-6,R$^1$-2,R$^2$-1,Z-1,R$^3$-3,0), (X-11,Y-6,R$^1$-2,R$^2$-1,Z-1,R$^3$-3,1), (X-11,Y-6,R$^1$-2,R$^2$-1,Z-1, R$^3$-1,0), (X-11,Y-6,R$^1$-2,R$^2$-1,Z-1,R$^3$-1,1), (X-11,Y-6,R$^1$-2, R$^2$-1,Z-2,R$^3$-2,0), (X-11,Y-6,R$^1$-2,R$^2$-1,Z-2,R$^3$-2,1), (X-11, Y-6,R$^1$-2,R$^2$-1,Z-2,R$^3$-3,0), (X-11,Y-6,R$^1$-2,R$^2$-1,Z-2,R$^3$-3, 1), (X-11,Y-6,R$^1$-2,R$^2$-1,Z-2,R$^3$-1,0), (X-11,Y-6,R$^1$-2,R$^2$-1, Z-2,R$^3$-1,1), (X-11,Y-6,R$^1$-2,R$^2$-1,Z-2,R$^3$-2,0), (X-11,Y-6, R$^1$-2,R$^2$-1,Z-2,R$^3$-2,1), (X-11,Y-6,R$^1$-2,R$^2$-1,Z-3,R$^3$-3,0), (X-11,Y-6,R$^1$-2,R$^2$-1,Z-3,R$^3$-3,1), (X-11,Y-6,R$^1$-2,R$^2$-1,Z-3, R$^3$-1,0), (X-11,Y-6,R$^1$-2,R$^2$-1,Z-3,R$^3$-1,1), (X-11,Y-6,R$^1$-2, R$^2$-1,Z-3,R$^3$-2,0), (X-11,Y-6,R$^1$-2,R$^2$-1,Z-3,R$^3$-2,1), (X-11, Y-6,R$^1$-2,R$^2$-1,Z-3,R$^3$-3,0), (X-11,Y-6,R$^1$-2,R$^2$-1,Z-3,R$^3$-3, 1), (X-11,Y-7,R$^1$-1,R$^2$-1,Z-1,R$^3$-1,0), (X-11,Y-7,R$^1$-1,R$^2$-1, Z-1,R$^3$-1,1), (X-11,Y-7,R$^1$-1,R$^2$-1,Z-1,R$^3$-2,0), (X-11,Y-7, R$^1$-1,R$^2$-1,Z-1,R$^3$-2,1), (X-11,Y-7,R$^1$-1,R$^2$-1,Z-1,R$^3$-1,0), (X-11,Y-7,R$^1$-1,R$^2$-1,Z-1,R$^3$-1,1), (X-11,Y-7,R$^1$-1,R$^2$-1,Z-2, R$^3$-2,0), (X-11,Y-7,R$^1$-1,R$^2$-1,Z-2,R$^3$-2,1), (X-11,Y-7,R$^1$-1, R$^2$-1,Z-2,R$^3$-3,0), (X-11,Y-7,R$^1$-1,R$^2$-1,Z-2,R$^3$-3,1), (X-11, Y-7,R$^1$-1,R$^2$-1,Z-2,R$^3$-1,0), (X-11,Y-7,R$^1$-1,R$^2$-1,Z-2,R$^3$-1, 1), (X-11,Y-7,R$^1$-1,R$^2$-1,Z-2,R$^3$-2,0), (X-11,Y-7,R$^1$-1,R$^2$-1, Z-2,R$^3$-2,1), (X-11,Y-7,R$^1$-1,R$^2$-1,Z-3,R$^3$-3,0), (X-11,Y-7, R$^1$-1,R$^2$-1,Z-3,R$^3$-3,1), (X-11,Y-7,R$^1$-1,R$^2$-1,Z-3,R$^3$-1,0), (X-11,Y-7,R$^1$-1,R$^2$-1,Z-3,R$^3$-1,1), (X-11,Y-7,R$^1$-1,R$^2$-1,Z-3, R$^3$-2,0), (X-11,Y-7,R$^1$-1,R$^2$-1,Z-3,R$^3$-2,1), (X-11,Y-7,R$^1$-2, R$^2$-1,Z-1,R$^3$-1,0), (X-11,Y-7,R$^1$-2,R$^2$-1,Z-1,R$^3$-1,1), (X-11, Y-7,R$^1$-2,R$^2$-1,Z-1,R$^3$-2,0), (X-11,Y-7,R$^1$-2,R$^2$-1,Z-1,R$^3$-2, 1), (X-11,Y-7,R$^1$-2,R$^2$-1,Z-1,R$^3$-3,0), (X-11,Y-7,R$^1$-2,R$^2$-1, Z-1,R$^3$-3,1), (X-11,Y-7,R$^1$-2,R$^2$-1,Z-1,R$^3$-1,0), (X-11,Y-7,R$^1$-2,R$^2$-1,Z-1,R$^3$-1,1), (X-11,Y-7,R$^1$-2,R$^2$-1,Z-2, R$^3$-2,0), (X-11,Y-7,R$^1$-2,R$^2$-1,Z-2,R$^3$-2,1), (X-11,Y-7,R$^1$-2, R$^2$-1,Z-2,R$^3$-3,0), (X-11,Y-7,R$^1$-2,R$^2$-1,Z-2,R$^3$-3,1), (X-11, Y-7,R$^1$-2,R$^2$-1,Z-2,R$^3$-1,0), (X-11,Y-7,R$^1$-2,R$^2$-1,Z-2,R$^3$-1, 1), (X-11,Y-7,R$^1$-2,R$^2$-1,Z-2,R$^3$-2,0), (X-11,Y-7,R$^1$-2,R$^2$-1, Z-2,R$^3$-2,1), (X-11,Y-7,R$^1$-2,R$^2$-1,Z-3,R$^3$-3,0), (X-11,Y-7, R$^1$-2,R$^2$-1,Z-3,R$^3$-3,1), (X-11,Y-7,R$^1$-2,R$^2$-1,Z-3,R$^3$-1,0), (X-11,Y-7,R$^1$-2,R$^2$-1,Z-3,R$^3$-1,1), (X-11,Y-7,R$^1$-2,R$^2$-1,Z-3, R$^3$-2,0), (X-11,Y-7,R$^1$-2,R$^2$-1,Z-3,R$^3$-2,1), (X-11,Y-7,R$^1$-2, R$^2$-1,Z-3,R$^3$-3,0), (X-11,Y-7,R$^1$-2,R$^2$-1,Z-3,R$^3$-3,1)

(X-16,Y-3,R$^1$-1,R$^2$-1,Z-1,R$^3$-1,0), (X-16,Y-3,R$^1$-1,R$^2$-1, Z-1,R$^3$-1,1), (X-16,Y-3,R$^1$-1,R$^2$-1,Z-1,R$^3$-2,0), (X-16,Y-3, R$^1$-1,R$^2$-1,Z-1,R$^3$-2,1), (X-16,Y-3,R$^1$-1,R$^2$-1,Z-1,R$^3$-3,0), (X-16,Y-3,R$^1$-1,R$^2$-1,Z-1,R$^3$-3,1), (X-16,Y-3,R$^1$-1,R$^2$-1,Z-1, R$^3$-1,0), (X-16,Y-3,R$^1$-1,R$^2$-1,Z-1,R$^3$-1,1), (X-16,Y-3,R$^1$-1, R$^2$-1,Z-2,R$^3$-2,0), (X-16,Y-3,R$^1$-1,R$^2$-1,Z-2,R$^3$-2,1), (X-16, Y-3,R$^1$-1,R$^2$-1,Z-2,R$^3$-3,0), (X-16,Y-3,R$^1$-1,R$^2$-1,Z-2,R$^3$-3, 1), (X-16,Y-3,R$^1$-1,R$^2$-1,Z-2,R$^3$-1,0), (X-16,Y-3,R$^1$-1,R$^2$-1, Z-2,R$^3$-1,1), (X-16,Y-3,R$^1$-1,R$^2$-1,Z-2,R$^3$-2,0), (X-16,Y-3, R$^1$-1,R$^2$-1,Z-2,R$^3$-2,1), (X-16,Y-3,R$^1$-1,R$^2$-1,Z-3,R$^3$-3,0), (X-16,Y-3,R$^1$-1,R$^2$-1,Z-3,R$^3$-3,1), (X-16,Y-3,R$^1$-1,R$^2$-1,Z-3, R$^3$-1,0), (X-16,Y-3,R$^1$-1,R$^2$-1,Z-3,R$^3$-1,1), (X-16,Y-3,R$^1$-1, R$^2$-1,Z-3,R$^3$-2,0), (X-16,Y-3,R$^1$-1,R$^2$-1,Z-3,R$^3$-2,1), (X-16, Y-3,R$^1$-1,R$^2$-1,Z-3,R$^3$-3,0), (X-16,Y-3,R$^1$-1,R$^2$-1,Z-3,R$^3$-3, 1), (X-16,Y-3,R$^1$-2,R$^2$-1,Z-1,R$^3$-1,0), (X-16,Y-3,R$^1$-2,R$^2$-1, Z-1,R$^3$-1,1), (X-16,Y-3,R$^1$-2,R$^2$-1,Z-1,R$^3$-2,0), (X-16,Y-3, R$^1$-2,R$^2$-1,Z-1,R$^3$-2,1), (X-16,Y-3,R$^1$-2,R$^2$-1,Z-1,R$^3$-3,0), (X-16,Y-3,R$^1$-2,R$^2$-1,Z-1,R$^3$-3,1), (X-16,Y-3,R$^1$-2,R$^2$-1,Z-1, R$^3$-1,0), (X-16,Y-3,R$^1$-2,R$^2$-1,Z-1,R$^3$-1,1), (X-16,Y-3,R$^1$-2, R$^2$-1,Z-2,R$^3$-2,0), (X-16,Y-3,R$^1$-2,R$^2$-1,Z-2,R$^3$-2,1), (X-16, Y-3,R$^1$-2,R$^2$-1,Z-2,R$^3$-2,3,0), (X-16,Y-3,R$^1$-2,R$^2$-1,Z-2,R$^3$-3, 1), (X-16,Y-3,R$^1$-2,R$^2$-1,Z-2,R$^3$-1,0), (X-16,Y-3,R$^1$-2,R$^2$-1, Z-2,R$^3$-1,1), (X-16,Y-3,R$^1$-2,R$^2$-1,Z-2,R$^3$-2,0), (X-16,Y-3, R$^1$-2,R$^2$-1,Z-2,R$^3$-2,1), (X-16,Y-3,R$^1$-2,R$^2$-1,Z-3,R$^3$-3,0), (X-16,Y-3,R$^1$-2,R$^2$-1,Z-3,R$^3$-3,1), (X-16,Y-3,R$^1$-2,R$^2$-1,Z-3, R$^3$-1,0), (X-16,Y-3,R$^1$-2,R$^2$-1,Z-3,R$^3$-1,1), (X-16,Y-3,R$^1$-2, R$^2$-1,Z-3,R$^3$-2,0), (X-16,Y-3,R$^1$-2,R$^2$-1,Z-3,R$^3$-2,1), (X-16, Y-3,R$^1$-2,R$^2$-1,Z-3,R$^3$-3,0), (X-16,Y-3,R$^1$-2,R$^2$-1,Z-3,R$^3$-3, 1), (X-16,Y-5,R$^1$-1,R$^2$-1,Z-1,R$^3$-1,0), (X-16,Y-5,R$^1$-1,R$^2$-1, Z-1,R$^3$-1,1), (X-16,Y-5,R$^1$-1,R$^2$-1,Z-1,R$^3$-2,0), (X-16,Y-5, R$^1$-1,R$^2$-1,Z-1,R$^3$-2,1), (X-16,Y-5,R$^1$-1,R$^2$-1,Z-1,R$^3$-3,0), (X-16,Y-5,R$^1$-1,R$^2$-1,Z-1,R$^3$-3,1), (X-16,Y-5,R$^1$-1,R$^2$-1,Z-1, R$^3$-1,0), (X-16,Y-5,R$^1$-1,R$^2$-1,Z-1,R$^3$-1,1), (X-16,Y-5,R$^1$-1, R$^2$-1,Z-2,R$^3$-2,0), (X-16,Y-5,R$^1$-1,R$^2$-1,Z-2,R$^3$-2,1), (X-16, Y-5,R$^1$-1,R$^2$-1,Z-2,R$^3$-3,0), (X-16,Y-5,R$^1$-1,R$^2$-1,Z-2,R$^3$-3, 1), (X-16,Y-5,R$^1$-1,R$^2$-1,Z-2,R$^3$-1,0), (X-16,Y-5,R$^1$-1,R$^2$-1, Z-2,R$^3$-1,1), (X-16,Y-5,R$^1$-1,R$^2$-1,Z-2,R$^3$-2,0), (X-16,Y-5, R$^1$-1,R$^2$-1,Z-2,R$^3$-2,1), (X-16,Y-5,R$^1$-1,R$^2$-1,Z-3,R$^3$-3,0), (X-16,Y-5,R$^1$-1,R$^2$-1,Z-3,R$^3$-3,1), (X-16,Y-5,R$^1$-1,R$^2$-1,Z-3, R$^3$-1,0), (X-16,Y-5,R$^1$-1,R$^2$-1,Z-3,R$^3$-1,1), (X-16,Y-5,R$^1$-1, R$^2$-1,Z-3,R$^3$-2,0), (X-16,Y-5,R$^1$-1,R$^2$-1,Z-3,R$^3$-2,1), (X-16, Y-5,R$^1$-1,R$^2$-1,Z-3,R$^3$-3,0), (X-16,Y-5,R$^1$-1,R$^2$-1,Z-3,R$^3$-3, 1), (X-16,Y-5,R$^1$-2,R$^2$-1,Z-1,R$^3$-1,0), (X-16,Y-5,R$^1$-2,R$^2$-1, Z-1,R$^3$-1,1), (X-16,Y-5,R$^1$-2,R$^2$-1,Z-1,R$^3$-2,0), (X-16,Y-5, R$^1$-2,R$^2$-1,Z-1,R$^3$-2,1), (X-16,Y-5,R$^1$-2,R$^2$-1,Z-1,R$^3$-3,0), (X-16,Y-5,R$^1$-2,R$^2$-1,Z-1,R$^3$-3,1), (X-16,Y-5,R$^1$-2,R$^2$-1,Z-1, R$^3$-1,0), (X-16,Y-5,R$^1$-2,R$^2$-1,Z-1,R$^3$-1,1), (X-16,Y-5,R$^1$-2, R$^2$-1,Z-2,R$^3$-2,0), (X-16,Y-5,R$^1$-2,R$^2$-1,Z-2,R$^3$-2,1), (X-16, Y-5,R$^1$-2,R$^2$-1,Z-2,R$^3$-3,0), (X-16,Y-5,R$^1$-2,R$^2$-1,Z-2,R$^3$-3, 1), (X-16,Y-5,R$^1$-2,R$^2$-1,Z-2,R$^3$-1,0), (X-16,Y-5,R$^1$-2,R$^2$-1, Z-2,R$^3$-1,1), (X-16,Y-5,R$^1$-2,R$^2$-1,Z-2,R$^3$-2,0), (X-16,Y-5, R$^1$-2,R$^2$-1,Z-2,R$^3$-2,1), (X-16,Y-5,R$^1$-2,R$^2$-1,Z-3,R$^3$-3,0), (X-16,Y-5,R$^1$-2,R$^2$-1,Z-3,R$^3$-3,1), (X-16,Y-5,R$^1$-2,R$^2$-1,Z-3, R$^3$-1,0), (X-16,Y-5,R$^1$-2,R$^2$-1,Z-3,R$^3$-1,1), (X-16,Y-5,R$^1$-2, R$^2$-1,Z-3,R$^3$-2,0), (X-16,Y-5,R$^1$-2,R$^2$-1,Z-3,R$^3$-2,1), (X-16, Y-5,R$^1$-2,R$^2$-1,Z-3,R$^3$-3,0), (X-16,Y-5,R$^1$-2,R$^2$-1,Z-3,R$^3$-3, 1), (X-16,Y-6,R$^1$-1,R$^2$-1,Z-1,R$^3$-1,0), (X-16,Y-6,R$^1$-1,R$^2$-1, Z-1,R$^3$-1,1), (X-16,Y-6,R$^1$-1,R$^2$-1,Z-1,R$^3$-2,0), (X-16,Y-6, $R^1$-1,$R^2$-1,Z-1,$R^3$-2,1), (X-16,Y-6,$R^1$-1,$R^2$-1,Z-1,$R^3$-3,0), (X-16,Y-6,$R^1$-1,$R^2$-1,Z-1,$R^3$-3,1), (X-16,Y-6,$R^1$-1,$R^2$-1,Z-1,$R^3$-1,0), (X-16,Y-6,$R^1$-1,$R^2$-1,Z-1,$R^3$-1,1), (X-16,Y-6,$R^1$-1,$R^2$-1,Z-2,$R^3$-2,0), (X-16,Y-6,$R^1$-1,$R^2$-1,Z-2,$R^3$-2,1), (X-16,Y-6,$R^1$-1,$R^2$-1,Z-2,$R^3$-3,0), (X-16,Y-6,$R^1$-1,$R^2$-1,Z-2,$R^3$-3,1), (X-16,Y-6,$R^1$-1,$R^2$-1,Z-2,$R^3$-1,0), (X-16,Y-6,$R^1$-1,$R^2$-1,Z-2,$R^3$-1,1), (X-16,Y-6,$R^1$-1,$R^2$-1,Z-2,$R^3$-2,0), (X-16,Y-6,$R^1$-1,$R^2$-1,Z-2,$R^3$-2,1), (X-16,Y-6,$R^1$-1,$R^2$-1,Z-3,$R^3$-3,0), (X-16,Y-6,$R^1$-1,$R^2$-1,Z-3,$R^3$-3,1), (X-16,Y-6,$R^1$-1,$R^2$-1,Z-3,$R^3$-1,0), (X-16,Y-6,$R^1$-1,$R^2$-1,Z-3,$R^3$-1,1), (X-16,Y-6,$R^1$-1,$R^2$-1,Z-3,$R^3$-2,0), (X-16,Y-6,$R^1$-1,$R^2$-1,Z-3,$R^3$-2,1), (X-16,Y-6,$R^1$-1,$R^2$-1,Z-3,$R^3$-3,0), (X-16,Y-6,$R^1$-1,$R^2$-1,Z-3,$R^3$-3,1), (X-16,Y-6,$R^1$-2,$R^2$-1,Z-1,$R^3$-1,0), (X-16,Y-6,$R^1$-2,$R^2$-1,Z-1,$R^3$-1,1), (X-16,Y-6,$R^1$-2,$R^2$-1,Z-1,$R^3$-2,0), (X-16,Y-6,$R^1$-2,$R^2$-1,Z-1,$R^3$-2,1), (X-16,Y-6,$R^1$-2,$R^2$-1,Z-1,$R^3$-3,0), (X-16,Y-6,$R^1$-2,$R^2$-1,Z-1,$R^3$-3,1), (X-16,Y-6,$R^1$-2,$R^2$-1,Z-1,$R^3$-1,0), (X-16,Y-6,$R^1$-2,$R^2$-1,Z-1,$R^3$-1,1), (X-16,Y-6,$R^1$-2,$R^2$-1,Z-2,$R^3$-2,0), (X-16,Y-6,$R^1$-2,$R^2$-1,Z-2,$R^3$-2,1), (X-16,Y-6,$R^1$-2,$R^2$-1,Z-2,$R^3$-3,0), (X-16,Y-6,$R^1$-2,$R^2$-1,Z-2,$R^3$-3,1), (X-16,Y-6,$R^1$-2,$R^2$-1,Z-2,$R^3$-1,0), (X-16,Y-6,$R^1$-2,$R^2$-1,Z-2,$R^3$-1,1), (X-16,Y-6,$R^1$-2,$R^2$-1,Z-2,$R^3$-2,0), (X-16,Y-6,$R^1$-2,$R^2$-1,Z-2,$R^3$-2,1), (X-16,Y-6,$R^1$-2,$R^2$-1,Z-3,$R^3$-3,0), (X-16,Y-6,$R^1$-2,$R^2$-1,Z-3,$R^3$-3,1), (X-16,Y-6,$R^1$-2,$R^2$-1,Z-3,$R^3$-1,0), (X-16,Y-6,$R^1$-2,$R^2$-1,Z-3,$R^3$-1,1), (X-16,Y-6,$R^1$-2,$R^2$-1,Z-3,$R^3$-2,0), (X-16,Y-6,$R^1$-2,$R^2$-1,Z-3,$R^3$-2,1), (X-16,Y-6,$R^1$-2,$R^2$-1,Z-3,$R^3$-3,0), (X-16,Y-6,$R^1$-2,$R^2$-1,Z-3,$R^3$-3,1), (X-16,Y-7,$R^1$-1,$R^2$-1,Z-1,$R^3$-1,0), (X-16,Y-7,$R^1$-1,$R^2$-1,Z-1,$R^3$-1,1), (X-16,Y-7,$R^1$-1,$R^2$-1,Z-1,$R^3$-2,0), (X-16,Y-7,$R^1$-1,$R^2$-1,Z-1,$R^3$-2,1), (X-16,Y-7,$R^1$-1,$R^2$-1,Z-1,$R^3$-1,0), (X-16,Y-7,$R^1$-1,$R^2$-1,Z-1,$R^3$-1,1), (X-16,Y-7,$R^1$-1,$R^2$-1,Z-2,$R^3$-2,0), (X-16,Y-7,$R^1$-1,$R^2$-1,Z-2,$R^3$-2,1), (X-16,Y-7,$R^1$-1,$R^2$-1,Z-2,$R^3$-3,0), (X-16,Y-7,$R^1$-1,$R^2$-1,Z-2,$R^3$-3,1), (X-16,Y-7,$R^1$-1,$R^2$-1,Z-2,$R^3$-1,0), (X-16,Y-7,$R^1$-1,$R^2$-1,Z-2,$R^3$-1,1), (X-16,Y-7,$R^1$-1,$R^2$-1,Z-2,$R^3$-2,0), (X-16,Y-7,$R^1$-1,$R^2$-1,Z-2,$R^3$-2,1), (X-16,Y-7,$R^1$-1,$R^2$-1,Z-3,$R^3$-3,0), (X-16,Y-7,$R^1$-1,$R^2$-1,Z-3,$R^3$-3,1), (X-16,Y-7,$R^1$-1,$R^2$-1,Z-3,$R^3$-1,0), (X-16,Y-7,$R^1$-1,$R^2$-1,Z-3,$R^3$-1,1), (X-16,Y-7,$R^1$-1,$R^2$-1,Z-3,$R^3$-2,0), (X-16,Y-7,$R^1$-1,$R^2$-1,Z-3,$R^3$-2,1), (X-16,Y-7,$R^1$-1,$R^2$-1,Z-3,$R^3$-3,0), (X-16,Y-7,$R^1$-1,$R^2$-1,Z-3,$R^3$-3,1), (X-16,Y-7,$R^1$-2,$R^2$-1,Z-1,$R^3$-1,0), (X-16,Y-7,$R^1$-2,$R^2$-1,Z-1,$R^3$-1,1), (X-16,Y-7,$R^1$-2,$R^2$-1,Z-1,$R^3$-2,0), (X-16,Y-7,$R^1$-2,$R^2$-1,Z-1,$R^3$-2,1), (X-16,Y-7,$R^1$-2,$R^2$-1,Z-1,$R^3$-3,0), (X-16,Y-7,$R^1$-2,$R^2$-1,Z-1,$R^3$-3,1), (X-16,Y-7,$R^1$-2,$R^2$-1,Z-1,$R^3$-1,0), (X-16,Y-7,$R^1$-2,$R^2$-1,Z-1,$R^3$-1,1), (X-16,Y-7,$R^1$-2,$R^2$-1,Z-2,$R^3$-2,0), (X-16,Y-7,$R^1$-2,$R^2$-1,Z-2,$R^3$-2,1), (X-16,Y-7,$R^1$-2,$R^2$-1,Z-2,$R^3$-3,0), (X-16,Y-7,$R^1$-2,$R^2$-1,Z-2,$R^3$-3,1), (X-16,Y-7,$R^1$-2,$R^2$-1,Z-2,$R^3$-1,0), (X-16,Y-7,$R^1$-2,$R^2$-1,Z-2,$R^3$-1,1), (X-16,Y-7,$R^1$-2,$R^2$-1,Z-2,$R^3$-2,0), (X-16,Y-7,$R^1$-2,$R^2$-1,Z-2,$R^3$-2,1), (X-16,Y-7,$R^1$-2,$R^2$-1,Z-3,$R^3$-3,0), (X-16,Y-7,$R^1$-2,$R^2$-1,Z-3,$R^3$-3,1), (X-16,Y-7,$R^1$-2,$R^2$-1,Z-3,$R^3$-1,0), (X-16,Y-7,$R^1$-2,$R^2$-1,Z-3,$R^3$-1,1), (X-16,Y-7,$R^1$-2,$R^2$-1,Z-3,$R^3$-2,0), (X-16,Y-7,$R^1$-2,$R^2$-1,Z-3,$R^3$-2,1), (X-16,Y-7,$R^1$-2,$R^2$-1,Z-3,$R^3$-3,0), (X-16,Y-7,$R^1$-2,$R^2$-1,Z-3,$R^3$-3,1)

(X-19,Y-3,$R^1$-1,$R^2$-1,Z-1,$R^3$-1,0), (X-19,Y-3,$R^1$-1,$R^2$-1,Z-1,$R^3$-1,1), (X-19,Y-3,$R^1$-1,$R^2$-1,Z-1,$R^3$-2,0), (X-19,Y-3,$R^1$-1,$R^2$-1,Z-1,$R^3$-2,1), (X-19,Y-3,$R^1$-1,$R^2$-1,Z-1,$R^3$-3,0), (X-19,Y-3,$R^1$-1,$R^2$-1,Z-1,$R^3$-3,1), (X-19,Y-3,$R^1$-1,$R^2$-1,Z-1,$R^3$-1,0), (X-19,Y-3,$R^1$-1,$R^2$-1,Z-1,$R^3$-1,1), (X-19,Y-3,$R^1$-1,$R^2$-1,Z-2,$R^3$-2,0), (X-19,Y-3,$R^1$-1,$R^2$-1,Z-2,$R^3$-2,1), (X-19,Y-3,$R^1$-1,$R^2$-1,Z-2,$R^3$-3,0), (X-19,Y-3,$R^1$-1,$R^2$-1,Z-2,$R^3$-3,1), (X-19,Y-3,$R^1$-1,$R^2$-1,Z-2,$R^3$-1,0), (X-19,Y-3,$R^1$-1,$R^2$-1,Z-2,$R^3$-1,1), (X-19,Y-3,$R^1$-1,$R^2$-1,Z-2,$R^3$-2,0), (X-19,Y-3,$R^1$-1,$R^2$-1,Z-2,$R^3$-2,1), (X-19,Y-3,$R^1$-1,$R^2$-1,Z-3,$R^3$-3,0), (X-19,Y-3,$R^1$-1,$R^2$-1,Z-3,$R^3$-3,1), (X-19,Y-3,$R^1$-1,$R^2$-1,Z-3,$R^3$-1,0), (X-19,Y-3,$R^1$-1,$R^2$-1,Z-3,$R^3$-1,1), (X-19,Y-3,$R^1$-1,$R^2$-1,Z-3,$R^3$-2,0), (X-19,Y-3,$R^1$-1,$R^2$-1,Z-3,$R^3$-2,1), (X-19,Y-3,$R^1$-1,$R^2$-1,Z-3,$R^3$-3,0), (X-19,Y-3,$R^1$-1,$R^2$-1,Z-3,$R^3$-3,1), (X-19,Y-3,$R^1$-2,$R^2$-1,Z-1,$R^3$-1,0), (X-19,Y-3,$R^1$-2,$R^2$-1,Z-1,$R^3$-1,1), (X-19,Y-3,$R^1$-2,$R^2$-1,Z-1,$R^3$-2,0), (X-19,Y-3,$R^1$-2,$R^2$-1,Z-1,$R^3$-2,1), (X-19,Y-3,$R^1$-2,$R^2$-1,Z-1,$R^3$-3,0), (X-19,Y-3,$R^1$-2,$R^2$-1,Z-1,$R^3$-3,1), (X-19,Y-3,$R^1$-2,$R^2$-1,Z-1,$R^3$-1,0), (X-19,Y-3,$R^1$-2,$R^2$-1,Z-1,$R^3$-1,1), (X-19,Y-3,$R^1$-2,$R^2$-1,Z-2,$R^3$-2,0), (X-19,Y-3,$R^1$-2,$R^2$-1,Z-2,$R^3$-2,1), (X-19,Y-3,$R^1$-2,$R^2$-1,Z-2,$R^3$-3,0), (X-19,Y-3,$R^1$-2,$R^2$-1,Z-2,$R^3$-3,1), (X-19,Y-3,$R^1$-2,$R^2$-1,Z-2,$R^3$-1,0), (X-19,Y-3,$R^1$-2,$R^2$-1,Z-2,$R^3$-1,1), (X-19,Y-3,$R^1$-2,$R^2$-1,Z-2,$R^3$-2,0), (X-19,Y-3,$R^1$-2,$R^2$-1,Z-2,$R^3$-2,1), (X-19,Y-3,$R^1$-2,$R^2$-1,Z-3,$R^3$-3,0), (X-19,Y-3,$R^1$-2,$R^2$-1,Z-3,$R^3$-3,1), (X-19,Y-3,$R^1$-2,$R^2$-1,Z-3,$R^3$-1,0), (X-19,Y-3,$R^1$-2,$R^2$-1,Z-3,$R^3$-1,1), (X-19,Y-3,$R^1$-2,$R^2$-1,Z-3,$R^3$-2,0), (X-19,Y-3,$R^1$-2,$R^2$-1,Z-3,$R^3$-2,1), (X-19,Y-3,$R^1$-2,$R^2$-1,Z-3,$R^3$-3,0), (X-19,Y-3,$R^1$-2,$R^2$-1,Z-3,$R^3$-3,1), (X-19,Y-5,$R^1$-1,$R^2$-1,Z-1,$R^3$-1,0), (X-19,Y-5,$R^1$-1,$R^2$-1,Z-1,$R^3$-1,1), (X-19,Y-5,$R^1$-1,$R^2$-1,Z-1,$R^3$-2,0), (X-19,Y-5,$R^1$-1,$R^2$-1,Z-1,$R^3$-2,1), (X-19,Y-5,$R^1$-1,$R^2$-1,Z-1,$R^3$-3,0), (X-19,Y-5,$R^1$-1,$R^2$-1,Z-1,$R^3$-3,1), (X-19,Y-5,$R^1$-1,$R^2$-1,Z-1,$R^3$-1,0), (X-19,Y-5,$R^1$-1,$R^2$-1,Z-1,$R^3$-1,1), (X-19,Y-5,$R^1$-1,$R^2$-1,Z-2,$R^3$-2,0), (X-19,Y-5,$R^1$-1,$R^2$-1,Z-2,$R^3$-2,1), (X-19,Y-5,$R^1$-1,$R^2$-1,Z-2,$R^3$-3,0), (X-19,Y-5,$R^1$-1,$R^2$-1,Z-2,$R^3$-3,1), (X-19,Y-5,$R^1$-1,$R^2$-1,Z-2,$R^3$-1,0), (X-19,Y-5,$R^1$-1,$R^2$-1,Z-2,$R^3$-1,1), (X-19,Y-5,$R^1$-1,$R^2$-1,Z-2,$R^3$-2,0), (X-19,Y-5,$R^1$-1,$R^2$-1,Z-2,$R^3$-2,1), (X-19,Y-5,$R^1$-1,$R^2$-1,Z-3,$R^3$-3,0), (X-19,Y-5,$R^1$-1,$R^2$-1,Z-3,$R^3$-3,1), (X-19,Y-5,$R^1$-1,$R^2$-1,Z-3,$R^3$-1,0), (X-19,Y-5,$R^1$-1,$R^2$-1,Z-3,$R^3$-1,1), (X-19,Y-5,$R^1$-1,$R^2$-1,Z-3,$R^3$-2,0), (X-19,Y-5,$R^1$-1,$R^2$-1,Z-3,$R^3$-2,1), (X-19,Y-5,$R^1$-1,$R^2$-1,Z-3,$R^3$-3,0), (X-19,Y-5,$R^1$-1,$R^2$-1,Z-3,$R^3$-3,1), (X-19,Y-5,$R^1$-2,$R^2$-1,Z-1,$R^3$-1,1), (X-19,Y-5,$R^1$-2,$R^2$-1,Z-1,$R^3$-2,0), (X-19,Y-5,$R^1$-2,$R^2$-1,Z-1,$R^3$-2,1), (X-19,Y-5,$R^1$-2,$R^2$-1,Z-1,$R^3$-3,0), (X-19,Y-5,$R^1$-2,$R^2$-1,Z-1,$R^3$-3,1), (X-19,Y-5,$R^1$-2,$R^2$-1,Z-1,$R^3$-1,0), (X-19,Y-5,$R^1$-2,$R^2$-1,Z-1,$R^3$-1,1), (X-19,Y-5,$R^1$-2,$R^2$-1,Z-2,$R^3$-2,0), (X-19,Y-5,$R^1$-2,$R^2$-1,Z-2,$R^3$-2,1), (X-19,Y-5,$R^1$-2,$R^2$-1,Z-2,$R^3$-3,0), (X-19,Y-5,$R^1$-2,$R^2$-1,Z-2,$R^3$-3,1), (X-19,Y-5,$R^1$-2,$R^2$-1,Z-2,$R^3$-1,0), (X-19,Y-5,$R^1$-2,$R^2$-1,Z-2,$R^3$-1,1), (X-19,Y-5,$R^1$-2,$R^2$-1,Z-2,$R^3$-2,0), (X-19,Y-5,$R^1$-2,$R^2$-1,Z-2,$R^3$-2,1), (X-19,Y-5,$R^1$-2,$R^2$-1,Z-3,$R^3$-3,0), (X-19,Y-5,$R^1$-2,$R^2$-1,Z-3,$R^3$-3,1), (X-19,Y-5,$R^1$-2,$R^2$-1,Z-3,$R^3$-1,0), (X-19,Y-5,$R^1$-2,$R^2$-1,Z-3,$R^3$-1,1), (X-19,Y-5,$R^1$-2,$R^2$-1,Z-3,$R^3$-2,0), (X-19,Y-5,$R^1$-2,$R^2$-1,Z-3,$R^3$-2,1), (X-19,Y-5,$R^1$-2,$R^2$-1,Z-3,$R^3$-3,0), (X-19,Y-5,$R^1$-2,$R^2$-1,Z-3,$R^3$-3,1), (X-19,Y-6,$R^1$-1,$R^2$-1,Z-1,$R^3$-1,0), (X-19,Y-6,$R^1$-1,$R^2$-1,Z-1,$R^3$-1,1), (X-19,Y-6,$R^1$-1,$R^2$-1,Z-1,$R^3$-2,0), (X-19,Y-6,$R^1$-1,$R^2$-1,Z-1,$R^3$-2,1), (X-19,Y-6,$R^1$-1,$R^2$-1,Z-1,$R^3$-3,0), (X-19,Y-6,$R^1$-1,$R^2$-1,Z-1,$R^3$-3,1), (X-19,Y-6,$R^1$-1,$R^2$-1,Z-1,$R^3$-1,0), (X-19,Y-6,$R^1$-1,$R^2$-1,Z-1,$R^3$-1,1), (X-19,Y-6,$R^1$-1,$R^2$-1,Z-2,$R^3$-2,0), (X-19,Y-6,$R^1$-1,$R^2$-1,Z-2,$R^3$-2,1), (X-19,Y-6,$R^1$-1,$R^2$-1,Z-2,$R^3$-3,0), (X-19,Y-6,$R^1$-1,$R^2$-1,Z-2,$R^3$-3,1), (X-19,Y-6,$R^1$-1,$R^2$-1,Z-2,$R^3$-1,0), (X-19,Y-6,$R^1$-1,$R^2$-1,Z-2,$R^3$-1,1), (X-19,Y-6,$R^1$-1,$R^2$-1,Z-2,$R^3$-2,0), (X-19,Y-6,$R^1$-1,$R^2$-1,Z-2,$R^3$-2,1), (X-19,Y-6,$R^1$-1,$R^2$-1,Z-3,$R^3$-3,0), (X-19,Y-6,$R^1$-1,$R^2$-1,Z-3,$R^3$-3,1), (X-19,Y-6,$R^1$-1,$R^2$-1,Z-3,$R^3$-1,0), (X-19,Y-6,$R^1$-1,$R^2$-1,Z-3,$R^3$-1,1), (X-19,Y-6,$R^1$-1,$R^2$-1,Z-3,$R^3$-2,0), (X-19,Y-6,$R^1$-1,$R^2$-1,Z-3,$R^3$-2,1), (X-19,Y-6,$R^1$-1,$R^2$-1,Z-3,$R^3$-3,0), (X-19,Y-6,$R^1$-1,$R^2$-1,Z-3,$R^3$-3,1), (X-19,Y-6,$R^1$-2,$R^2$-1,Z-1,$R^3$-1,0), (X-19,Y-6,$R^1$-2,$R^2$-1,Z-1,$R^3$-1,1), (X-19,Y-6,$R^1$-2,$R^2$-1,Z-1,$R^3$-2,0), (X-19,Y-6,$R^1$-2,$R^2$-1,Z-1,$R^3$-2,1), (X-19,Y-6,$R^1$-2,$R^2$-1,Z-1,$R^3$-3,0), (X-19,Y-6,$R^1$-2,$R^2$-1,Z-1,$R^3$-3,1), (X-19,Y-6,$R^1$-2,$R^2$-1,Z-1,$R^3$-1,0), (X-19,Y-6,$R^1$-2,$R^2$-1,Z-1,$R^3$-1,1), (X-19,Y-6,$R^1$-2,$R^2$-1,Z-2,$R^3$-2,0), (X-19,Y-6,$R^1$-2,$R^2$-1,Z-2,$R^3$-2,1), (X-19,Y-6,$R^1$-2,$R^2$-1,Z-2,$R^3$-3,0), (X-19,Y-6,$R^1$-2,$R^2$-1,Z-2,$R^3$-3,1), (X-19,Y-6,$R^1$-2,$R^2$-1,Z-2,$R^3$-1,0), (X-19,Y-6,$R^1$-2,$R^2$-1,Z-2,$R^3$-1,1), (X-19,Y-6,$R^1$-2,$R^2$-1,Z-2,$R^3$-2,0), (X-19,Y-6,$R^1$-2,$R^2$-1,Z-2,$R^3$-2,1), (X-19,Y-6,$R^1$-2,$R^2$-1,Z-3,$R^3$-3,0), (X-19,Y-6,$R^1$-2,$R^2$-1,Z-3,$R^3$-3,1), (X-19,Y-6,$R^1$-2,$R^2$-1,Z-3,$R^3$-1,0), (X-19,Y-6,$R^1$-2,$R^2$-1,Z-3,

R³-1,1), (X-19,Y-6,R¹-2,R²-1,Z-3,R³-2,0), (X-19,Y-6,R¹-2, R²-1,Z-3,R³-2,1), (X-19,Y-6,R¹-2,R²-1,Z-3,R³-3,0), (X-19, Y-6,R¹-2,R²-1,Z-3,R³-3,1), (X-19,Y-7,R¹-1,R²-1,Z-1,R³-1, 0), (X-19,Y-7,R¹-1,R²-1,Z-1,R³-1,1), (X-19,Y-7,R¹-1,R²-1, Z-1,R³-2,0), (X-19,Y-7,R¹-1,R²-1,Z-1,R³-2,1), (X-19,Y-7, R¹-1,R²-1,Z-1,R³-1,0), (X-19,Y-7,R¹-1,R²-1,Z-1,R³-1,1), (X-19,Y-7,R¹-1,R²-1,Z-2,R³-2,0), (X-19,Y-7,R¹-1,R²-1,Z-2, R³-2,1), (X-19,Y-7,R¹-1,R²-1,Z-2,R³-3,0), (X-19,Y-7,R¹-1, R²-1,Z-2,R³-3,1), (X-19,Y-7,R¹-1,R²-1,Z-2,R³-1,0), (X-19, Y-7,R¹-1,R²-1,Z-2,R³-1,1), (X-19,Y-7,R¹-1,R²-1,Z-2,R³-2, 0), (X-19,Y-7,R¹-1,R²-1,Z-2,R³-2,1), (X-19,Y-7,R¹-1,R²-1, Z-3,R³-3,0), (X-19,Y-7,R¹-1,R²-1,Z-3,R³-3,1), (X-19,Y-7, R¹-1,R²-1,Z-3,R³-1,0), (X-19,Y-7,R¹-1,R²-1,Z-3,R³-1,1), (X-19,Y-7,R¹-1,R²-1,Z-3,R³-2,0), (X-19,Y-7,R¹-1,R²-1,Z-3, R³-2,1), (X-19,Y-7,R¹-1,R²-1,Z-3,R³-3,0), (X-19,Y-7,R¹-1, R²-1,Z-3,R³-3,1), (X-19,Y-7,R¹-2,R²-1,Z-1,R³-1,0), (X-19, Y-7,R¹-2,R²-1,Z-1,R³-1,1), (X-19,Y-7,R¹-2,R²-1,Z-1,R³-2, 0), (X-19,Y-7,R¹-2,R²-1,Z-1,R³-2,1), (X-19,Y-7,R¹-2,R²-1, Z-1,R³-3,0), (X-19,Y-7,R¹-2,R²-1,Z-1,R³-3,1), (X-19,Y-7, R¹-2,R²-1,Z-1,R³-1,0), (X-19,Y-7,R¹-2,R²-1,Z-1,R³-1,1), (X-19,Y-7,R¹-2,R²-1,Z-2,R³-2,0), (X-19,Y-7,R¹-2,R²-1,Z-2, R³-2,1), (X-19,Y-7,R¹-2,R²-1,Z-2,R³-3,0), (X-19,Y-7,R¹-2, R²-1,Z-2,R³-3,1), (X-19,Y-7,R¹-2,R²-1,Z-2,R³-1,0), (X-19, Y-7,R¹-2,R²-1,Z-2,R³-1,1), (X-19,Y-7,R¹-2,R²-1,Z-2,R³-2, 0), (X-19,Y-7,R¹-2,R²-1,Z-2,R³-2,1), (X-19,Y-7,R¹-2,R²-1, Z-3,R³-3,0), (X-19,Y-7,R¹-2,R²-1,Z-3,R³-3,1), (X-19,Y-7, R¹-2,R²-1,Z-3,R³-1,0), (X-19,Y-7,R¹-2,R²-1,Z-3,R³-1,1), (X-19,Y-7,R¹-2,R²-1,Z-3,R³-2,0), (X-19,Y-7,R¹-2,R²-1,Z-3, R³-2,1), (X-19,Y-7,R¹-2,R²-1,Z-3,R³-3,0), (X-19,Y-7,R¹-2, R²-1,Z-3,R³-3,1)

(X-20,Y-3,R¹-1,R²-1,Z-1,R³-1,0), (X-20,Y-3,R¹-1,R²-1, Z-1,R³-1,1), (X-20,Y-3,R¹-1,R²-1,Z-1,R³-2,0), (X-20,Y-3, R¹-1,R²-1,Z-1,R³-2,1), (X-20,Y-3,R¹-1,R²-1,Z-1,R³-3,0), (X-20,Y-3,R¹-1,R²-1,Z-1,R³-3,1), (X-20,Y-3,R¹-1,R²-1,Z-1, R³-1,0), (X-20,Y-3,R¹-1,R²-1,Z-1,R³-1,1), (X-20,Y-3,R¹-1, R²-1,Z-2,R³-2,0), (X-20,Y-3,R¹-1,R²-1,Z-2,R³-2,1), (X-20, Y-3,R¹-1,R²-1,Z-2,R³-3,0), (X-20,Y-3,R¹-1,R²-1,Z-2,R³-3, 1), (X-20,Y-3,R¹-1,R²-1,Z-2,R³-1,0), (X-20,Y-3,R¹-1,R²-1, Z-2,R³-1,1), (X-20,Y-3,R¹-1,R²-1,Z-2,R³-2,0), (X-20,Y-3, R¹-1,R²-1,Z-2,R³-2,1), (X-20,Y-3,R¹-1,R²-1,Z-3,R³-3,0), (X-20,Y-3,R¹-1,R²-1,Z-3,R³-3,1), (X-20,Y-3,R¹-1,R²-1,Z-3, R³-1,0), (X-20,Y-3,R¹-1,R²-1,Z-3,R³-1,1), (X-20,Y-3,R¹-1, R²-1,Z-3,R³-2,0), (X-20,Y-3,R¹-1,R²-1,Z-3,R³-2,1), (X-20, Y-3,R¹-1,R²-1,Z-3,R³-3,0), (X-20,Y-3,R¹-1,R²-1,Z-3,R³-3, 1), (X-20,Y-3,R¹-2,R²-1,Z-1,R³-1,0), (X-20,Y-3,R¹-2,R²-1, Z-1,R³-1,1), (X-20,Y-3,R¹-2,R²-1,Z-1,R³-2,0), (X-20,Y-3, R¹-2,R²-1,Z-1,R³-2,1), (X-20,Y-3,R¹-2,R²-1,Z-1,R³-3,0), (X-20,Y-3,R¹-2,R²-1,Z-1,R³-3,1), (X-20,Y-3,R¹-2,R²-1,Z-1, R³-1,0), (X-20,Y-3,R¹-2,R²-1,Z-1,R³-1,1), (X-20,Y-3,R¹-2, R²-1,Z-2,R³-2,0), (X-20,Y-3,R¹-2,R²-1,Z-2,R³-2,1), (X-20, Y-3,R¹-2,R²-1,Z-2,R³-3,0), (X-20,Y-3,R¹-2,R²-1,Z-2,R³-3, 1), (X-20,Y-3,R¹-2,R²-1,Z-2,R³-1,0), (X-20,Y-3,R¹-2,R²-1, Z-2,R³-1,1), (X-20,Y-3,R¹-2,R²-1,Z-2,R³-2,0), (X-20,Y-3, R¹-2,R²-1,Z-2,R³-2,1), (X-20,Y-3,R¹-2,R²-1,Z-3,R³-3,0), (X-20,Y-3,R¹-2,R²-1,Z-3,R³-3,1), (X-20,Y-3,R¹-2,R²-1,Z-3, R³-1,0), (X-20,Y-3,R¹-2,R²-1,Z-3,R³-1,1), (X-20,Y-3,R¹-2, R²-1,Z-3,R³-2,0), (X-20,Y-3,R¹-2,R²-1,Z-3,R³-2,1), (X-20, Y-3,R¹-2,R²-1,Z-3,R³-3,0), (X-20,Y-3,R¹-2,R²-1,Z-3,R³-3, 1), (X-20,Y-5,R¹-1,R²-1,Z-1,R³-1,0), (X-20,Y-5,R¹-1,R²-1, Z-1,R³-1,1), (X-20,Y-5,R¹-1,R²-1,Z-1,R³-2,0), (X-20,Y-5, R¹-1,R²-1,Z-1,R³-2,1), (X-20,Y-5,R¹-1,R²-1,Z-1,R³-3,0), (X-20,Y-5,R¹-1,R²-1,Z-1,R³-3,1), (X-20,Y-5,R¹-1,R²-1,Z-1, R³-1,0), (X-20,Y-5,R¹-1,R²-1,Z-1,R³-1,1), (X-20,Y-5,R¹-1, R²-1,Z-2,R³-2,0), (X-20,Y-5,R¹-1,R²-1,Z-2,R³-2,1), (X-20, Y-5,R¹-1,R²-1,Z-2,R³-3,0), (X-20,Y-5,R¹-1,R²-1,Z-2,R³-3, 1), (X-20,Y-5,R¹-1,R²-1,Z-2,R³-1,0), (X-20,Y-5,R¹-1,R²-1, Z-2,R³-1,1), (X-20,Y-5,R¹-1,R²-1,Z-2,R³-2,0), (X-20,Y-5, R¹-1,R²-1,Z-2,R³-2,1), (X-20,Y-5,R¹-1,R²-1,Z-3,R³-3,0), (X-20,Y-5,R¹-1,R²-1,Z-3,R³-3,1), (X-20,Y-5,R¹-1,R²-1,Z-3, R³-1,0), (X-20,Y-5,R¹-1,R²-1,Z-3,R³-1,1), (X-20,Y-5,R¹-1, R²-1,Z-3,R³-2,0), (X-20,Y-5,R¹-1,R²-1,Z-3,R³-2,1), (X-20, Y-5,R¹-1,R²-1,Z-3,R³-3,0), (X-20,Y-5,R¹-1,R²-1,Z-3,R³-3, 1), (X-20,Y-5,R¹-2,R²-1,Z-1,R³-1,0), (X-20,Y-5,R¹-2,R²-1, Z-1,R³-1,1), (X-20,Y-5,R¹-2,R²-1,Z-1,R³-2,0), (X-20,Y-5, R¹-2,R²-1,Z-1,R³-2,1), (X-20,Y-5,R¹-2,R²-1,Z-1,R³-3,0), (X-20,Y-5,R¹-2,R²-1,Z-1,R³-3,1), (X-20,Y-5,R¹-2,R²-1,Z-1, R³-1,0), (X-20,Y-5,R¹-2,R²-1,Z-1,R³-1,1), (X-20,Y-5,R¹-2, R²-1,Z-2,R³-2,0), (X-20,Y-5,R¹-2,R²-1,Z-2,R³-2,1), (X-20, Y-5,R¹-2,R²-1,Z-2,R³-3,0), (X-20,Y-5,R¹-2,R²-1,Z-2,R³-3, 1), (X-20,Y-5,R¹-2,R²-1,Z-2,R³-1,0), (X-20,Y-5,R¹-2,R²-1, Z-2,R³-1,1), (X-20,Y-5,R¹-2,R²-1,Z-2,R³-2,0), (X-20,Y-5, R¹-2,R²-1,Z-2,R³-2,1), (X-20,Y-5,R¹-2,R²-1,Z-3,R³-3,0), (X-20,Y-5,R¹-2,R²-1,Z-3,R³-3,1), (X-20,Y-5,R¹-2,R²-1,Z-3, R³-1,0), (X-20,Y-5,R¹-2,R²-1,Z-3,R³-1,1), (X-20,Y-5,R¹-2, R²-1,Z-3,R³-2,0), (X-20,Y-5,R¹-2,R²-1,Z-3,R³-2,1), (X-20, Y-5,R¹-2,R²-1,Z-3,R³-3,0), (X-20,Y-5,R¹-2,R²-1,Z-3,R³-3, 1), (X-20,Y-6,R¹-1,R²-1,Z-1,R³-1,0), (X-20,Y-6,R¹-1,R²-1, Z-1,R³-1,1), (X-20,Y-6,R¹-1,R²-1,Z-1,R³-2,0), (X-20,Y-6, R¹-1,R²-1,Z-1,R³-2,1), (X-20,Y-6,R¹-1,R²-1,Z-1,R³-3,0), (X-20,Y-6,R¹-1,R²-1,Z-1,R³-3,1), (X-20,Y-6,R¹-1,R²-1,Z-1, R³-1,0), (X-20,Y-6,R¹-1,R²-1,Z-1,R³-1,1), (X-20,Y-6,R¹-1, R²-1,Z-2,R³-2,0), (X-20,Y-6,R¹-1,R²-1,Z-2,R³-2,1), (X-20, Y-6,R¹-1,R²-1,Z-2,R³-3,0), (X-20,Y-6,R¹-1,R²-1,Z-2,R³-3, 1), (X-20,Y-6,R¹-1,R²-1,Z-2,R³-1,0), (X-20,Y-6,R¹-1,R²-1, Z-2,R³-1,1), (X-20,Y-6,R¹-1,R²-1,Z-2,R³-2,0), (X-20,Y-6, R¹-1,R²-1,Z-2,R³-2,1), (X-20,Y-6,R¹-1,R²-1,Z-3,R³-3,0), (X-20,Y-6,R¹-1,R²-1,Z-3,R³-3,1), (X-20,Y-6,R¹-1,R²-1,Z-3, R³-1,0), (X-20,Y-6,R¹-1,R²-1,Z-3,R³-1,1), (X-20,Y-6,R¹-1, R²-1,Z-3,R³-2,0), (X-20,Y-6,R¹-1,R²-1,Z-3,R³-2,1), (X-20, Y-6,R¹-1,R²-1,Z-3,R³-3,0), (X-20,Y-6,R¹-1,R²-1,Z-3,R³-3, 1), (X-20,Y-6,R¹-2,R²-1,Z-1,R³-1,0), (X-20,Y-6,R¹-2,R²-1, Z-1,R³-1,1), (X-20,Y-6,R¹-2,R²-1,Z-1,R³-2,0), (X-20,Y-6, R¹-2,R²-1,Z-1,R³-2,1), (X-20,Y-6,R¹-2,R²-1,Z-1,R³-3,0), (X-20,Y-6,R¹-2,R²-1,Z-1,R³-3,1), (X-20,Y-6,R¹-2,R²-1,Z-1, R³-1,0), (X-20,Y-6,R¹-2,R²-1,Z-1,R³-1,1), (X-20,Y-6,R¹-2, R²-1,Z-2,R³-2,0), (X-20,Y-6,R¹-2,R²-1,Z-2,R³-2,1), (X-20, Y-6,R¹-2,R²-1,Z-2,R³-3,0), (X-20,Y-6,R¹-2,R²-1,Z-2,R³-3, 1), (X-20,Y-6,R¹-2,R²-1,Z-2,R³-1,0), (X-20,Y-6,R¹-2,R²-1, Z-2,R³-1,1), (X-20,Y-6,R¹-2,R²-1,Z-2,R³-2,0), (X-20,Y-6, R¹-2,R²-1,Z-2,R³-2,1), (X-20,Y-6,R¹-2,R²-1,Z-3,R³-3,0), (X-20,Y-6,R¹-2,R²-1,Z-3,R³-3,1), (X-20,Y-6,R¹-2,R²-1,Z-3, R³-1,0), (X-20,Y-6,R¹-2,R²-1,Z-3,R³-1,1), (X-20,Y-6,R¹-2, R²-1,Z-3,R³-2,0), (X-20,Y-6,R¹-2,R²-1,Z-3,R³-2,1), (X-20, Y-6,R¹-2,R²-1,Z-3,R³-3,0), (X-20,Y-6,R¹-2,R²-1,Z-3,R³-3, 1), (X-20,Y-7,R¹-1,R²-1,Z-1,R³-1,0), (X-20,Y-7,R¹-1,R²-1, Z-1,R³-1,1), (X-20,Y-7,R¹-1,R²-1,Z-1,R³-2,0), (X-20,Y-7, R¹-1,R²-1,Z-1,R³-2,1), (X-20,Y-7,R¹-1,R²-1,Z-1,R³-1,0), (X-20,Y-7,R¹-1,R²-1,Z-1,R³-1,1), (X-20,Y-7,R¹-1,R²-1,Z-2, R³-2,0), (X-20,Y-7,R¹-1,R²-1,Z-2,R³-2,1), (X-20,Y-7,R¹-1, R²-1,Z-2,R³-3,0), (X-20,Y-7,R¹-1,R²-1,Z-2,R³-3,1), (X-20, Y-7,R¹-1,R²-1,Z-2,R³-1,0), (X-20,Y-7,R¹-1,R²-1,Z-2,R³-1, 1), (X-20,Y-7,R¹-1,R²-1,Z-2,R³-2,0), (X-20,Y-7,R¹-1,R²-1, Z-2,R³-2,1), (X-20,Y-7,R¹-1,R²-1,Z-3,R³-3,0), (X-20,Y-7, R¹-1,R²-1,Z-3,R³-3,1), (X-20,Y-7,R¹-1,R²-1,Z-3,R³-1,0), (X-20,Y-7,R¹-1,R²-1,Z-3,R³-1,1), (X-20,Y-7,R¹-1,R²-1,Z-3, R³-2,0), (X-20,Y-7,R¹-1,R²-1,Z-3,R³-2,1), (X-20,Y-7,R¹-1, R²-1,Z-3,R³-3,0), (X-20,Y-7,R¹-1,R²-1,Z-3,R³-3,1), (X-20, Y-7,R¹-1,R²-2,Z-1,R³-1,0), (X-20,Y-7,R¹-1,R²-2,Z-1,R³-1, 0), (X-20,Y-7,R¹-1,R²-2,Z-1,R³-2,0), (X-20,Y-7,R¹-1,R²-2, Z-1,R³-2,1), (X-20,Y-7,R¹-1,R²-2,Z-1,R³-3,0), (X-20,Y-7, R¹-1,R²-2,Z-1,R³-3,1), (X-20,Y-7,R¹-1,R²-2,Z-1,R³-1,0), (X-20,Y-7,R¹-1,R²-2,Z-1,R³-1,1), (X-20,Y-7,R¹-1,R²-2,Z-2, R³-2,0), (X-20,Y-7,R¹-1,R²-2,Z-2,R³-2,1), (X-20,Y-7,R¹-1, R²-2,Z-2,R³-3,0), (X-20,Y-7,R¹-1,R²-2,Z-2,R³-3,1), (X-20,

Y-7,R¹-1,R²-2,Z-2,R³-1,0), (X-20,Y-7,R¹-1,R²-2,Z-2,R³-1, 1), (X-20,Y-7,R¹-1,R²-2,Z-2,R³-2,0), (X-20,Y-7,R¹-1,R²-2, Z-2,R³-2,1), (X-20,Y-7,R¹-1,R²-2,Z-3,R³-3,0), (X-20,Y-7, R¹-1,R²-2,Z-3,R³-3,1), (X-20,Y-7,R¹-1,R²-2,Z-3,R³-1,0), (X-20,Y-7,R¹-1,R²-2,Z-3,R³-1,1), (X-20,Y-7,R¹-1,R²-2,Z-3, R³-2,0), (X-20,Y-7,R¹-1,R²-2,Z-3,R³-2,1), (X-20,Y-7,R¹-1, R²-2,Z-3,R³-3,0), (X-20,Y-7,R¹-1,R²-2,Z-3,R³-3,1), (X-20, Y-7,R¹-2,R²-1,Z-1,R³-1,0), (X-20,Y-7,R¹-2,R²-1,Z-1,R³-1, 1), (X-20,Y-7,R¹-2,R²-1,Z-1,R³-2,0), (X-20,Y-7,R¹-2,R²-1, Z-1,R³-2,1), (X-20,Y-7,R¹-2,R²-1,Z-1,R³-3,0), (X-20,Y-7, R¹-2,R²-1,Z-1,R³-3,1), (X-20,Y-7,R¹-2,R²-1,Z-1,R³-1,0), (X-20,Y-7,R¹-2,R²-1,Z-1,R³-1,1), (X-20,Y-7,R¹-2,R²-1,Z-2, R³-2,0), (X-20,Y-7,R¹-2,R²-1,Z-2,R³-2,1), (X-20,Y-7,R¹-2, R²-1,Z-2,R³-3,0), (X-20,Y-7,R¹-2,R²-1,Z-2,R³-3,1), (X-20, Y-7,R¹-2,R²-1,Z-2,R³-1,0), (X-20,Y-7,R¹-2,R²-1,Z-2,R³-1, 1), (X-20,Y-7,R¹-2,R²-1,Z-2,R³-2,0), (X-20,Y-7,R¹-2,R²-1, Z-2,R³-2,1), (X-20,Y-7,R¹-2,R²-1,Z-3,R³-3,0), (X-20,Y-7, R¹-2,R²-1,Z-3,R³-3,1), (X-20,Y-7,R¹-2,R²-1,Z-3,R³-1,0), (X-20,Y-7,R¹-2,R²-1,Z-3,R³-1,1), (X-20,Y-7,R¹-2,R²-1,Z-3, R³-2,0), (X-20,Y-7,R¹-2,R²-1,Z-3,R³-2,1), (X-20,Y-7,R¹-2, R²-1,Z-3,R³-3,0), (X-20,Y-7,R¹-2,R²-1,Z-3,R³-3,1), (X-20, Y-7,R¹-2,R²-2,Z-1,R³-1,0), (X-20,Y-7,R¹-2,R²-2,Z-1,R³-1, 1), (X-20,Y-7,R¹-2,R²-2,Z-1,R³-2,0), (X-20,Y-7,R¹-2,R²-2, Z-1,R³-2,1), (X-20,Y-7,R¹-2,R²-2,Z-1,R³-3,0), (X-20,Y-7, R¹-2,R²-2,Z-1,R³-3,1), (X-20,Y-7,R¹-2,R²-2,Z-1,R³-1,0), (X-20,Y-7,R¹-2,R²-2,Z-1,R³-1,1), (X-20,Y-7,R¹-2,R²-2,Z-2, R³-2,0), (X-20,Y-7,R¹-2,R²-2,Z-2,R³-2,1), (X-20,Y-7,R¹-2, R²-2,Z-2,R³-3,0), (X-20,Y-7,R¹-2,R²-2,Z-2,R³-3,1), (X-20, Y-7,R¹-2,R²-2,Z-2,R³-1,0), (X-20,Y-7,R¹-2,R²-2,Z-2,R³-1, 1), (X-20,Y-7,R¹-2,R²-2,Z-2,R³-2,0), (X-20,Y-7,R¹-2,R²-2, Z-2,R³-2,1), (X-20,Y-7,R¹-2,R²-2,Z-3,R³-3,0), (X-20,Y-7, R¹-2,R²-2,Z-3,R³-3,1), (X-20,Y-7,R¹-2,R²-2,Z-3,R³-1,0), (X-20,Y-7,R¹-2,R²-2,Z-3,R³-1,1), (X-20,Y-7,R¹-2,R²-2,Z-3, R³-2,0), (X-20,Y-7,R¹-2,R²-2,Z-3,R³-2,1), (X-20,Y-7,R¹-2, R²-2,Z-3,R³-3,0), (X-20,Y-7,R¹-2,R²-2,Z-3,R³-3,1)

Experiment 1

Affinity for NPY Y5 Receptor cDNA sequence encoding a human NPY Y5 receptor (WO96/16542) was cloned in a vector pME18S (Takebe et al. Mol. Cell. Biol. 8, 8957). The obtained expression vector was transfected into CHO cells as a host by using Lipofect AMINE reagent (Trademark, Gibco BRL Co., Ltd.) according to the instruction 50 manual. The cells that stably express NPY Y5 receptor were obtained.

The membranes prepared from the CHO cells expressing NPY Y5 receptor, the compound of the present invention and 30,000 cpm [$^{125}$I] peptide YY (60 pM of final concentration: Amersham) were incubated in the assay buffer (20 mM HEPES-Hanks buffer containing 0.1% bovine serum albumin, pH 7.4) at 25° C. for 2 hours, and then the membrane was collected by filtering the mixture through a glassfilter (GF/C) presoaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test compound against the specific peptide YY binding ($IC_{50}$ value) was calculated (Inui, A. et al. Endocrinology 131, 2090-2096 (1992)). The results are shown below.

| | |
|---|---|
| Example II-2 | 1.85 nM |
| Example II-12 | 0.55 nM |
| Example II-14 | 0.32 nM |

The compounds of the present invention inhibited the binding of peptide YY (NPY homologue) to NPY Y5 receptor, indicating that the compounds of the present invention have an affinity for the NPY Y5 receptor.

Experiment 2

Under ether anesthesia the skull of male C57BL/6J mice (12-14 week old, 25-30 g) was exposed by making an incision from external occipital crest to nasal dorsum, and drilled in the 1-mm lateral position to the left following 1-mm posterior from bregma. After recovery from anesthesia mice were dosed with either 0.5% hydroxypropylmethyl cellulose solution (Shin-Etsu Chemical Co., Ltd.) or the compounds of the present invention suspended in the 0.5% hydroxypropylmethyl cellulose solution. At one hour after the treatment, each animal received an NPY Y5 receptor specific agonist, [cPP$^{1-7}$, NPY$^{19-23}$, Ala$^{31}$, Aib$^{32}$, Gln$^{34}$]-hPancreatic Polypeptide (0.1 nmol/1.5 μL/mouse) through the skull opening using a canula. Residual food was measured at 2 and 4 hours after the treatment, and the difference in food intake between the compounds-treated mice and 0.5% hydroxymethyl cellulose solution-treated mice was calculated. The compound at 6 mg/kg caused 52% to 85% reduction in food intake of mice compared to the treatment with 0.5% hydroxypropylmethyl cellulose solution, which was statistically significant.

Formulation Example 1

Tablets

| | |
|---|---|
| Compound (I) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture is crushed, granulated and dried to obtain a suitable size of granules. Next, calcium stearate is added to the granules. Finally, tableting is performed under a compression force.

Formulation Example 2

Capsules

| | |
|---|---|
| Compound (I) | 10 mg |
| Magnesium stearate | 10 mg |
| Lactose | 80 mg |

The above ingredients are mixed uniformly to obtain powders or fine granules, and then the obtained mixture is filled into capsules.

Formulation Example 3

Granules

| Compound (I) | 30 g |
| Lactose | 265 g |
| Magnesium stearate | 5 g |

After the above ingredients are mixed uniformly, the mixture is compressed, crushed, granulated and sieved to obtain a suitable size of granules.

Industrial Applicability

As shown in the above Experiments, the compounds of the present invention have an NPY Y5 receptor antagonistic activity. Therefore, the compounds of the present invention are very useful as an anti-obesity drug and an anorectic agent.

The invention claimed is:

1. A compound of the formula (I):

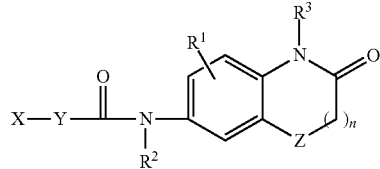

or its pharmaceutically acceptable salt thereof,
wherein
X is hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy, optionally substituted alkoxycarbonyl, optionally substituted aryloxy, optionally substituted aryloxycarbonyl, optionally substituted alkylthio, optionally substituted arylthio, —S(O)m—$R^4$, —C(=O)$R^4$, —C(=S)$NR^4R^5$ or —C(=O)$NR^4R^5$,
Y is a group of the formula:

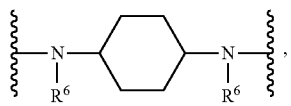

Z is —O—,
$R^1$ is hydrogen, carboxy, hydroxy, nitro, halogen, cyano, mercapto, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy, optionally substituted alkoxycarbonyl, optionally substituted aryloxy, optionally substituted aryloxycarbonyl, optionally substituted alkylthio, optionally substituted arylthio, optionally substituted carbamoyl, optionally substituted thiocarbamoyl, optionally substituted acyl or optionally substituted sulfamoyl,
$R^4$ is hydrogen, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted amino, optionally substituted alkoxy or optionally substituted aryloxy, provided that when X is —S(O)m—$R^4$, $R^4$ is not hydrogen,
$R^2$, $R^3$, $R^5$, $R^6$ and $R^7$ are each independently hydrogen, hydroxy, optionally substituted alkyl or optionally substituted acyl,
m is 1 or 2,
n is 0,
p is 0 to 6,
provided that N-(3,4-dihydro-3-oxo-2H-1,4-benzoxazin-6-yl)-N'-[2-[ethyl(3-methylphenyl)amino]ethyl]-urea, N-[3-(diethylamino)propyl]-N'-(2,3-dihydro-2-oxo-1H-benzimidazol-5-yl)-urea and N,N''-1,6-hexanediyl-bis[N'-(2,3-dihydro-2-oxo-6-benzoxazolyl)]-urea are excluded.

2. The compound of claim 1, or its pharmaceutically acceptable salt thereof, wherein a group of the formula (I):

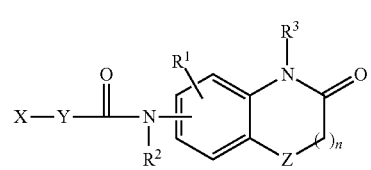

is a group of the formula (II):

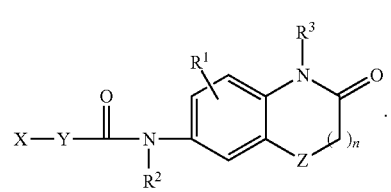

3. The compound of claim 1, or its pharmaceutically acceptable salt thereof, wherein $R^6$ is hydrogen or optionally substituted alkyl.

4. The compound of claim 1, or its pharmaceutically acceptable salt thereof, wherein X is —S(O)$_m$—$R^4$ (m is 2), —C(=O)$R^4$, —C(=S)$NR^4R^5$ or —C(=O)$NR^4R^5$ ($R^4$ and $R^5$ have the same meaning as defined in claim 1).

5. The compound of claim 4, or its pharmaceutically acceptable salt thereof, wherein $R^4$ is optionally substituted alkyl or optionally substituted cycloalkyl.

6. The compound of claim 4, or its pharmaceutically acceptable salt thereof, wherein $R^5$ is hydrogen or optionally substituted alkyl.

7. The compound of claim 1, or its pharmaceutically acceptable salt thereof, wherein $R^1$ is hydrogen, halogen or optionally substituted alkyl.

8. The compound of claim 1, or its pharmaceutically acceptable salt thereof, wherein $R^2$ is hydrogen.

9. The compound of claim 1, or its pharmaceutically acceptable salt thereof, wherein $R^3$ is optionally substituted alkyl.

10. The compound of claim 9, or its pharmaceutically acceptable salt thereof, wherein $R^3$ is isopropyl.

11. A pharmaceutical composition comprising the compound of claim 1, or its pharmaceutically acceptable salt thereof.

12. The pharmaceutical composition according to claim 11, which has an NPY Y5 receptor antagonistic activity.

13. The pharmaceutical composition according to claim 11, or its pharmaceutically acceptable salt thereof, which is used as an anorectic agent or an anti-obesity drug.

* * * * *